US007741374B1

(12) United States Patent  (10) Patent No.: US 7,741,374 B1
Arnold et al.  (45) Date of Patent: *Jun. 22, 2010

(54) METHODS OF USE OF FENOFIBRIC ACID

(75) Inventors: Kristin Anne Arnold, Morrisville, PA (US); Hengsheng Feng, Cherry Hill, NJ (US)

(73) Assignee: Mutual Pharmaceutical Company, Inc., Philadelphia, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/556,644

(22) Filed: Sep. 10, 2009

Related U.S. Application Data

(63) Continuation of application No. 12/501,678, filed on Jul. 13, 2009, which is a continuation of application No. 12/141,377, filed on Jun. 18, 2008, now Pat. No. 7,569,612, which is a continuation of application No. 12/056,725, filed on Mar. 27, 2008, which is a continuation-in-part of application No. 11/971,460, filed on Jan. 9, 2008, which is a continuation of application No. 11/841,328, filed on Aug. 20, 2007, now abandoned.

(60) Provisional application No. 60/823,006, filed on Aug. 21, 2006, provisional application No. 60/940,113, filed on May 25, 2007.

(51) Int. Cl.
*A61K 31/12* (2006.01)
(52) U.S. Cl. .................................................... 514/687
(58) Field of Classification Search .................. 514/687
See application file for complete search history.

(56) References Cited

U.S. PATENT DOCUMENTS

| | | | |
|---|---|---|---|
| 3,053,255 A | 9/1962 | Meyer |
| 3,843,480 A | 10/1974 | Dreher |
| 3,948,254 A | 4/1976 | Zaffaroni |
| 3,948,262 A | 4/1976 | Zaffaroni |
| 3,993,073 A | 11/1976 | Zaffaroni |
| 4,310,509 A | 1/1982 | Berglund et al. |
| 4,485,097 A | 11/1984 | Bell |
| 4,505,891 A | 3/1985 | Ito |
| 4,542,012 A | 9/1985 | Dell |
| 4,560,555 A | 12/1985 | Snider |
| 4,597,961 A | 7/1986 | Etscorn |
| 4,608,249 A | 8/1986 | Otsuka et al. |
| 4,806,356 A | 2/1989 | Shaw |
| 4,940,587 A | 7/1990 | Jenkins et al. |
| 5,084,278 A | 1/1992 | Mehta |
| 5,178,878 A | 1/1993 | Wehling et al. |
| 5,800,834 A | 9/1998 | Spireas et al. |
| 5,968,550 A | 10/1999 | Spireas et al. |
| 6,096,337 A | 8/2000 | Spireas et al. |
| 6,197,348 B1 | 3/2001 | Morella et al. |
| 6,221,392 B1 | 4/2001 | Khankari et al. |
| 6,423,339 B1 | 7/2002 | Spireas |
| 7,022,337 B2 | 4/2006 | Liang et al. |
| 7,259,186 B2 | 8/2007 | Cink et al. |
| 2003/0077297 A1 | 4/2003 | Chen et al. |
| 2003/0194442 A1 | 10/2003 | Guivarch et al. |
| 2003/0235595 A1 | 12/2003 | Chen et al. |
| 2005/0096390 A1 | 5/2005 | Holm et al. |
| 2005/0096391 A1 | 5/2005 | Holm et al. |
| 2005/0148594 A1 | 7/2005 | Cink et al. |
| 2005/0276974 A1 | 12/2005 | Ryde et al. |
| 2006/0068015 A1 | 3/2006 | Holm et al. |
| 2006/0105050 A1 | 5/2006 | Holm et al. |
| 2006/0110444 A1 | 5/2006 | Holm et al. |
| 2006/0134196 A1 | 6/2006 | Rosenberg et al. |
| 2006/0222706 A1 | 10/2006 | Flashner-Barak et al. |
| 2006/0222707 A1 | 10/2006 | Lerner et al. |
| 2006/0257470 A1 | 11/2006 | Rosenberg et al. |
| 2006/0280790 A1 | 12/2006 | Ju et al. |
| 2006/0280791 A1* | 12/2006 | Ju et al. ................. 424/464 |
| 2007/0009603 A1 | 1/2007 | Holm et al. |
| 2007/0014846 A1 | 1/2007 | Holm et al. |
| 2007/0015834 A1 | 1/2007 | Flashner-Barak et al. |
| 2007/0026062 A1 | 2/2007 | Holm et al. |
| 2007/0128278 A1 | 6/2007 | Ju et al. |
| 2007/0148233 A1 | 6/2007 | Lerner et al. |
| 2007/0148234 A1 | 6/2007 | Ju et al. |
| 2007/0185199 A1 | 8/2007 | Ju et al. |
| 2007/0190138 A1 | 8/2007 | Holm |
| 2007/0264334 A1 | 11/2007 | Ju et al. |
| 2008/0051411 A1 | 2/2008 | Cink et al. |

(Continued)

FOREIGN PATENT DOCUMENTS

| | | |
|---|---|---|
| EP | 1829541 A1 | 12/2003 |
| EP | 1572190 B1 | 4/2007 |
| EP | 1832285 A1 | 9/2007 |
| WO | 2006135480 A2 | 12/2006 |
| WO | 2008037809 A1 | 4/2008 |

(Continued)

OTHER PUBLICATIONS

Chiarla et al., "Severe Hypocholesterolemia in surgical patients, sepsis, and critical illness," J Crit Care (2009), article still in press and printed from Science Direct and PubMed <<http://www.sciencedirect.com/science?_ob=ArticleURL&_udi=B7590-4XFF2N4-3&_user=2502287&_rdoc=1&_fmt=&_orig=search&_sort=d&_docanchor=&view=c&_acct=C000055109&_ver>>.*

(Continued)

*Primary Examiner*—Ardin Marschel
*Assistant Examiner*—Amy A Lewis
(74) *Attorney, Agent, or Firm*—Cantor Colburn, LLP

(57) ABSTRACT

Fenofibric acid formulations comprising 105 mg of fenofibric acid are described as well as methods of use thereof. Dosage forms include, for example, immediate-release dosage forms.

2 Claims, No Drawings

FOREIGN PATENT DOCUMENTS

| | | |
|---|---|---|
| WO | 02067901 A1 | 9/2002 |
| WO | 2004054568 A1 | 7/2004 |
| WO | 2005034908 A2 | 4/2005 |
| WO | 2005034920 A1 | 4/2005 |
| WO | 2006037344 A1 | 4/2006 |
| WO | 2006017411 A2 | 10/2006 |
| WO | 2006107316 A1 | 10/2006 |
| WO | 2006107357 A1 | 10/2006 |

OTHER PUBLICATIONS

Farnier, Michael; "Update on the clinical utility of fenofibrate in mixed dyslipidemias: mechanisms of action and rational prescribing"; Vascular Health and Risk Management; 4(5); pp. 991-1000 (2008).

Fazio, S.; "Management of mixed dyslipidemia in patients with or at risk for cardiovascular disease: a role for combination fibrate therapy"; Abstract only; Clin. Ther. 30(2); pp. 294-306 (2008).

* cited by examiner

METHODS OF USE OF FENOFIBRIC ACID

CROSS REFERENCE TO RELATED APPLICATION

This application is a continuation of U.S. Ser No. 12/501,678 filed on Jul. 13, 2009, which is a continuation of U.S. Ser. No. 12/141,377 filed on Jun. 18, 2008, now U.S. Pat. No. 7,569,612, which is a continuation of U.S. Ser. No. 12/056,725 filed on Mar. 27, 2008, which is a continuation in part of U.S. Ser. No. 11/971,460 filed on Jan. 9, 2008, which is a continuation of U.S. Ser. No. 11/841,328 filed on Aug. 20, 2007, claiming priority from U.S. Provisional Application Ser. Nos. 60/823,006 filed Aug. 21, 2006 and 60/940,113 filed May 25, 2007, all which are hereby incorporated by reference in their entirety.

BACKGROUND

Fenofibrate, 2-[4-(4-chlorobenzoyl)phenoxy]-2-methyl-propanoic acid, 1-methylethyl ester, is used in the treatment of endogenous hyperlipidaemias, hypercholesterolaemias and hypertriglyceridaemias in adults. Fenofibric acid, the active metabolite of fenofibrate, produces reductions in total cholesterol, LDL cholesterol, apolipoprotein B, total triglycerides and triglyceride rich lipoprotein (VLDL) in treated patients. Also, treatment with fenofibrate results in increases in high-density lipoprotein (HDL) and apoproteins apoAI and apoAII. Prolonged treatment with fenofibrate at the rate of about 300 to about 400 mg per day makes it possible to obtain a reduction in total cholesterol of about 20 to about 25% and a reduction in the levels of triglycerides of about 40 to about 50%.

Fenofibrate is not soluble in water, which limits its absorption in the gastrointestinal (GI) tract. To remedy this problem, research groups have tried a multitude of strategies including, for example, formulations comprising reduced sized fenofibrate, the combination of fenofibrate and vitamin E, the use of diethylene glycol monoethyl ether (DGME) as solubilizer, and the combination of fenofibrate with one or more polyglycolyzed glycerides.

The present invention addresses the need for improved lipid regulating agent dosage forms, particularly dosage forms comprising fenofibric acid.

SUMMARY

In one embodiment, method of treating a patient in need of treatment for primary hypercholesterolemia or mixed hyperlipidemia comprises administering to the patient a 105 mg fenofibric acid dosage form.

In another embodiment, a pharmaceutical dosage form comprises 105 mg of fenofibric acid and a pharmaceutically acceptable excipient.

In another embodiment, a pharmaceutical package comprises a pharmaceutical dosage form comprising 105 mg of fenofibric acid and a pharmaceutically acceptable excipient, and instructions that the dosage form can be administered with food or without food.

These and other embodiments, advantages and features of the present invention become clear when detailed description and examples are provided in subsequent sections.

DETAILED DESCRIPTION

Disclosed herein are dosage forms comprising fenofibric acid as an active agent. In some embodiments, the fenofibric acid dosage forms are equivalent, e.g., bioequivalent, to the fenofibrate dosage forms Tricor® 145 mg or 48 mg when dosed under fasted conditions, non-fasted conditions, or a combination thereof. In other embodiments, the fenofibric acid dosage forms are bioequivalent when fasted conditions are compared to non-fasted conditions. Non-fasted conditions include a high fat meal, a standard meal, or a low fat meal as defined herein.

Based on a direct conversion using the molecular weights of fenofibrate and fenofibric acid, it is calculated that a 145 mg fenofibrate dosage form should be equivalent to approximately a 128 mg fenofibric acid dosage form. The commercially available Tricor® 145 mg fenofibrate dosage form is reportedly bioequivalent when administered under fasted and non-fasted conditions due to the nanoparticulate form of the fenofibrate in the dosage form. Because fenofibric acid does not have the same water insolubility as fenofibrate, it was expected that fenofibric acid would exhibit similar pharmacokinetics when administered under fasted compared to non-fasted conditions as compared to Tricor® 145. It has been unexpectedly discovered by the inventors herein, however, that an immediate-release 130 mg fenofibric acid dosage form may not be bioequivalent to a 145 mg fenofibrate dosage form when administered under both fasted and non-fasted conditions. While an immediate-release 130 mg fenofibric acid dosage form tested was substantially bioequivalent to a Tricor® 145 reference under non-fasted conditions, the immediate-release 130 mg fenofibric acid dosage form exhibited a significantly higher $C_{max}$ than the Tricor® 145 reference under fasted conditions. In other words, the 130 mg immediate-release fenofibric acid dosage form exhibited a higher $C_{max}$ under fasted conditions compared to non-fasted conditions. This is in contrast to many fenofibrate dosage forms, such as those containing micronized fenofibrate, in which the dosage forms exhibit improved bioavailability when administered under non-fasted conditions compared to fasted conditions. In a practical sense, the data indicates that one cannot simply convert dosage amounts of fenofibrate to fenofibric acid molar equivalents to determine the amount of fenofibric acid to be employed in a fenofibric acid dosage form. A careful study of the pharmacokinetic parameters for all proposed fenofibric acid dosage strength is required.

Without being held to theory, one possibility is that the chemical properties of the fenofibric acid itself contribute to the difference in bioavailability of certain fenofibric acid dosage forms when administered under non-fasted compared to fasted conditions. Food changes the pH of the stomach from about 1 to about 4-4.5. This change in pH favors drug absorption. Fenofibric acid, however, is a hydrophilic drug and it is possible that a hydrophobic high fat meal could bind a hydrophobic drug resulting in decreased absorption. The decreased absorption of fenofibric acid with food suggests that the effect of binding to food may dominate over the increased absorption expected with a change in the pH of the stomach.

In one embodiment, the dosage strength of fenofibric acid is optimized to provide a fenofibric acid dosage form that is bioequivalent to a Tricor® 145 reference under both non-fasted and fasted conditions. In contrast to a 130 mg dosage form as calculated from the weights of fenofibrate and fenofibric acid, it has been unexpectedly found by the inventors herein that a 105 mg fenofibric acid dosage form is bioequivalent to a Tricor® 145 reference under both non-fasted and fasted conditions. Because Tricor® 145 has been optimized as a nanoparticulate formulation to improve its bioavailability, it was unexpected that less than a molar equivalent of fenofibric acid, that is less than 130 mg, would provide a dosage form that is bioequivalent to Tricor® 145. In one embodiment, the fenofibric acid dosage form is an immediate release dosage form. In another embodiment, it was unexpected, given the higher absorption of fenofibric acid as compared to fenofibrate, that an immediate-release dosage form comprising fenofibric acid has equivalent bioavailability to Tricor® 145.

In one embodiment, a method of treating a patient in need of treatment for primary hypercholesterolemia or mixed hyperlipidemia, comprises administering to the patient a 105 mg fenofibric acid dosage form, such as an immediate-release dosage form. In another embodiment, the 105 mg fenofibric acid dosage form is bioequivalent to a nanoparticulate 145 mg fenofibrate dosage form, such as a Tricor® 145, described in the U.S. Federal Food and Drug Administration's New Drug Application No. 021656 approved on Nov. 5, 2004. In one embodiment, the nanoparticulate 145 mg fenofibrate dosage form comprises particles with a D50 of less than about 500 nm. The 105 mg fenofibric acid dosage form can be a single daily dose.

In another embodiment, a fenofibric acid dosage form can be administered without regard to meals. As used herein, a composition that can be administered without regard to meals exhibits a ratio of a logarithmic transformed geometric mean $AUC_{0-t}$ of the composition administered in a non-fasted state to a logarithmic transformed geometric mean $AUC_{0-t}$ of the composition administered in a fasted state of about 0.80 to about 1.25, and/or a ratio of a logarithmic transformed geometric mean Cmax of the composition administered in a non-fasted state to a logarithmic transformed geometric mean Cmax of the composition administered in a fasted state of about 0.80 to about 1.25. Decreased concentrations of fenofibric acid observed following administration with food may lead to decreased efficacy, decreased in Cmax, decreased $AUC_{o-t}$, decreased $AUC_{o-inf}$, or any combination thereof.

In one embodiment, a method of treating a patient in need of treatment for primary hypercholesterolemia or mixed hyperlipidemia, comprises administering to the patient a 105 mg fenofibric acid dosage form such as an immediate-release dosage form. In one embodiment, the 105 mg fenofibric acid dosage form is bioequivalent to a nanoparticulate 145 mg fenofibrate dosage form under, for example, fasted conditions, low fat meal non-fasted conditions, standard meal non-fasted conditions, or a combination of two or more of the foregoing. In one embodiment, the nanoparticulate 145 mg fenofibrate dosage form comprises particles with a D50 of less than about 500 nm. In another embodiment, the 105 mg fenofibric acid dosage form is a single daily dose.

In one embodiment, the 105 mg fenofibric acid dosage form exhibits a mean $C_{max}$ within ±50% of 10,650 ng/ml when administered under fasted conditions, non-fasted conditions, or both. In another embodiment, the 105 mg fenofibric acid dosage form exhibits a mean $C_{max}$ within 80% to 125% of 10,650 ng/ml when administered under fasted conditions, non-fasted conditions, or both. In yet another embodiment, wherein the 105 mg fenofibric acid dosage form exhibits a mean $AUC_{0-t}$ of within ±50% of 158,700 hr*ng/ml when administered under fasted conditions, non-fasted conditions, or both. In another embodiment, the 105 mg fenofibric acid dosage form exhibits a mean $AUC_{0-t}$ of within 80% to 125% of 158700 hr*ng/ml when administered under fasted conditions, non-fasted conditions, or both. In specific embodiments, the non-fasted conditions are a low-fat meal, a standard meal, or both.

In one embodiment, the 105 mg fenofibric acid dosage form is administered without regard to meals. Administering without regard to meals includes, for example, administering under fasted conditions, a low fat meal, or a standard meal. In specific embodiments, the 105 mg fenofibric acid dosage form exhibits a ratio of a logarithmic transformed geometric mean $AUC_{0-t}$ of the composition administered in a non-fasted state to a logarithmic transformed geometric mean $AUC_{0-t}$ of the composition administered in a fasted state of about 0.80 to about 1.25, wherein the non-fasted state comprises administration of a low-fat meal; the 105 mg fenofibric acid dosage form exhibits a ratio of a logarithmic transformed geometric mean $AUC_{0-INF}$ of the composition administered in a non-fasted state to a logarithmic transformed geometric mean $AUC_{0-INF}$ of the composition administered in a fasted state of about 0.80 to about 1.25, wherein the non-fasted state comprises administration of a low-fat meal; the 105 mg fenofibric acid dosage form exhibits a ratio of a logarithmic transformed geometric mean Cmax of the composition administered in a non-fasted state to a logarithmic transformed geometric mean Cmax of the composition administered in a fasted state of about 0.80 to about 1.25, wherein the non-fasted state comprises administration of a low-fat meal; the 105 mg fenofibric acid dosage form exhibits a ratio of a logarithmic transformed geometric mean $AUC_{0-t}$ of the composition administered in a non-fasted state to a logarithmic transformed geometric mean $AUC_{0-t}$ of the composition administered in a fasted state of about 0.80 to about 1.25, wherein the non-fasted state comprises administration of a standard meal; the 105 mg fenofibric acid dosage form exhibits a ratio of a logarithmic transformed geometric mean $AUC_{0-INF}$ of the composition administered in a non-fasted state to a logarithmic transformed geometric mean $AUC_{0-INF}$ of the composition administered in a fasted state of about 0.80 to about 1.25, wherein the non-fasted state comprises administration of a standard meal; the 105 mg fenofibric acid dosage form exhibits a ratio of a logarithmic transformed geometric mean Cmax of the composition administered in a non-fasted state to a logarithmic transformed geometric mean Cmax of the composition administered in a fasted state of about 0.80 to about 1.25, wherein the non-fasted state comprises administration of a standard meal; the 105 mg fenofibric acid dosage form exhibits a ratio of a logarithmic transformed geometric mean $AUC_{0-t}$ of the composition administered in a non-fasted state to a logarithmic transformed geometric mean $AUC_{0-t}$ of the composition administered in a fasted state of about 0.80 to about 1.25, wherein the non-fasted state comprises administration of a high-fat meal; the 105 mg fenofibric acid dosage form exhibits a ratio of a logarithmic transformed geometric mean $AUC_{0-INF}$ of the composition administered in a non-fasted state to a logarithmic transformed geometric mean $AUC_{0-INF}$ of the composition administered in a fasted state of about 0.80 to about 1.25, wherein the non-fasted state comprises administration of a high-fat meal; and/or the 105 mg fenofibric acid dosage form exhibits a ratio of a logarithmic transformed geometric mean Cmax of the composition administered in a non-fasted state to a logarithmic transformed geometric mean Cmax of the composition administered in a fasted state of about 0.60 to about 1.25, wherein the non-fasted state comprises administration of a high-fat meal.

In other embodiments, the 105 mg fenofibric acid dosage form exhibits a ratio of a mean $AUC_{0-t}$ of the composition administered in a non-fasted state to a mean $AUC_{0-t}$ of the composition administered in a fasted state of +25% to −20% of 0.9466, wherein the non-fasted state comprises administration of a low-fat meal; the 105 mg fenofibric acid dosage form exhibits a ratio of a mean $AUC_{0-INF}$ of the composition administered in a non-fasted state to a mean $AUC_{0-INF}$ of the composition administered in a fasted state of +25% to −20% of 0.9554, wherein the non-fasted state comprises administration of a low-fat meal; the 105 mg fenofibric acid dosage form exhibits a ratio of a mean Cmax of the composition administered in a non-fasted state to a mean Cmax of the composition administered in a fasted state of +25% to −20% of 0.8121, wherein the non-fasted state comprises administration of a low-fat meal; the 105 mg fenofibric acid dosage form exhibits a ratio of a mean $AUC_{0-t}$ of the composition administered in a non-fasted state to a mean $AUC_{0-t}$ of the composition administered in a fasted state of +25% to −20% of 0.9611, wherein the non-fasted state comprises administration of a standard meal; the 105 mg fenofibric acid dosage form exhibits a ratio of a mean $AUC_{0-INF}$ of the composition administered in a non-fasted state to a mean $AUC_{0-INF}$ of the composition administered in a fasted state of +25% to −20% of 0.9689, wherein the non-fasted state comprises administration of a standard meal; the 105 mg fenofibric acid dosage form exhibits a ratio of a mean Cmax of the composition administered in a non-fasted state to a mean Cmax of the composition administered in a fasted state of +25% to −20% of 0.8190, wherein the non-fasted state comprises administration of a standard meal; the 105 mg fenofibric acid dosage form exhibits a ratio of a mean $AUC_{0-t}$ of the composition administered in a non-fasted state to a mean $AUC_{0-t}$ of the composition administered in a fasted state of +25% to −20% of 0.9618, wherein the non-fasted state comprises administration of a high-fat meal; the 105 mg fenofibric acid dosage form exhibits a ratio of a mean $AUC_{0-INF}$ of the composition administered in a non-fasted state to a mean $AUC_{0-INF}$ of the composition administered in a fasted state of +25% to −20% of 0.9714, wherein the non-fasted state comprises administration of a high-fat meal; and/or the 105 mg fenofibric acid dosage form exhibits a ratio of a mean Cmax of the composition administered in a non-fasted state to a mean Cmax of the composition administered in a fasted state of +25% to −20% of 0.6628, wherein the non-fasted state comprises administration of a high-fat meal.

In one embodiment, administering a 105 mg fenofibric acid dosage form comprises informing that without regard to meals excludes administration with a high-fat meal. In another embodiment, administering comprises informing the patient that the fenofibric acid dosage form has no food effect when fasting conditions are compared to a low fat meal or a standard meal. In another embodiment, the 105 mg fenofibric acid dosage form exhibits an $AUC_{0-2}$ under fasted conditions of ±30% of 10403 ng-h/ml and under non-fasted conditions of ±30% of 3881 ng-h/ml. In another embodiment, the 105 mg fenofibric acid dosage form exhibits an $AUC_{0-3}$ under fasted conditions of ±30% of 19700 ng-h/ml and under non-fasted conditions of ±30% of 9230 ng-h/ml.

In another embodiment the 105 mg fenofibric acid dosage form exhibits a mean $C_{max}$ within 80% to 125% of 11840.9 ng/ml when administered under fasted conditions, and a mean $AUC_{0-t}$ of within 80% to 125% of 132066 hr*ng/ml when administered under fasted conditions, the 105 mg fenofibric acid dosage form exhibits a mean $C_{max}$ within 80% to 125% of 9564.9 ng/ml when administered under low-fat meal non-fasted conditions, and a mean $AUC_{0-t}$ of within 80% to 125% of 124223 hr*ng/ml when administered under low-fat meal non-fasted conditions, the 105 mg fenofibric acid dosage form exhibits a mean $C_{max}$ within 80% to 125% of 9691.13 ng/ml when administered under standard meal non-fasted conditions, and a mean $AUC_{0-t}$ of within 80% to 125% of 125951 hr*ng/ml when administered under standard meal non-fasted conditions, and/or the 105 mg fenofibric acid dosage form exhibits a mean $C_{max}$ within 80% to 125% of 7745 ng/ml when administered under high fat meal non-fasted conditions, and a mean $AUC_{0-t}$ of within 80% to 125% of 127262 hr*ng/ml when administered under high-fat meal non-fasted conditions.

In another embodiment, a fenofibric acid dosage from is administered without regard to meals, in other words, fasted or with a low fat or standard meal. In another embodiment, the fenofibric acid dosage form is administered once daily. In yet another embodiment, the fenofibric acid dosage form is administered once daily, and it is recommended that the drug be taken at the same time each day, on an empty stomach or with a low fat or standard meal.

A method of using fenofibric acid comprises informing a patient that the fenofibric acid dosage form can be administered without regard to meals. The term without regard to meals includes fasted, with a low fat meal, with a standard meal, or with a high fat meal. In one embodiment, a method of using fenofibric acid comprises informing a user that a fenofibric acid dosage form has no food effect when fasted conditions are compared to a low fat meal or a standard meal.

For example, in a study of 18 patients administered a 105 mg fenofibric acid dosage form with a low fat meal compared to fasting, the ratio of a logarithmic transformed geometric mean $AUC_{0-t}$ of the composition administered in a non-fasted state to a logarithmic transformed geometric mean $AUC_{0-t}$ of the composition administered in a fasted state was 0.94. In a study of 18 patients administered fenofibric acid with a low-fat meal compared to fasting, the ratio of a logarithmic transformed geometric mean Cmax of the composition administered in a non-fasted state to a logarithmic transformed geometric mean Cmax of the composition administered in a fasted state was 0.808.

In a study of 18 patients administered a 105 mg fenofibric acid dosage form with a standard meal compared to fasting, the ratio of a logarithmic transformed geometric mean $AUC_{0-t}$ of the composition administered in a non-fasted state to a logarithmic transformed geometric mean $AUC_{0-t}$ of the composition administered in a fasted state was 0.954. In a study of 18 patients administered fenofibric acid with a standard meal compared to fasting, the ratio of a logarithmic transformed geometric mean Cmax of the composition administered in a non-fasted state to a logarithmic transformed geometric mean Cmax of the composition administered in a fasted state was 0.818.

In a study of 18 patients administered a 105 mg fenofibric acid dosage form with a high fat meal compared to fasting, the ratio of a logarithmic transformed geometric mean $AUC_{0-t}$ of the composition administered in a non-fasted state to a logarithmic transformed geometric mean $AUC_{0-t}$ of the composition administered in a fasted state was 0.963. In a study of 18 patients administered fenofibric acid with a standard meal compared to fasting, the ratio of a logarithmic transformed geometric mean Cmax of the composition administered in a non-fasted state to a logarithmic transformed geometric mean Cmax of the composition administered in a fasted state was 0.654.

In order to understand the pharmacokinetic properties of a fenofibric acid dosage form, it is useful to study the partial AUC of the dosage form, that is, portions of the total concentration curve. In one embodiment, a fenofibric acid dosage form exhibits an $AUC_{0-2}$ (i.e., and area under the curve from 0 to 2 hours) under fasted conditions of ±30% of 10403 ng-h/ml and under non-fasted conditions of ±30% of 3881 ng-h/ml. In other words, the 105 mg dosage form exhibits an $AUC_{0-2}$ that is substantially bioequivalent to Tricor® 145 under fasting and non-fasted conditions. In another embodiment, a fenofibric acid dosage form exhibits an $AUC_{0-3}$ (i.e., and area under the curve from 0 to 3 hours) under fasted conditions of ±30% of 19700 ng-h/ml and under non-fasted conditions of ±30% of 9230 ng-h/ml. In other words, the 105 mg dosage form exhibits an $AUC_{0-3}$ that is substantially bioequivalent to Tricor® 145 under fasting and non-fasted conditions. It was unexpected that within 2 hours of administration a 105 mg fenofibric acid dosage form would have a substantially similar AUC as Tricor® 145 mg, particularly when Tricor® 145 mg exhibits poor availability in the first hour when dosed under fasted conditions.

Optimally, the fenofibric acid form (e.g., a 105 mg fenofibric acid dosage form) is bioequivalent under fasted and non-fasted conditions to Tricor® 145 mg. In one embodiment, the mean $AUC_{0-t}$ for the dosage form, when measured under fasted and non-fasted conditions, differs by less than about 30%. In another embodiment, the mean $C_{max}$ for the dosage form, when measured under fasted and non-fasted conditions, differs by less than about 30%. In yet another embodiment, both the mean $AUC_{0-t}$ and the mean $C_{max}$ for the dosage form, when measured under fasted and non-fasted conditions, differ by less than about 30%. In one embodiment, the mean $AUC_{0-t}$ and/or the mean $C_{max}$ are measured in a study of at least about 20 subjects. In another embodiment, the mean $C_{max}$ of the dosage form is ±50% of 11,000 ng/ml and the mean $AUC_{0-t}$ of the dosage form is ±50% of 150,000 hr*ng/ml. The amount of fenofibric acid in the dosage form comprises 90 mg to less than 130 mg of fenofibric acid, specifically 96 mg to 126 mg, more specifically 100 mg to 120 mg, and yet more specifically 103 mg to 117 mg. In a specific embodiment, the dosage form is a 105 mg dosage form. In this embodiment, the dosage form is optionally packaged with instructions that the dosage form can be administered with food or without food, or an equivalent thereof.

In another embodiment, the chemical properties of the fenofibric acid itself contribute to the reduced bioavailability of fenofibric acid when administered under non-fasted compared to fasted conditions. In this embodiment, it is possible to optimize the dosage strength of the fenofibric acid in the dosage form so that the dosage form is bioequivalent when administered under fasted and non-fasted conditions. In this embodiment, non-fasted conditions include a high fat meal, a standard meal, or a low fat meal as defined herein. In this embodiment, a immediate-release fenofibric acid dosage form that is bioequivalent when administered under fasted and non-fasted conditions comprises 100 mg to 120 mg of fenofibric acid, specifically 103 mg to 117 mg, and most specifically 105 mg. In one embodiment, the dosage form comprises 111 mg of fenofibric acid. In one embodiment, the mean $AUC_{0-t}$ for the dosage form, when measured under fasted and non-fasted conditions in a study of at least about 20 subjects, differs by less than about 30%. In another embodiment, the mean $C_{max}$ for the dosage form, when measured under fasted and non-fasted conditions in a study of at least about 20 subjects, differs by less than about 30%. In yet another embodiment, both the mean $AUC_{0-t}$ and the mean $C_{max}$ for the dosage form, when measured under fasted and non-fasted conditions in a study of at least about 20 subjects, differ by less than about 30%. In one embodiment, the mean $AUC_{0-t}$ and/or the mean $C_{max}$ are measured in a study of at least about 20 subjects. In another embodiment, the mean $C_{max}$ of the dosage form is ±50% of 11,000 ng/ml and the mean $AUC_{0-t}$ of the dosage form is ±50% of 150,000 hr*ng/ml. In another embodiment, the mean $C_{max}$ of the dosage form is within 80% to 125% of 11,000 ng/ml and the mean $AUC_{0-t}$ of the dosage form is within 80% to 125% of 150,000 hr*ng/ml. In one embodiment, the dosage form is a tablet. In this embodiment, the dosage form is optionally packaged with instructions that the dosage form can be administered with food or without food, wherein food means a high fat meal, a standard meal, or a low fat meal, or an equivalent thereof.

In another embodiment, a fenofibric acid dosage form is bioequivalent to the to the commercially available Tricor® 145 mg fenofibrate dosage form when administered under fasted conditions. In this embodiment, the amount of fenofibric acid in the dosage form comprises 85 mg to 120 mg of fenofibric acid, specifically 87 mg to 116 mg, and most specifically 105 mg. In this embodiment, the dosage form is optionally packaged with instructions that the dosage form should be administered without food, or an equivalent thereof.

In one embodiment, the mean $C_{max}$ of a fenofibric acid dosage form is ±50% of 11,000 ng/ml when administered under fasted conditions, non-fasted conditions, or both. In one embodiment, the mean $C_{max}$ of a fenofibric acid dosage form is within 80% to 125% of 11,000 ng/ml when administered under fasted conditions, non-fasted conditions, or both.

In one embodiment, the mean $AUC_{0-t}$ of a fenofibric acid dosage form is within 80% to 125% of 150,000 hr*ng/ml when administered under fasted conditions, non-fasted conditions, or both.

Embodiments of fenofibric acid dosage forms include buffered formulations, immediate release formulations, enteric coated formulations, delayed release formulations, extended-release formulations, pulsed-release formulations, orally disintegrating formulations including effervescent formulations, taste masked formulations, lozenge formulations, amorphous fenofibric acid formulations, particulate fenofibric acid formulations, nanoparticulate fenofibric acid formulations, microparticulate fenofibric acid formulations, suspension formulations, solution formulations, transdermal formulations, injectable formulations, spray dried fenofibric acid powders, emulsion formulations, microemulsion formulations, formulations, gum-based formulations, formulations based on matrix polymers, osmotic pump formulations, formulations with zero-order release, multi-layer formulations comprising an immediate-release layer and a controlled or extended-release layer, pellet formulations comprising sugar spheres or microcrystalline cellulose spheres, liqui-gel formulations, liqui-solid formulations, floating dosage forms, bioadhesive dosage forms, extended-release matrix dosage forms, and the like. In one embodiment, an immediate release dosage form is a tablet or a capsule.

In one embodiment, a fenofibric acid dosage form comprises less than 130 mg of fenofibric acid. In other embodiments, a fenofibric acid dosage form comprises less than 125, less than 120, less than 110, or less than 105 mg of fenofibric acid. In another embodiment, a fenofibric acid dosage form comprises greater than 10, 15, 20, 25, 30, 35, 40, 45, 50, 55, 60, 65 or 70 mg of fenofibric acid. On one embodiment, a fenofibric acid dosage form comprises 95 to 105 mg of fenofibric acid. In another embodiment, a fenofibric acid dosage form comprises 96 mg or 102 mg or 105 or 111 mg of fenofibric acid.

In another embodiment, the fenofibric acid dosage form is an immediate release dosage form. In one embodiment, an immediate release fenofibrate dosage form has a $T_{max}$ upon administration to a human subject of 3 hours ±2.5 hour. Administration may be performed in the fasted state or in the non-fasted state. In another embodiment, the immediate release fenofibrate dosage form has an in vitro release of 90% or greater at 2 hours measured in a single pH buffer such as a pH 6.8 buffer, in a standard dissolution tester.

In one embodiment, the fenofibric acid dosage form comprises no added surfactant. In another embodiment, the fenofibric acid dosage form is not in the form of a liquid dispersion, a solid dispersion, or an emulsion. As used herein, a surfactant is limited to amphipathic compounds (as opposed to polymers) that contain both a hydrophobic region and a hydrophilic region. Surfactants can be anionic, cationic, zwitterionic, or nonionic. Specific surfactants that are excluded from the scope of the composition in this embodiment are sodium lauryl sulfate, sodium dioctyl sulfosuccinate, and phospholipids (a class of lipids formed from a fatty acid, a phosphate group, a nitrogen-containing alcohol and a backbone such as a glycerol backbone or a sphingosine backbone.)

In one embodiment, the fenofibric acid dosage form comprises a distintegrant such as crosslinked polyvinylpyrrollidone. Disintegrants are used to facilitate tablet disintegration or "breakup" after administration. The amount of disintegrant used depends upon the disintegrant or disintegrant combination chosen and the targeted release profile of the resulting formulation. Disintegrants include conventional disintegrants such as a starch or a pre-gelatinized starch, or superdisintegrants that are effective when used in a lesser quantity than that required when a conventional disintegrant is used. Examples of such superdisintegrants include crosslinked polyvinylpyrrolidone, sodium starch glycolate, and crosslinked carboxymethyl cellulose, and combinations comprising one or more of the foregoing superdisintegrants. In one embodiment, the disintegrant is sodium starch glycolate. In an exemplary embodiment, the disintegrant is crosslinked polyvinylpyrrolidone (PVP-XL).

The disintegrant or superdisintegrant is present in the fenofibric acid dosage form in an amount of about 1 wt % to about 30 wt %, or more specifically, about 1 wt % to about 15 wt %, or even more specifically, about 1 wt % to about 10 wt %, based on the total weight of the fenofibric acid dosage form.

In one embodiment, the fenofibric acid dosage form comprises a filler (sometime interchangeably used as "diluent"). Suitable fillers are one or more compounds which are capable of providing compactability and good flow. Suitable fillers include, but are not limited to, sugars, silicic acid, starch, cellulosic polymers, dibasic calcium phosphate, calcium carbonate, calcium sulfate, and a combination comprising two or more of the foregoing fillers. Exemplary sugars include, but are not limited to, lactose, sucrose, glucose, dextrose, maltodextrin, mannitol, and sorbitol. Exemplary lactoses include, but are not limited to, lactose monohydrate, NF (Fast Flo), lactose spray-dried monohydrate, and lactose anhydrous. Exemplary cellulosic polymers include, but are not limited to, microcrystalline cellulose (MCC), for example, AVICEL® PH101 and AVICEL® PH102, which are commercially available from FMC Biopolymer, Philadelphia, Pa. Exemplary dibasic calcium phosphates include, but are not limited to, dihydrated and anhydrous dibasic calcium phosphates. In one embodiment, the filler is a combination of microcrystalline cellulose, for example, AVICEL® PH101, and lactose monohydrate, NF (Fast Flo).

The amount of the filler in the fenofibric acid dosage form is about 10 wt % to about 99 wt %, or more specifically, about 30 wt % to about 90 wt %, or even more specifically, about 50 wt % to about 90 wt %, based on the total weight of the fenofibric acid dosage form. In one embodiment, the total amount of the filler is about 70 wt % to about 85 wt %, based on the total weight of the fenofibric acid dosage form.

In one embodiment, the fenofibric acid dosage form comprises a binder. Binders are used to impart cohesive qualities to a tablet formulation, and thus ensure that the tablet remains intact after compaction. Suitable binders include, but are not limited to, starches (for example, Starch 1500® or pregelatinized starch), alignates, gelatin, carboxymethylcellulose, sugars (for example, sucrose, glucose, dextrose, and maltodextrin), waxes, natural and synthetic gums, polyvinylpyrrolidone (PVP), and cellulosic polymers (for example, microcrystalline cellulose, hydroxypropyl cellulose, hydroxypropyl methylcellulose, methyl cellulose, and hydroxyethyl cellulose). In one embodiment, the binder is Starch 1500®, commercially available from Colorcon® Inc., West Point Pa. Starch 1500® is a pharmaceutical grade of partially pregelatinized maize starch. Starch 1500® brings benefits to formulas through binding capability, improved disintegrant properties, and enhanced flow and lubricity. In one embodiment, the binder is starch (for example, pregelatinized starch or Starch 1500®). In an exemplary embodiment, the binder is polyvinylpyrrolidone (PVP).

The amount of the binder in the fenofibric acid dosage form is about 0.1 wt % to about 30 wt %, or more specifically, about 1 wt % to about 20 wt %, or even more specifically, about 1 wt % to about 15 wt %, based on the total weight of the fenofibric acid dosage form. In one embodiment, the amount of the binder is about 3 wt % to about 10 wt %, based on the total weight of the fenofibric acid dosage form.

In another embodiment, the fenofibric acid dosage form comprises a lubricant. Generally, a lubricant is added just before tableting step, and is mixed with the rest of the composition for a minimum period of time to obtain good dispersal. Suitable lubricants include, but are not limited to, stearate salts, stearic acid, talc, glyceryl behenate, polyethylene glycol, polyethylene oxide polymers (for example, available under the registered trademarks of Carbowax™ for polyethylene glycol and Polyox™ for polyethylene oxide from Dow Chemical Company, Midland, Mich.), sodium lauryl sulfate, magnesium lauryl sulfate, sodium oleate, sodium stearyl fumarate, DL-leucine, colloidal silica, and a combination comprising two or more of the foregoing lubricants. In one embodiment, the lubricant is stearate salts, or more specifically, magnesium stearate, calcium stearate, or zinc stearate. It is recognized that certain materials can function both as a glidant and a lubricant The lubricant in the fenofibric acid dosage form is present in an amount of about 0.01 wt % to about 10 wt %, or more specifically, about 0.1 wt % to about 5 wt %, based on the total weight of the fenofibric acid dosage form.

The fenofibric acid dosage form optionally comprises a glidant. Glidants include, for example, silicon dioxide, specifically colloidal silicon dioxide.

In one embodiment, a fenofibric acid dosage form comprises 9 to 13% fenofibric acid. In another embodiment, a 1000 mg blend suitable for the formation of a fenofibric acid dosage form comprises:

| | |
|---|---|
| Fenofibric acid | 125 mg |
| Microcrystalline cellulose | 783.4 mg |
| Copovidone | 50.0 mg |
| Crospovidone | 33.3 mg, and |
| Magnesium Stearate | 8.3 mg. |

The blend is used in formulating different strength fenofibric acid tablets. Each weight is mg ingredient to form 1 gram of the blend, and then the required amount of blend is selected to make tablets that are a certain weight. For example, an 840 mg blend is used to make 105 mg tablets: 125/1000=x/860, x=105 so 860 mg of blend is used to make the 105 mg tablets.

An "active agent" means a compound, element, or mixture that when administered to a patient, alone or in combination with another compound, element, or mixture, confers, directly or indirectly, a physiological effect on the patient. The indirect physiological effect may occur via a metabolite or other indirect mechanism. When the active agent is a compound, then salts, solvates (including hydrates) of the free compound or salt, crystalline forms, non-crystalline forms, and any polymorphs and co-crystals of the compound are contemplated herein. Compounds may contain one or more asymmetric elements such as stereogenic centers, stereogenic axes and the like, e.g., asymmetric carbon atoms, so that the compounds can exist in different stereoisomeric forms. These compounds can be, for example, racemates or optically active forms. For compounds with two or more asymmetric elements, these compounds can additionally be mixtures of diastereomers. For compounds having asymmetric centers, all optical isomers in pure form and mixtures thereof are encompassed. In addition, compounds with carbon-carbon double bonds may occur in Z- and E-forms, with all isomeric forms of the compounds. In these situations, the single enantiomers, i.e., optically active forms can be obtained by asymmetric synthesis, synthesis from optically pure precursors, or by resolution of the racemates. Resolution of the racemates can also be accomplished, for example, by conventional methods such as crystallization in the presence of a resolving agent, or chromatography, using, for example a chiral HPLC column. All forms are contemplated herein regardless of the methods used to obtain them.

"Bioavailability" means the extent or rate at which an active agent is absorbed into a living system or is made available at the site of physiological activity. For active agents that are intended to be absorbed into the bloodstream, bioavailability data for a given formulation may provide an estimate of the relative fraction of the administered dose that is absorbed into the systemic circulation. "Bioavailability" can be characterized by one or more pharmacokinetic parameters.

A "co-crystal" means a multi-component crystalline material containing at least two different materials which are solid at room temperature.

A "dosage form" means a unit of administration of an active agent. Examples of dosage forms include tablets, capsules, injections, suspensions, liquids, emulsions, creams, ointments, suppositories, inhalable forms, transdermal forms, and the like.

"Efficacy" means the ability of an active agent administered to a patient to produce a therapeutic effect in the patient.

"Food" typically means a solid food or mixed solid/liquid food with sufficient bulk and fat content that it is not rapidly dissolved and absorbed in the stomach. In one embodiment, food means a meal, such as breakfast, lunch or dinner. The terms "taken with food", "fed" and "non-fasted" are equivalent and are as given by FDA guidelines and criteria. In one embodiment, with food means that the dosage form is administered to a patient between about 30 minutes prior to about 2 hours after eating a meal. In another embodiment, with food means that the dosage form is administered at substantially the same time as the eating the meal.

As used herein, with food or non-fasted includes administration with a high fat meal, a standard meal or a low fat meal. In a high fat test meal, about 50% of the 800-1000 calories in the meal are from fat. A representative high fat, high calorie test meal comprises 2 eggs fried in butter, 2 strips of bacon, 2 slices of toast with butter, 4 ounces of hash brown potatoes, and 8 ounces of whole milk. A standard meal comprises about 700 calories and includes 2 slices of toast, ¾ cup cereal, 2 tsp jelly, 1 tsp sugar, 2 tsp margarine, 6 fluid ounces orange juice, and one milk. A low fat meal comprises about 400 calories and includes one low fat muffin with margarine, one cup cornflakes, 6 fluid ounces apple juice, and one skim milk.

The terms "without food", "fasted" and "an empty stomach" are equivalent and are as given by FDA guidelines and criteria. In one embodiment, fasted is means the condition wherein no food is consumed within 1 hour prior to administration of the dosage form or 2 hours after administration of the dosage form. In another embodiment, fasted means the condition wherein no food is consumed within 1 hour prior to administration of the dosage form to 2 hours after administration of the dosage form.

"Pharmacokinetic parameters" describe the in vivo characteristics of an active agent (or surrogate marker for the active agent) over time, such as plasma concentration (C), $C_{max}$, $C_n$, $C_{24}$, $T_{max}$, and AUC. "$C_{max}$" is the measured concentration of the active agent in the plasma at the point of maximum concentration. "$C_n$" is the measured concentration of an active agent in the plasma at about n hours after administration. "$C_{24}$" is the measured concentration of an active agent in the plasma at about 24 hours after administration. The term "$T_{max}$" refers to the time at which the measured concentration of an active agent in the plasma is the highest after administration of the active agent. "AUC" is the area under the curve of a graph of the measured concentration of an active agent (typically plasma concentration) vs. time, measured from one time point to another time point. For example $AUC_{0-t}$ is the area under the curve of plasma concentration versus time from time 0 to time t. When no specific time "t" is referred to, the area under the plasma concentration-time curve from time zero to the time of measurement of the last quantifiable concentration is referred to as $AUC_{0-t}$. Partial AUC is an AUC specific for a particular time period, such as $AUC_{0-2}$, $AUC_{0-3}$. An advantage of measuring a partial AUC is that the exposure early after dosing is measured. The $AUC_{0-\infty}$ or $AUC_{0-INF}$ is the calculated area under the curve of plasma concentration versus time from time 0 to time infinity.

As used herein a mean $T_{max}$ is an average of $T_{max}$ values obtained from a minimum of 8 human subjects, specifically a minimum of 20 human subjects.

"Safety" means the incidence or severity of adverse events associated with administration of an active agent, including adverse effects associated with patient-related factors (e.g., age, gender, ethnicity, race, target illness, abnormalities of renal or hepatic function, co-morbid illnesses, genetic characteristics such as metabolic status, or environment) and active agent-related factors (e.g., dose, plasma level, duration of exposure, or concomitant medication).

As used herein, for the purposes of biostudy and the determination of bioequivalence, a non-fasted patient is defined as a patient who fasts for at least 10 hours overnight and then consumes an entire test meal within 30 minutes of first ingestion. The dosage form is administered with 240 mL of water at 30 minutes after first ingestion of the meal. No food is then allowed for at least 4 hours post-dose. Water can be allowed ad libitum after 2 hours. A high fat test meal provides approximately 1000 calories to the patient of which approximately 50% of the caloric content is derived from fat content of the meal. A representative high fat high calorie test meal comprises 2 eggs fried in butter, 2 strips of bacon, 2 slices of toast with butter, 4 ounces of hash brown potatoes, and 8 ounces of whole milk to provide 150 protein calories, 250 carbohydrate calories, and 500 to 600 fat calories.

Disclosed herein are compositions, such as dosage forms, comprising fenofibric acid. The fenofibric acid may be in free or salt form. Fenofibric acid salts include base addition salts. Suitable base addition salts include salts with inorganic bases, for example metal hydroxides or carbonates of alkali metals, alkaline earth metals or transition metals, or with organic bases, for example ammonia, basic amino acids such as arginine and lysine, amines, e.g., methylamine, dimethylamine, trimethylamine, triethylamine, ethylamine, diethylamine, ethylenediamine, ethanolamine, diethanolamine, 1-amino-2-propanol, 3-amino-1-propanol or hexamethylenetetraamine, saturated cyclic amines having 4 to 6 ring carbon atoms, such as piperidine, piperazine, pyrrolidine and morpholine, and other organic bases, for example N-methylglucamine, kreatine and tromethamine, and quaternary ammonium compounds such as tetramethylammonium and the like. Suitable salts with organic bases are formed with amino acids. Suitable salts with inorganic bases are formed with Na, K, Mg and Ca cations. Specific fenofibric acid salts include choline, ethanolamine, diethanolamine, piperazine, calcium and tromethamine salts.

Additional salts of fenofibric acid also include acid addition salts, the moroxydine salt, cinnarizine-salt, and sodium salt.

"Reference drug" means a fenofibrate product as described in the U.S. Federal Food and Drug Administration's New Drug Application No. 021656 approved on Nov. 5, 2004 as provided in the U.S. Federal Food and Drug Administration's Orange Book, Approved Drug Products with Therapeutic Equivalence Evaluations. Tricor® is a nanoparticulate fenofibrate tablet product at a strength of 145 and 48 mg which is sold by Abbott.

The approved prescribing information for TriCor® 145 and 48 mg states that "Exposure to fenofibric acid in plasma, as measured by Cmax and AUC, is not significantly different when a single 145 mg dose of fenofibrate is administered under fasting or nonfasting conditions."

TriCor® 145 and 48 mg comprise particles of fenofibrate having associated with the surface thereof a surface stabilizer comprising hypromellose, sodium lauryl sulfate and dioctyl sodium sulfosuccinate (also known as docusate sodium or DOSS), wherein the fibrate particles have an effective average particle size of less than about 2000 nm. According to US 2005/0276974, a fenofibrate dosage form having bioequivalency under fasted and non-fasted conditions comprises (a) about 119 to about 224 g/kg fenofibrate; (b) about 42 to about 46 g/kg hypromellose; (c) about 2 to about 6 g/kg docusate sodium; (d) about 119 to about 224 g/kg sucrose; (e) about 12 to about 18 g/kg sodium lauryl sulfate; (f) about 119 to about 224 g/kg lactose monohydrate; (g) about 129 to about 134 g/kg silicified microcrystalline cellulose; (h) about 112 to about 118 g/kg crospovidone; and (i) about 0.5 to about 3 g/kg magnesium stearate.

"Bioequivalence" means the absence of a significant difference in the rate and extent to which the active agent or surrogate marker for the active agent in pharmaceutical equivalents or pharmaceutical alternatives becomes available at the site of action when administered in an appropriately designed study.

In one embodiment, bioequivalence is any definition thereof as promulgated by the U.S. Food and Drug Administration or any successor agency thereof. In a specific embodiment, bioequivalence is determined according to the Federal Drug Administration's (FDA) guidelines and criteria, including "GUIDANCE FOR INDUSTRY BIOAVAILABILITY AND BIOEQUVALENCE STUDIES FOR ORALLY ADMINISTERED DRUG PRODUCTS—GENERAL CONSIDERATIONS" available from the U.S. Department of Health and Human Services (DHHS), Food and Drug Administration (FDA), Center for Drug Evaluation and Research (CDER) March 2003 Revision 1; and "GUIDANCE FOR INDUSTRY STATISTICAL APPROACHES TO ESTABLISHING BIOEQUIVALENCE" DHHS, FDA, CDER, January 2001, both of which are incorporated herein in their entirety.

In another embodiment, bioequivalence is determined according to the European Medicines Agency (EMEA) document "Note for Guidance on the Investigation of Bioavailability and Bioequivalence", issued Jul. 26, 2001, available from EMEA.

In one embodiment, the fenofibric acid compositions are bioequivalent to TriCor® tablet formulations commercially available in the United States, for example the reference drug of NDA # 021656. In other embodiments, the fenofibric acid compositions are bioequivalent to TriCor® tablet formulations under fasted conditions, under non-fasted conditions, or both.

In one embodiment, bioequivalence of a fenofibric acid composition to a reference drug is determined by an in vivo bioequivalence study to determine a pharmacokinetic parameter for the fenofibric acid composition. Specifically, bioequivalence can be determined by an in vivo bioequivalence study comparing a pharmacokinetic parameter for the two compositions. A pharmacokinetic parameter for the fenofibric acid composition or the reference drug can be measured in a single or multiple dose bioequivalence study using a replicate or a nonreplicate design. For example, the pharmacokinetic parameters for a fenofibric acid composition of the present invention and for a reference drug can be measured in a single dose bioequivalence study using a two-period, two-sequence crossover design. Alternately, a four-period, replicate design crossover study may also be used. Single doses of the test composition and reference drug are administered and blood or plasma levels of the active agent are measured over time. Pharmacokinetic parameters characterizing the rate and extent of active agent absorption are evaluated statistically.

The area under the plasma concentration-time curve from time zero to the time of measurement of the last quantifiable concentration ($AUC_{0-t}$) and to infinity ($AUC_{0-\infty}$), $C_{max}$ and $T_{max}$ can be determined according to standard techniques. For statistical analysis of pharmacokinetic data, the logarithmic transformed $AUC_{0-t}$, $AUC_{0-\infty}$, or $C_{max}$ data can be analyzed statistically using analysis of variance.

Under U.S. FDA guidelines, two products (e.g., an inventive composition and TriCor® 145) or methods (e.g., dosing under non-fasted versus fasted conditions) are bioequivalent if the 90% Confidence Intervals (CI) for a logarithmic transformed geometric mean of the ratio of the $AUC_{0-\infty}$, $AUC_{0-t}$, and $C_{max}$ for the two products or methods are about 0.80 to about 1.25.

To show bioequivalence between two compounds or administration conditions pursuant to Europe's EMEA guidelines, the 90% CI for a logarithmic transformed geometric mean of the ratio of $AUC_{0-\infty}$ and $AUC_{0-t}$ for the two products or methods are about 0.80 to about 1.25 and the 90% CI for a logarithmic transformed geometric mean of the ratio of $C_{max}$ for the two products or methods can have a wider acceptance range when justified by safety and efficacy considerations, for example the acceptance range can be about 0.70 to about 1.43, specifically about 0.75 to about 1.33, and more specifically about 0.80 to about 1.25.

In one embodiment, when compared to the reference drug of NDA # 021656, the fenofibric acid compositions have 90% Confidence Intervals (CI) for a logarithmic transformed geometric mean of the ratio of the $AUC_{0-\infty}$, $AUC_{0-t}$, or $C_{max}$ of about 0.80 to about 1.25.

In a given experiment, a fenofibric acid composition is considered to be bioequivalent to TriCor® if both of the obtained logarithmic transformed geometric mean Test/Reference $AUC_{0-\infty}$, $AUC_{0-t}$, or $C_{max}$ ratio along with their corresponding lower and upper 90% CI limits are within a lower limit of about 0.80 and an upper limit of about 1.25. Thus, for direct comparison between a fenofibric acid composition and TriCor®, it is sometimes preferred to determine the pharmacokinetic parameters for the fenofibric acid composition and TriCor® side-by side in the same set of experiments.

In one embodiment, the logarithmic transformed $AUC_{0-t}$ of the fenofibric acid composition is within about 80% and about 125% of 144652 hr*ng/ml; the logarithmic transformed $AUC_{0-\infty}$ of the fenofibric acid composition is within about 80% and about 125% of 167445 hr*ng/ml; or the logarithmic transformed $C_{max}$ of the fenofibric acid composition is within about 70% and about 143% of 167445 ng/ml, specifically within about 80% and about 125% of 167445 ng/ml. The fenofibric acid composition may have a logarithmic transformed $AUC_{0-t}$, logarithmic transformed $AUC_{0-\infty}$, or logarithmic transformed $C_{max}$ as described for TriCor® 145.

In one embodiment, the logarithmic transformed $AUC_{0-t}$ of the fenofibric acid composition is within about 80% and about 125% of 156937 hr*ng/ml; the logarithmic transformed $AUC_{0-\infty}$ of the fenofibric acid composition is within about 80% and about 125% of 172570 hr*ng/ml; or the logarithmic transformed $C_{max}$ of the fenofibric acid composition is within about 70% and about 143% of 10629 ng/ml, specifically within about 80% and about 125% of 10629 ng/ml. The fenofibric acid composition may have a logarithmic transformed $AUC_{0-t}$, logarithmic transformed $AUC_{0-\infty}$, or logarithmic transformed $C_{max}$ as described for TriCor® 145.

In another embodiment, a fenofibric acid composition has an $AUC_{0-t}$ of 40200 to 314000 hr*ng/ml, an $AUC_{0-\infty}$ of 46000 to 373000 hr*ng/ml, and/or a $C_{max}$ of 3000 to 23000 ng/ml.

In another embodiment, a fenofibric acid composition has an $AUC_{0-t}$ of 120768 to 156764 hr*ng/ml, an $AUC_{0-\infty}$ of 139040 to 186493 hr*ng/ml, and/or a $C_{max}$ of 9096 to 11393 ng/ml. The compositions of the present invention may have an $AUC_{0-t}$, $AUC_{0-INF}$, and $C_{max}$ as described for TriCor® 145.

In some embodiments, a single dose bioequivalence study is performed under non-fasted or fasted conditions.

In other embodiments, a single dose bioequivalence study is conducted comparing the fenofibric acid composition and the reference listed drug using the strength specified by the FDA in APPROVED DRUG PRODUCTS WITH THERAPEUTIC EQUIVALENCE EVALUATIONS(ORANGE BOOK).

In some embodiments, an in vivo bioequivalence study is performed to compare all fenofibric acid compositions with corresponding strengths of TriCor® (e.g., 145 or 48 mg fenofibrate). In other embodiments, an in vivo bioequivalence study is performed only for a fenofibric acid composition optionally at an equivalent of the strength of the reference listed drug product for TriCor® (the highest approved strength, or 145 mg as of Nov. 5, 2004) and at the other lower strengths, the fenofibric acid compositions meet the fenofibrate dissolution test described herein.

Bioequivalence can be determined for fenofibrate and fenofibric acid compositions under different administration conditions, e.g., non-fasted versus fasted. Exemplary study considerations can be found in the Federal Drug Administration's (FDA) guidelines and criteria, including "Guidance for Industry, Food-Effect Bioavailability and Fed Bioequivalence Studies" available from the U.S. Department of Health and Human Services (DHHS), Food and Drug Administration (FDA), Center for Drug Evaluation and Research (CDER) December 2002, incorporated herein in its entirety.

In one embodiment, fenofibric acid compositions have reduced fasted/non-fasted effects compared to prior formulations such as, for example TriCor® 160 mg and 54 mg. For TriCor® 160 mg and 54 mg, the absorption of fenofibrate is increased by about 35% when administered with food. Thus, for the inventive dosage forms, the difference in pharmacokinetic parameters between the non-fasted and fasted state should be less than 35%. The difference in $C_{max}$, $AUC_{0-\infty}$, $T_{max}$ or a combination comprising one or more of the foregoing pharmacokinetic parameters for the fenofibric acid composition, when administered in the non-fasted versus the fasted state, is less than about 25%, less than about 20%, less than about 15%, less than about 10%, less than about 5%, or less than about 3%. In one embodiment, the difference in $C_{max}$ and $AUC_{0-\infty}$ for the fenofibric acid composition, when administered in the non-fasted versus the fasted state, is less than about 25%, less than about 20%, less than about 15%, less than about 10%, less than about 5%, or less than about 3%. In another embodiment, the difference in $C_{max}$, $AUC_{0-\infty}$, and $T_{max}$ for the fenofibric acid composition, when administered in the non-fasted versus the fasted state, is less than about 25%, less than about 20%, less than about 15%, less than about 10%, less than about 5%, or less than about 3%.

In one embodiment, the fenofibric acid composition when administered under fasted conditions is bioequivalent to the fenofibric acid composition administered under non-fasted conditions if the 90% Confidence Intervals (CI) for a logarithmic transformed geometric mean of the ratio of the $AUC_{0-\infty}$, $AUC_{0-t}$, or $C_{max}$ for the two methods are about 0.80 to about 1.25.

In one embodiment, the fenofibric acid composition is more bioavailable when administered under fasting conditions than when administered under non-fasted conditions. Without being held to theory, it is believed that the hydrophilicity of fenofibric acid results in less absorption in the non-fasted state because the fat in food inhibits absorption.

In one embodiment, fenofibric acid formulations exhibit bioequivalence to fenofibrate formulations comprising nanoparticulate fenofibrate such as, for example, TriCor® 145 mg and 48 mg. Characteristics of the composition include: (i) the solid dose is bioequivalent to the TriCor® 160 mg tablet comprising micronized fenofibrate and/or (ii) the solid dose is bioequivalent to the TriCor® 145 mg tablet comprising nanoparticulate fenofibrate, wherein bioequivalency is established by a 90% Confidence Interval of 0.80 to 1.25 a log transformed geometric mean of for both $C_{max}$ and AUC or a 90% Confidence Interval of 0.80 to 1.25 for a log transformed geometric mean of AUC and a 90% Confidence Interval of 0.70 to 1.43 for a log transformed geometric mean of $C_{max}$. In another embodiment, characteristics of the composition include: (i) the solid dose is bioequivalent to the TriCor® 54 mg tablet comprising micronized fenofibrate and/or (ii) the solid dose is bioequivalent to the TriCor® 48 mg tablet comprising nanoparticulate fenofibrate, wherein bioequivalency is established by a 90% Confidence Interval of between 0.80 and 1.25 for a log transformed geometric mean of both $C_{max}$ and AUC or a 90% Confidence Interval of between 0.80 and 1.25 for a log transformed geometric mean of AUC and a 90% Confidence Interval of between 0.70 to 1.43 for a log transformed geometric mean of $C_{max}$.

Another pharmacokinetic parameter that may be measured is $T_{max}$. According to the description of TriCor®, the pharmacokinetic profile of the tablets contain parameters such that the median $T_{max}$ is about 6 to about 8 hours (Physicians Desk Reference, $56^{th}$ Ed., 2002).

In another embodiment, the fenofibric acid compositions are bioequivalent to Triglide™ tablet formulations commercially available in the United States, for example the reference drug of NDA# 021350.

In several embodiments, a fenofibric acid dosage form is suitable for oral administration. Oral administration may involve swallowing, so that the compound enters the gastrointestinal tract, or buccal or sublingual administration may be employed by which the compound enters the blood stream directly from the mouth. Formulations suitable for oral administration include solid formulations such as tablets; capsules containing particulates, liquids, or powders; lozenges (including liquid-filled); chews; multi- and nano-particulates; gels; solid solution; liposome; films; sprays; and liquid formulations.

In one embodiment, a fenofibric acid dosage form comprises a buffering agent. Without being held to theory, it is believed that buffering a fenofibric acid dosage form to greater than pH 4 can increase the solubility of fenofibric acid, provide a quicker onset of action, and decrease stomach upset. In one embodiment, the pH of a fenofibric acid dosage form is greater than pH 4, specifically pH 4 to 7. Suitable buffering agents include sodium carbonate, sodium bicarbonate, potassium carbonate, potassium bicarbonate, sodium phosphate, sodium biphosphate, potassium phosphate monobasic, potassium phosphate dibasic, organic bases, amines, and combinations comprising one or more of the foregoing buffering agents.

In one embodiment, a fenofibric acid dosage form is an immediate-release dosage form. An immediate-release dosage form is one in which the release properties of the active agent from the dosage form are essentially unmodified. An immediate-release dosage form results in delivery of greater then or equal to about 75% the fenofibric acid within about 2 hours of administration, specifically within 1 hour of administration. An immediate-release dosage form may contain optional excipients so long as the excipients do not significantly extend the release time of the fenofibric acid.

In another embodiment, a fenofibric acid dosage form is an enteric coated dosage form. An enteric coating is a coating that prevents release of the fenofibric acid until the dosage form reaches the small intestine. Enteric-coated dosage forms comprise fenofibric acid coated with an enteric polymer. The enteric polymer should be non-toxic and is predominantly soluble in the intestinal fluid, but substantially insoluble in the gastric juices. Examples include polyvinyl acetate phthalate (PVAP), hydroxypropylmethyl-cellulose acetate succinate (HPMCAS), cellulose acetate phthalate (CAP), methacrylic acid copolymer, hydroxy propyl methylcellulose succinate, cellulose acetate succinate, cellulose acetate hexahydrophthalate, hydroxypropyl methylcellulose hexahydrophthalate, hydroxypropyl methylcellulose phthalate (HPMCP), cellulose propionate phthalate, cellulose acetate maleate, cellulose acetate trimellitate, cellulose acetate butyrate, cellulose acetate propionate, methacrylic acid/methacrylate polymer (acid number 300 to 330 and also known as EUDRAGIT® L or EUDRAGIT® S, which are anionic copolymers based on methacrylate and available as a powder) also known as methacrylic acid copolymer, type A NF, methacrylic acid-methyl methacrylate copolymer, ethyl methacrylate-methylmethacrylate-chlorotrimethylammonium ethyl methacrylate copolymer, and the like, and combinations comprising one or more of the foregoing enteric polymers. Other examples include natural resins, such as shellac, SANDARAC®, copal collophorium, and combinations comprising one or more of the foregoing polymers. Yet other examples of enteric polymers include synthetic resins bearing carboxyl groups. The methacrylic acid:acrylic acid ethyl ester 1:1 copolymer solid substance of the acrylic dispersion sold under the trade designation "EUDRAGIT® L-100-55" may be suitable.

In one embodiment, a fenofibric acid dosage form is a delayed-release dosage form. "Delayed-release" means that there is a time-delay before significant plasma levels of the active agent are achieved. A delayed-release formulation of an active agent can avoid an initial burst of the active agent, or can be formulated so that release of the active agent in the stomach is avoided and absorption is effected in the small intestine.

In one embodiment, delayed-release tablets comprise a core, a first coating and optionally a second coating. The core includes the fenofibric acid, and excipients, such as a lubricant, and a binder and/or a filler, and optionally a glidant as well as other excipients.

Suitable lubricants include, for example, stearic acid, magnesium stearate, glyceryl behenate, talc, mineral oil (in PEG), and combinations comprising one or more of the foregoing lubricants. Suitable binders include, for example, water-soluble polymers, such as modified starch, gelatin, polyvinylpyrrolidone, polyvinyl alcohol, and combinations comprising one or more of the foregoing lubricants. Suitable fillers include, for example, lactose, microcrystalline cellulose, and the like. An example of a glidant is silicon dioxide (AEROSIL®, Degussa).

The core comprises, for example, by dry weight, about 0.1 to about 50 wt. % fenofibric acid or a pharmaceutically acceptable salt thereof, about 0.5 to about 10 wt. % lubricant, and about 2 to about 98 wt. % binder or filler.

In one embodiment, the first coating comprises a semipermeable coating to achieve delayed-release of the fenofibric acid. The first coating comprises, for example, a water-insoluble, film-forming polymer, together with a plasticizer and a water-soluble polymer. Suitable water-insoluble, film-forming polymers include, for example, cellulose ethers, such as ethylcellulose; cellulose esters, such as cellulose acetate; polyvinylalcohol; and combinations comprising one or more of the foregoing water-insoluble, film-forming polymers. A suitable water-insoluble film-forming polymer is ethylcellulose (available from Dow Chemical under the trade name ETHOCEL®). Suitable water-soluble polymers include polyvinylpyrrolidone. Other excipients are optionally present in the first coating, such as, for example, acrylic acid derivatives (e.g., EUDRAGIT®, Rohm Pharma, Degussa), pigments, etc.

The first coating contains about 20 to about 85 wt. % water-insoluble, polymer (e.g., ethylcellulose), about 10 to about 75 wt. % water-soluble polymer (e.g., polyvinylpyrrolidone), and about 5 to about 30 wt. % plasticizer. The relative proportions of ingredients, notably the ratio of water-insoluble, film-forming polymer to water-soluble polymer, can be varied depending on the release profile to be obtained (where a more delayed-release is generally obtained with a higher amount of water-insoluble, film-forming polymer).

The weight ratio of first coating to tablet core is about 1:30 to about 3:10, specifically about 1:10.

The optional second coating is designed to protect the coated tablet core from coming into contact with gastric juice, thereby preventing a food effect. The second coating comprises, for example, an enteric polymer of the methacrylic type and optionally a plasticizer. The second coating comprises, for example, about 40 to about 95 wt. % enteric polymer (e.g., EUDRAGIT® L30D-55) and about 5 to about 60 wt. % plasticizer (e.g., triethyl citrate, polyethylene glycol). The relative proportions of ingredients, notably the ratio of methacrylic polymer to plasticizer can be varied according to a methods known to those of skill in the art of pharmaceutical formulation.

An exemplary process for preparing a delayed-release dosage form of the fenofibric acid comprises manufacturing a core by, for example, wet or dry granulation techniques. Alternatively, the fenofibric acid and lubricant may be mixed in a granulator and heated to the melting point of the lubricant to form granules. This mixture is then mixed with a suitable filler and compressed into tablets. Alternatively, the fenofibric acid and a lubricant (e.g., mineral oil in PEG) are mixed in a granulator, e.g., a fluidized bed granulator and then into tablets. Tablets are formed by standard techniques, e.g., on a (rotary) press (for example KILIAN®) fitted with suitable punches. The resulting tablets are hereinafter referred as tablet cores.

An exemplary coating process follows. Ethylcellulose and polyethylene glycol (e.g., PEG 1450) are dissolved in a solvent such as ethanol; polyvinylpyrrolidone is then added. The resulting solution is sprayed onto the tablet cores, using a coating pan or a fluidized bed apparatus.

An exemplary process for applying the second coating follows. Triethyl citrate and polyethylene glycol (e.g., PEG 1450) are dissolved in a solvent such as water; a methacrylic polymer dispersion is then added. Silicon dioxide is optionally added as a suspension. The resulting solution is sprayed onto the coated tablet cores, using a coating pan or a fluidized bed apparatus.

The weight ratio of the second coating to coated tablet core is about 1:30 to about 3:10, specifically about 1:10.

An exemplary delayed-release dosage form comprises a core containing fenofibric acid, polyvinylalcohol and glyceryl behenate; a first coating of ethylcellulose, polyvinylpyrrolidone, and polyethylene glycol; and a second coating of methacrylic acid co-polymer type C, triethyl citrate, polyethylene glycol, and optionally containing silicon dioxide.

In another embodiment, the fenofibric acid dosage form is a sustained- or extended-release dosage form. By "sustained-release" or "extended-release" are meant to include formulations designed to release the active agent at such a rate that blood (e.g., plasma) levels are maintained within a therapeutic range but below toxic levels for at least about 8 hours, specifically at least about 12 hours after administration at steady-state. The term "steady-state" means that a plateau plasma level for a given active agent has been achieved and which is maintained with subsequent doses of the drug at a level which is at or above the minimum effective therapeutic level and is below the minimum toxic plasma level for a given active agent. With regard to dissolution profiles, the first and second dissolution profiles (e.g., in the stomach and in the intestines) should each be equal to or greater than the minimum dissolution required to provide substantially equivalent bioavailability to a capsule, tablet or liquid containing the at least one active ingredient in an immediate-release form.

In one embodiment, a sustained-release fenofibric acid dosage form has a reduced $C_{max}$ compared to an immediate-release formulation comprising either fenofibric acid or fenofibrate. The sustained-release fenofibric acid dosage form can maintain bioavailability and minimum effective concentration substantially equivalent to that of the immediate release composition of fenofibrate or fenofibric acid upon multiple dosing and on a reduced frequency of dosing. In one embodiment, a sustained-release dosage form comprising fenofibric acid, when ingested orally, has a lower fluctuation index in the plasma than an immediate release composition of fenofibric acid or fenofibrate while maintaining bioavailability substantially equivalent to that of the immediate release composition of fenofibrate or fenofibric acid. As used herein, the fluctuation index or "Degree of Fluctuation (DFL)" as used herein, is expressed as: $DFL=(C_{max}-C_{min})/C_{avg}$.

The sustained-release compositions can reduce some common side effects as compared to those for the immediate-release composition.

A sustained-release form is a form suitable for providing controlled-release of the fenofibric acid over a sustained period of time (e.g., 8 hours, 12 hours, 24 hours). In one embodiment, sustained-release dosage forms of fenofibric acid release the fenofibric acid at a rate independent of pH, for example, about pH 1.2 to about 7.5. Alternatively, sustained-release dosage forms release fenofibric acid at a rate dependent upon pH, for example a lower rate of release at pH 1.2 and a higher rate of release at pH 7.5. Typically, the sustained-release form avoids "dose dumping" upon oral administration. The sustained-release oral dosage form can be formulated to provide for an increased duration of fenofibric acid action allowing once-daily dosing.

A sustained-release dosage form comprises a release-retarding material in the form of, for example, a matrix or a coating. The fenofibric acid in sustained-release form comprises, for example, a particle of the fenofibric acid that is combined with a release-retarding material. The release-retarding material is a material that permits release of the fenofibric acid at a sustained rate in an aqueous medium. The release-retarding material is selectively chosen so as to achieve, in combination with the other stated properties, a desired in vitro release rate.

Release-retarding materials include hydrophilic and/or hydrophobic polymers. Release-retarding materials include, for example acrylic polymers, alkylcelluloses, shellac, zein, hydrogenated vegetable oil, hydrogenated castor oil, and combinations comprising one or more of the foregoing materials. The oral dosage form contains about 1 wt. % to about 80 wt. % of the release-retarding material. Suitable acrylic polymers include, for example, acrylic acid and methacrylic acid copolymers, methyl methacrylate copolymers, ethoxyethyl methacrylates, cyanoethyl methacrylate, aminoalkyl methacrylate copolymer, poly(acrylic acid), poly(methacrylic acid), methacrylic acid alkylamide copolymer, poly(methyl methacrylate), poly(methacrylic acid anhydride), methyl methacrylate, polymethacrylate, poly(methyl methacrylate) copolymer, polyacrylamide, aminoalkyl methacrylate copolymer, glycidyl methacrylate copolymers, and combinations comprising one or more of the foregoing polymers. Suitable acrylic polymers include methacrylate copolymers described in NF XXIV as fully polymerized copolymers of acrylic and methacrylic acid esters with a low content of quaternary ammonium groups.

Suitable alkylcelluloses include, for example, ethylcellulose. Those skilled in the art will appreciate that other cellulosic polymers, including other alkyl cellulosic polymers, can be substituted for part or all of the ethylcellulose.

Other suitable hydrophobic materials are water-insoluble with more or less pronounced hydrophobic trends. The hydrophobic material has, for example, a melting point of about 30° C. to about 200° C., more specifically about 45° C. to about 90° C. Exemplary hydrophobic materials include natural or synthetic waxes, fatty alcohols (such as lauryl, myristyl, stearyl, cetyl or preferably cetostearyl alcohol), fatty acids, including fatty acid esters, fatty acid glycerides (mono-, di-, and tri-glycerides), hydrogenated fats, hydrocarbons, normal waxes, stearic acid, stearyl alcohol, hydrophobic and hydrophilic materials having hydrocarbon backbones, and combinations comprising one or more of the foregoing materials. Suitable waxes include beeswax, glycowax, castor wax, carnauba wax and wax-like substances, e.g., materials normally solid at room temperature and having a melting point of about 30° C. to about 100° C., and combinations comprising one or more of the foregoing waxes.

In other embodiments, the release-retarding material comprises digestible, long chain (e.g., $C_8$-$C_{50}$, specifically $C_{12}$-$C_{40}$), substituted or unsubstituted hydrocarbons, such as fatty acids, fatty alcohols, glyceryl esters of fatty acids, mineral and vegetable oils, waxes, and combinations comprising one or more of the foregoing materials. Hydrocarbons having a melting point of between about 25° C. and about 90° C. may be employed. Of these long chain hydrocarbon materials, fatty (aliphatic) alcohols are preferred. The oral dosage form comprises up to about 60 wt. % of at least one digestible, long chain hydrocarbon.

Further, the sustained-release matrix comprises up to 60 wt. % of at least one polyalkylene glycol.

Alternatively, the release-retarding material comprises polylactic acid, polyglycolic acid, or a co-polymer of lactic and glycolic acid.

Release-modifying agents, which affect the release properties of the release-retarding material, are optionally employed. The release-modifying agents function, for example, as pore-formers. The pore former can be organic or inorganic, and includes materials that can be dissolved, extracted or leached from the coating in the environment of use. Suitable pore-formers include one or more hydrophilic polymers, such as hydroxypropylmethylcellulose, hydroxypropylcellulose, polycarbonates comprised of linear polyesters of carbonic acid in which carbonate groups reoccur in the polymer chain. Alternatively, suitable pore formers include small molecules such as lactose or metal stearates, and combinations comprising one or more of the foregoing release-modifying agents.

The release-retarding material also optionally includes other additives such as an erosion-promoting agent (e.g., starch and gums); and/or a semi-permeable polymer. In addition to the above ingredients, a sustained-release dosage form optionally also contains suitable quantities of other materials, e.g., diluents, lubricants, binders, granulating aids, colorants, flavorants and glidants that are conventional in the pharmaceutical art. The release-retarding material optionally includes an exit means comprising at least one passageway, orifice, or the like. The passageway can have a suitable shape, such as round, triangular, square, elliptical, irregular, etc.

The sustained-release dosage form comprising fenofibric acid and a release-retarding material is prepared by a suitable technique for preparing fenofibric acid as described in detail below. The fenofibric acid and release-retarding material are, for example, prepared by wet granulation techniques, melt extrusion techniques, and the like. To obtain a sustained-release dosage form, it may be advantageous to incorporate an additional hydrophobic material.

The fenofibric acid in sustained-release form optionally includes a plurality of substrates comprising the fenofibric acid, which substrates are coated with a sustained-release coating comprising a release-retarding material. The sustained-release preparations may thus be made in conjunction with a multiparticulate system, such as beads, ion-exchange resin beads, spheroids, microspheres, seeds, pellets, granules, and other multiparticulate systems in order to obtain a desired sustained-release of the fenofibric acid. The multiparticulate system is presented in a capsule or other suitable unit dosage form.

In certain cases, more than one multiparticulate system can be employed, each exhibiting different characteristics, such as pH dependence of release, time for release in various media (e.g., acid, base, simulated intestinal fluid), release in vivo, size, and composition.

In some cases, a spheronizing agent, together with the fenofibric acid is spheronized to form spheroids. Microcrystalline cellulose and hydrous lactose impalpable are examples of spheronizing agents. Additionally (or alternatively), the spheroids contain a water insoluble polymer, suitably an acrylic polymer, an acrylic copolymer, such as a methacrylic acid-ethyl acrylate copolymer, or ethyl cellulose. In this formulation, the sustained-release coating will generally include a water insoluble material such as a wax, either alone or in admixture with a fatty alcohol, or shellac or zein.

Spheroids or beads, coated with fenofibric acid are prepared, for example, by dissolving or dispersing the fenofibric acid in a solvent such as water and then spraying the solution onto a substrate, for example, sugar spheres NF, 18/20 mesh, using a Wurster insert. Optionally, additional ingredients are also added prior to coating the beads in order to assist the fenofibric acid binding to the substrates, and/or to color the resulting beads, etc. The resulting substrate-fenofibric acid may optionally be overcoated with a barrier material, to separate the fenofibric acid from the next coat of material, e.g., release-retarding material. Specifically, the barrier material is a material comprising hydroxypropylmethylcellulose. However, a film-former known in the art may be used. Preferably, the barrier material does not affect the dissolution rate of the final product.

To obtain a sustained-release of the fenofibric acid in a manner sufficient to provide the desired effect for the sustained durations, the substrate comprising the fenofibric acid is coated with an amount of release-retarding material sufficient to obtain a weight gain level from about 2 to about 30 wt. %, although the coat can be greater or lesser depending upon the physical properties of the fenofibric acid and the desired release rate, among other things. Moreover, there can be more than one release-retarding material used in the coat, as well as various other pharmaceutical excipients.

In one embodiment, the release-retarding material is in the form of a film coating comprising a dispersion of a hydrophobic polymer. Solvents typically used for application of the release-retarding coating include pharmaceutically acceptable solvents, such as water, methanol, ethanol, methylene chloride, and combinations comprising one or more of the foregoing solvents.

In addition, the sustained-release profile of fenofibric acid release in the formulations (either in vivo or in vitro) can be altered, for example, by using more than one release-retarding material, varying the thickness of the release-retarding material, changing the particular release-retarding material used, altering the relative amounts of release-retarding material, altering the manner in which the plasticizer is added (e.g., when the sustained-release coating is derived from an aqueous dispersion of hydrophobic polymer), by varying the amount of plasticizer relative to retardant material, by the inclusion of additional ingredients or excipients, by altering the method of manufacture, etc.

In addition to or instead of being present in a matrix, the release-retarding agent can be in the form of a coating. Optionally, the dosage forms can be coated, or a gelatin capsule can be further coated, with a sustained-release coating such as the sustained-release coatings described herein. Such coatings are particularly useful when the subunit comprises the fenofibric acid in releasable form, but not in sustained-release form. Suitable coatings include a sufficient amount of a hydrophobic material to obtain a weight gain level from about 2 to about 30 wt. %, although the overcoat can be greater upon the physical properties of the particular the active agent and the desired release rate, among other things.

The sustained-release formulations preferably slowly release the fenofibric acid, e.g., when ingested and exposed to gastric fluids, and then to intestinal fluids. The sustained-release profile of the formulations can be altered, for example, by varying the amount of retardant, e.g., hydrophobic material, by varying the amount of plasticizer relative to hydrophobic material, by the inclusion of additional ingredients or excipients, by altering the method of manufacture, etc.

In one embodiment, a fenofibric acid dosage form is a controlled-release matrix formulation. An exemplary controlled-release formulation is one in which the fenofibric acid is dispersed in a polymeric matrix that is water-swellable rather than merely hydrophilic, that has an erosion rate that is substantially slower than its swelling rate, and that releases the fenofibric acid primarily by diffusion. The rate of diffusion of the fenofibric acid out of the matrix can be slowed by increasing the fenofibric acid particle size, by the choice of polymer used in the matrix, and/or by the choice of molecular weight of the polymer. The matrix is a relatively high molecular weight polymer that swells upon ingestion, preferably to a size that is at least about twice its unswelled volume, and that promotes gastric retention during the fed mode. Upon swelling, the matrix may also convert over a prolonged period of time from a glassy polymer to a polymer that is rubbery in consistency, or from a crystalline polymer to a rubbery one. The penetrating fluid then causes release of the fenofibric acid in a gradual and prolonged manner by the process of solution diffusion, i.e., dissolution of the fenofibric acid in the penetrating fluid and diffusion of the dissolved fenofibric acid back out of the matrix. The matrix itself is solid prior to administration and, once administered, remains undissolved in (i.e., is not eroded by) the gastric fluid for a period of time sufficient to permit substantially all of the fenofibric acid to be released by the solution diffusion process during the fed mode. By substantially all, it is meant greater than or equal to about 90 wt. %, preferably greater than or equal to about 95 wt. % of the fenofibric acid or pharmaceutically acceptable salt thereof is released. The rate-limiting factor in the release of the fenofibric acid may be therefore controlled diffusion of the fenofibric acid from the matrix rather than erosion, dissolving or chemical decomposition of the matrix.

For fenofibric acid, the swelling of the polymeric matrix thus achieves two objectives—(i) the tablet swells to a size large enough to cause it to be retained in the stomach during the fed mode, and (ii) it retards the rate of diffusion of the fenofibric acid long enough to provide multi-hour, controlled delivery of the fenofibric acid into the stomach. The water-swellable polymer forming the matrix is a polymer that is non-toxic, that swells in a dimensionally unrestricted manner upon imbibition of water, and that provides for sustained-release of an incorporated active agent. Examples of suitable polymers include, for example, cellulose polymers and their derivatives (such as for example, hydroxyethylcellulose, hydroxypropylcellulose, carboxymethylcellulose, and microcrystalline cellulose, polysaccharides and their derivatives, polyalkylene oxides, polyethylene glycols, chitosan, poly(vinyl alcohol), xanthan gum, maleic anhydride copolymers, poly(vinyl pyrrolidone), starch and starch-based polymers, poly (2-ethyl-2-oxazoline), poly(ethyleneimine), polyurethane hydrogels, crosslinked polyacrylic acids and their derivatives, and combinations comprising one or more of the foregoing polymers. Further examples are copolymers of the polymers listed in the preceding sentence, including block copolymers and grafted polymers. Specific examples of copolymers are PLURONIC® and TECTRONIC®, which are polyethylene oxide-polypropylene oxide block copolymers available from BASF Corporation, Chemicals Div., Wyandotte, Mich., USA.

The terms "cellulose" and "cellulosic" denote a linear polymer of anhydroglucose. Cellulosic polymers include, for example, alkyl-substituted cellulosic polymers that ultimately dissolve in the gastrointestinal (GI) tract in a predictably delayed manner. Alkyl-substituted cellulose derivatives may be those substituted with alkyl groups of 1 to 3 carbon atoms each. Specific examples are methylcellulose, hydroxymethylcellulose, hydroxyethylcellulose, hydroxypropylcellulose, hydroxypropylmethylcellulose, and carboxymethylcellulose. In terms of their viscosities, one class of suitable alkyl-substituted celluloses includes those whose viscosity is about 100 to about 110,000 centipoise as a 2% aqueous solution at 20° C. Another class includes those whose viscosity is about 1,000 to about 4,000 centipoise as a 1% aqueous solution at 20° C. Exemplary alkyl-substituted celluloses are hydroxyethylcellulose and hydroxypropylmethylcellulose. A specific example of a hydroxyethylcellulose is NATRASOL® 250HX NF (National Formulary), available from Aqualon Company, Wilmington, Del., USA.

Suitable polyalkylene oxides are those having the properties described above for alkyl-substituted cellulose polymers. An example of a polyalkylene oxide is poly(ethylene oxide), which term is used herein to denote a linear polymer of unsubstituted ethylene oxide. Poly(ethylene oxide) polymers having molecular weights of about 4,000,000 and higher are particularly suitable. More preferred are those with molecular weights of about 4,500,000 to about 10,000,000, and even more preferred are polymers with molecular weights of about 5,000,000 to about 8,000,000. Preferred poly(ethylene oxide)s are those with a weight-average molecular weight of about $1\times10^5$ to about $1\times10^7$, and preferably within the range of about $9\times10^5$ to about $8\times10^6$. Poly(ethylene oxide)s are often characterized by their viscosity in solution. A preferred viscosity is about 50 to about 2,000,000 centipoise for a 2% aqueous solution at 20° C. Two specific example of poly (ethylene oxide)s are POLYOX® NF, grade WSR Coagulant, molecular weight 5 million, and grade WSR 303, molecular weight 7 million, both available from Dow.

Polysaccharide gums, both natural and modified (semi-synthetic) can be used. Examples are dextran, xanthan gum, gellan gum, welan gum and rhamsan gum.

Crosslinked polyacrylic acids of greatest utility are those whose properties are the same as those described above for alkyl-substituted cellulose and polyalkylene oxide polymers. Preferred crosslinked polyacrylic acids are those with a viscosity of about 4,000 to about 40,000 centipoise for a 1% aqueous solution at 25° C. Three specific examples are CARBOPOL® NF grades 971P, 974P and 934P (BF Goodrich Co., Specialty Polymers and Chemicals Div., Cleveland, Ohio, USA).

The hydrophilicity and water swellability of these polymers cause the fenofibric acid-containing matrices to swell in size in the gastric cavity due to ingress of water in order to achieve a size that will be retained in the stomach when introduced during the fed mode. These qualities also cause the matrices to become slippery, which provides resistance to peristalsis and further promotes their retention in the stomach. The release rate of fenofibric acid from the matrix is primarily dependent upon the rate of water imbibition and the rate at which the fenofibric acid dissolves and diffuses from the swollen polymer, which in turn is related to the solubility and dissolution rate of the fenofibric acid, the fenofibric acid particle size and the fenofibric acid concentration in the matrix. Also, because these polymers dissolve very slowly in gastric fluid, the matrix maintains its physical integrity over at least a substantial period of time, in many cases at least 90%, and preferably over 100% of the dosing period. The particles will then slowly dissolve or decompose. Complete dissolution or decomposition may not occur until 24 hours or more after the intended dosing period ceases, although in most cases, complete dissolution or decomposition will occur within 10 to 24 hours after the dosing period.

The dosage forms optionally include additives that impart a small degree of hydrophobic character, to further retard the release rate of the fenofibric acid into the gastric fluid. One example of such a release rate retardant is glyceryl monostearate. Other examples are fatty acids and salts of fatty acids, one example of which is sodium myristate. The quantities of these additives when present can vary; and in most cases, the weight ratio of additive to fenofibric acid will be about 1:20 to about 1:1, and preferably about 1:8 to about 1:2.

The amount of polymer relative to the fenofibric acid can vary, depending on the fenofibric acid release rate desired and on the polymer, its molecular weight, and excipients that may be present in the formulation. The amount of polymer should be sufficient however to retain at least about 40% of the fenofibric acid within the matrix one hour after ingestion, or immersion in simulated gastric fluid. As used herein, simulated gastric fluid refers to 0.1 N hydrochloric acid. Specifically, the amount of polymer is such that at least about 50% of the fenofibric acid remains in the matrix one hour after ingestion, or immersion in simulated gastric fluid. More specifically, at least about 60%, and most preferably at least about 80%, of the fenofibric acid remains in the matrix one hour after ingestion, or immersion in simulated gastric fluid. In all cases, however, the fenofibric acid will be substantially all released from the matrix within about ten hours, and preferably within about eight hours, after ingestion or immersion in simulated gastric fluid, and the polymeric matrix will remain substantially intact until all of the fenofibric acid is released. The term "substantially intact" is used herein to denote a polymeric matrix in which the polymer portion substantially retains its size and shape without deterioration due to becoming solubilized in the gastric fluid or due to breakage into fragments or small particles.

The water-swellable polymers can be used individually or in combination. Certain combinations will often provide a more controlled-release of the fenofibric acid than their components when used individually. An exemplary combination is cellulose-based polymers combined with gums, such as hydroxyethyl cellulose or hydroxypropyl cellulose combined with xanthan gum. Another example is poly(ethylene oxide) combined with xanthan gum.

The benefits of this dosage form will be achieved over a wide range of fenofibric acid loadings, with the weight ratio of fenofibric acid to polymer of 0.01:99.99 to about 80:20. Preferred loadings (expressed in terms of the weight percent of fenofibric acid relative to total of active agent and polymer) are about 0.1% to about 10%, more preferably about 0.1% to about 5%, and most preferably in certain cases about 0.1% to about 3.5%.

The dosage forms may find their greatest utility when administered to a subject who is in the digestive state (also referred to as the postprandial or "fed" mode). The postprandial mode is distinguishable from the interdigestive (or "fasting") mode by their distinct patterns of gastroduodenal motor activity, which determine the gastric retention or gastric transit time of the stomach contents.

In one embodiment, a fenofibric acid dosage form is a pulsed-release dosage form. A "pulsed-release" formulation comprises a combination of immediate-release, sustained-release, and/or delayed-release formulations in the same dosage form. A "semi-delayed-release" formulation is a pulsed-released formulation in which a moderate dosage is provided immediately after administration and a further dosage some hours after administration. The immediate-release portion is sometimes referred to as a loading dose.

An exemplary pulsed-release dosage form provides at least a part of the dose with a pulsed delayed-release of the fenofibric acid and another part of the formulation with rapid or immediate-release. The immediate-release and delayed-release dosage forms contain the same or different amounts of fenofibric acid. In some embodiments, the delayed-release dosage form has a higher concentration of fenofibric acid than the immediate-release dosage form. The immediate and pulsed delayed-release of the drug can be achieved according to different principles, such as by single dose layered pellets or tablets, by multiple dose layered pellets or tablets, or by two or more different fractions of single or multiple dose layered pellets or tablets, optionally in combination with pellets or tablets having instant release. Multiple dose layered pellets may be filled into a capsule or together with tablet excipients compressed into a multiple unit tablet. Alternatively, a multiple dose layered tablet may be prepared.

In one embodiment, single dose layered pellets or tablets give one single delayed-release pulse of the fenofibric acid. The single dose layered pellets or tablets comprise, for example, a core material, optionally layered on a seed/sphere, the core material comprising the fenofibric acid together with a water swellable substance; a surrounding lag time controlling layer, and an outer coating layer positioned to cover the lag time controlling layer. Alternatively, the layered pellets or tablets comprise a core material comprising the fenofibric acid; a surrounding layer comprising a water swellable substance; a surrounding lag time controlling layer; and an outer coating layer positioned to cover the lag time controlling layer.

In one embodiment, multiple dose layered pellets or tablets giving two or more delayed-release pulses of the fenofibric acid comprise a core material, optionally layered on a seed/sphere comprising the fenofibric acid and a water swellable substance, a surrounding lag time controlling layer, a layer comprising the fenofibric acid optionally together with a water swellable substance; optionally a separating layer which is water-soluble or in water rapidly disintegrating; and an outer coating layer. Alternatively, multiple dose layered pellets or tablets comprise a core material, optionally layered on a seed/sphere, comprising the fenofibric acid; a surrounding layer comprising a water swellable substance; a surrounding lag time controlling layer; a layer comprising the fenofibric acid; optionally a separating layer; and an outer coating layer.

The core material comprising the fenofibric acid is prepared either by coating or layering the fenofibric acid onto a seed, such as for instance sugar spheres, or by extrusion/spheronization of a mixture comprising the fenofibric acid and pharmaceutically acceptable excipients. It is also possible to prepare the core material by using tablet technology, i.e., compression of fenofibric acid granules and optionally pharmaceutically acceptable excipients into a tablet core. For pellets of the two types, i.e., single or multiple dose pellets, which have the fenofibric acid deposited onto a seed/sphere by layering, it is also possible to have an optional layer comprising a water swellable substance beneath the fenofibric acid-containing layer in the core material. The seeds/spheres are typically water insoluble and comprise different oxides, celluloses, organic polymers and other materials, alone or in mixtures, or be water soluble and comprise different inorganic salts, sugars and other materials, alone or in mixtures. Further, the seeds/spheres may comprise the fenofibric acid in the form of crystals, agglomerates, compacts etc. The size of the seeds is about 0.1 to about 2 mm. Before the seeds are layered, the fenofibric acid is optionally mixed with further components to obtain suitable handling and processing properties and a suitable concentration of the fenofibric acid in the final mixture.

Optionally an osmotic agent is placed in the core material. Such an osmotic agent is water soluble and will provide an osmotic pressure in the tablet. Examples of osmotic agents are magnesium sulfate, sodium chloride, lithium chloride, potassium chloride, potassium sulfate, sodium carbonate, lithium sulfate, calcium bicarbonate, sodium sulfate, calcium lactate, urea, magnesium succinate, sucrose, and combinations comprising one or more of the foregoing osmotic agents.

Water swellable substances suitable for the pellet dosage forms are compounds which are able to expand when they are exposed to an aqueous solution, such as gastro-intestinal fluid. One or more water swellable substances may be present in the core material together with the fenofibric acid and optionally pharmaceutically acceptable excipient(s). Alternatively, one or more water swellable substances are included in a swelling layer applied onto the core material. As a further alternative, swellable substances(s) they may also be present in an optional swelling layer situated beneath the drug containing layer, if a layered seed or sphere is used as the core material.

The amount of water swellable substance(s) in the swelling layer or in the core to material is chosen in such a way that the core material or the swelling layer in contact with an aqueous solution, such as gastro-intestinal fluid, will expand to such a degree that the surrounding lag-time controlling membrane ruptures. A water swellable substance may also be included in the drug comprising layer of the multiple layered pellets or tablets to increase dissolution rate of the drug fraction.

Suitable water swellable substances include, for example, low-substituted hydroxypropyl cellulose, e.g., L-HPC; cross-linked polyvinyl pyrrolidone (PVP-XL), e.g., Kollidon® CL and Polyplasdone® XL; cross-linked sodium carboxymethylcellulose, e.g., Ac-di-sol®, Primellose®; sodium starch glycolate, e.g., Primojel®; sodium carboxymethylcellulose, e.g., Nymcel ZSB10®; sodium carboxymethyl starch, e.g., Explotab®; ion-exchange resins, e.g., Dowex® or Amberlite®; microcrystalline cellulose, e.g., Avicel®; starches and pregelatinized starch, e.g., Starch 1500®, Sepistab ST200®; formalin-casein, e.g., Plas-Vita®, and combinations comprising one or more of the foregoing water swellable substances.

The core optionally comprises an absorption enhancer. Suitable absorption enhancers include, for example, a fatty acid, a surfactant, a chelating agent, a bile salt, and combinations comprising one or more of the foregoing absorption enhancers. Specific examples of absorption enhancers are fatty acids such as capric acid, oleic acid and their monoglycerides, surfactants such as sodium lauryl sulfate, sodium taurocholate and polysorbate 80, chelating agents such as citric acid, phytic acid, ethylenediamine tetraacetic acid (EDTA) and ethylene glycol-bis(β-aminoethyl ether)-N,N,N,N-tetraacetic acid (EGTA). The core comprises about 0 to about 20 wt. % of the absorption enhancer based on the total weight of the core and more specifically about 2 wt. % to about 10 wt. % of the total weight of the core.

In one embodiment, the pulsed-release dosage form comprises a lag time controlling layer. A lag time controlling layer is a semipermeable membrane comprising a water resistant polymer that is semipermeable for an aqueous solution, such as gastro-intestinal fluid. Suitable polymers are cellulose acetate, ethylcellulose, polyvinyl acetate, cellulose acetate butyrate, cellulose acetate propionate, acrylic acid copolymers, such as EUDRAGIT® RS or RL, and combinations comprising one or more of the foregoing polymers. The layer optionally comprises pore forming agents, such as a water soluble substance, e.g., sucrose, salt; or a water soluble polymer e.g., polyethylene glycol. Also pharmaceutically acceptable excipients, such as fillers and membrane strength influencing agents such as talc, aerosil, and sodium aluminum silicate, may be included.

The lag time controlling layer is typically positioned nearest the inner core material and is constructed in the form of a semipermeable membrane that will disrupt after a desired time after ingestion. A desired lag time may be adjusted by the composition and thickness of the layer. The amount of substances forming such a disrupting semipermeable membrane, i.e., a lag time controlling layer, is about 0.5 to about 25 wt. % of the weight of the core material including swelling substances or a swelling layer, preferably about 2 to about 20 wt. %.

In one embodiment, the lag time controlling layer comprises a mixture of ethylcellulose and talc. The mixture contains 10 to 80 wt. % w/w of talc.

Before applying the outer coating layer onto the layered pellets or tablets, they are optionally be covered with one or more separating layers comprising excipients. The separating layer separates the composition of the layered pellets or tablets from the outer enteric coating layer. Suitable materials for the optional separating layer are pharmaceutically acceptable compounds such as, for example, sugar, polyethylene glycol, polyvinyl pyrrolidone, polyvinyl alcohol, polyvinyl acetate, hydroxypropyl cellulose, methylcellulose, ethylcellulose, hydroxypropyl methylcellulose, carboxymethylcellulose sodium and others, and combinations comprising one or more of the foregoing materials. Other additives may also be included into the separating layer.

When the optional separating layer is applied to the layered pellets or tablets, it constitutes a variable thickness. The maximum thickness of the optional separating layer is limited only by processing conditions. The separating layer may serve as a diffusion barrier and may act as a pH-buffering zone. The optional separating layer is employed to improve the chemical stability of the fenofibric acid and/or the physical properties of the dosage form.

Finally the layered pellets or tablets are covered by one or more outer coating layers by using a suitable coating technique. The outer coating layer material is dispersed or dissolved in either water or in suitable organic solvents. Suitable polymers for the coating material include methacrylic acid copolymers, cellulose acetate phthalate, hydroxypropyl methylcellulose phthalate, hydroxypropyl methylcellulose acetate succinate, polyvinyl acetate phthalate, cellulose acetate trimellitate, carboxymethyl ethylcellulose, shellac or other suitable coating layer polymer(s), and combinations comprising one or more of the foregoing polymers.

The applied polymer containing layers, specifically the outer coating layers, optionally contain pharmaceutically acceptable plasticizers to obtain desired mechanical properties.

In one embodiment, the fenofibric acid dosage form is a wax formulation. A wax formulation is a solid dosage form comprising the fenofibric acid or a pharmaceutically acceptable salt thereof, in a waxy matrix. The waxy matrix is prepared, for example, by hot melting a suitable wax material and using the melt to granulate the fenofibric acid. The matrix material comprises the waxy material and the fenofibric acid.

Suitable wax materials include, for example, an amorphous wax, an anionic wax, an anionic emulsifying wax, a bleached wax, a carnauba wax, a cetyl esters wax, a beeswax, a castor wax, a cationic emulsifying wax, a cetrimide emulsifying wax, an emulsifying wax, a glyceryl behenate, a microcrystalline wax, a nonionic wax, a nonionic emulsifying wax, a paraffin, a petroleum wax, a spermaceti wax, a white wax, a yellow wax, and combinations comprising one or more of the foregoing waxes. These and other suitable waxes are known to those of skill in the art. A cetyl esters wax, for example, typically has a molecular weight of about 470 to about 490 and is a mixture containing primarily esters of saturated fatty alcohols and saturated fatty acids. The wax material can comprise a carnauba wax, glyceryl behenates, castor wax, and combinations comprising one or more of the foregoing waxes. When the waxy material consists of carnauba wax and no other waxy material is used, the matrix is optionally coated with a functional coating. When the waxy material includes glyceryl behenates and carnauba wax, the matrix can be used without a coating, but may have either a cosmetic coating or a functional coating depending on the precise release profile and appearance desired.

The wax material is employed at about 16 wt. % to about 35 wt. %, specifically about 20 wt. % to about 32 wt. %, more specifically about 24 wt. % to about 31 wt. %, and most specifically about 28 wt. % to about 29 wt. % of the total weight of the matrix material. When a combination of wax is used, e.g., carnauba wax and glyceryl behenate, the component waxes can be used in a suitable ratio. Certain formulations include the wax material component from 100 to about 85 parts carnauba wax and from 0 to about 15 parts glyceryl behenate. In formulations that have a combination of carnauba wax and castor wax, for example, the wax component comprises, for example, about 100 to about 85 parts carnauba wax and 0 to about 15 parts castor wax. When carnauba wax, glyceryl behenate and castor wax are present, the carnauba wax comprises at least about 85 wt. % of the waxy material and the balance of the waxy material is made up of a combination of glyceryl behenate and castor wax, in a suitable relative proportion.

Optionally, fatty acids and fatty acid soaps can be present in the wax dosage form. In some cases, the fatty acids and/or fatty acid soaps replace a portion of the wax or waxes. These optional fatty acids and fatty acid soaps include those that are generally used in the pharmaceutical industry as tableting lubricants, such as, for example, solid fatty acids (for example fatty acids having from about 16 to about 22 carbon atoms), and the alkaline earth metal salts thereof, particularly the magnesium and calcium salts, and combinations comprising one or more of the foregoing fatty acids. The fatty acid can be, for example, stearic acid. The optional fatty acids and fatty acid soaps, when present, are used in amounts of up to about 10 wt. % of the total weight of the matrix material, or about 2.5 wt. % to about 9 wt. %, or about 2.7 wt. % to about 8.6 wt. %, or about 3 wt. % to about 6 wt. % of the total weight of the matrix material. An amount of up to about 2 wt. % of the total core formulation of the optional fatty acid materials may be used as a blend with the melt granulate. Amounts of at least about 1% may be used in this fashion with the remainder being added to the waxes for melting and granulating the fenofibric acid.

To prepare the dosage form, the waxes are melted and used to granulate the fenofibric acid. The granulate is allowed to cool and then milled to a proper size. Advantageously, the granulate is milled to an average particle size of about 75 microns to about 850 microns, specifically about 150 microns to about 425 microns. The milled granulate is optionally mixed with processing aids. The processing aids include, for example, hydrophobic colloidal silicon dioxide (such as CAB-O-SIL® M5). Hydrophobic silicon dioxide is typically employed in amounts of less than or equal to about 0.5 wt. %, but individual formulations can be varied as required. The blend of the waxy granulate and the processing aids, if any, are compressed and then optionally coated.

The wax dosage form can include, for example, compressed coated or uncoated tablets, compressed pellets contained in capsules, or loose powder or powder filled capsules.

In one embodiment, a fenofibric acid dosage form comprises a gum such as a polysaccharide gum to produce a sustained-release of the fenofibric acid. Polysaccharide gums, both natural and modified (semi-synthetic) can be used. Examples are dextran, xanthan gum, gellan gum, welan gum and rhamsan gum. The gum is present, for example, in the form of a matrix comprising 10 to 80 wt. % of the formulation, specifically 20 to 60 wt. %.

In one embodiment, a fenofibric acid dosage form is a bioadhesive dosage form designed to adhere to the epithelial surface of the stomach. Bioadhesive dosage forms comprise a bioadhesive polymer and additional excipients for the release of the fenofibric acid to the stomach. Bioadhesive dosage forms can be tablets, capsules or granules comprising a bioadhesive polymer.

Suitable bioadhesive polymers include carbomer, polycarbophil, hydrodroxypropyl methyl cellulose, hydroxypropyl cellulose or admixtures thereof. Cationic bioadhesive polymers include acidic (high isoelectric point) gelatin; polygalactosamine; proteins (polyaminoacids) such as polylysine, polyomithine; polyquaternary compounds; prolamine; polyimine; diethylaminoethyldextran (DEAE); DEAE-imine; polyvinylpyridine; polythiodiethylaminomethylethylene (PTDAE); polyhistidine; DEAE-methacrylate; DEAE-acrylamide; poly-p-aminostyrene; polyoxethane; copolymethacrylates (e.g. copolymers of HPMA, N-(2-hydroxypropyl)-methacrylamide); EUDRAGIT® RL; EUDRAGIT® RS; polyamidoamines; cationic starches; DEAE-dextran; DEAE-cellulose; and combinations comprising one or more of the foregoing polymers.

In another embodiment, a fenofibric acid dosage form dosage form is a chewable tablet containing the fenofibric acid. A chewable tablet comprises a chewable base and optionally a sweetener. The chewable base comprises an excipient such as, for example, mannitol, sorbitol, lactose, or a combination comprising one or more of the foregoing excipients. The optional sweetener used in the chewable dosage form includes, for example, digestible sugars, sucrose, liquid glucose, sorbitol, dextrose, isomalt, liquid maltitol, aspartame, lactose, and combinations comprising one or more of the foregoing sweeteners. In certain cases, the chewable base and the sweetener are the same component. The chewable base and optional sweetener comprise about 50 to about 90 wt. % of the total weight of the dosage form.

The chewable dosage form optionally additionally contains preservatives, agents that prevent adhesion to oral cavity and crystallization of sugars, flavoring agents, souring agents, coloring agents, and combinations comprising one or more of the foregoing agents. Glycerin, lecithin, hydrogenated palm oil or glyceryl monostearate may be used as a protecting agent of crystallization of the sugars in an amount of about 0.04 to about 2.0 wt. % of the total weight of the ingredients, to prevent adhesion to oral cavity and improve the soft property of the products. Additionally, isomalt or liquid maltitol may be used to enhance the chewing properties of the chewable dosage form.

A method of making a chewable dosage form of the fenofibric acid is similar to the method used to make soft confectionary. The method generally involves the formation of a digestible sugar blend to which is added a frappe mixture. The boiled sugar blend is prepared, for example, from sugar and corn syrup blended in parts by weight ratio of 90:10 to 10:90. This blend is heated to temperatures above 250° F. to remove water and to form a molten mass. The frappe mixture is prepared from gelatin, egg albumen, milk proteins such as casein, and vegetable proteins such as soy protein, and the like which are added to a gelatin solution and rapidly mixed at ambient temperature to form an aerated sponge like mass. The frappe mixture is then added to the molten candy base and mixed until homogenous at temperatures between 150° F. to about 250° F. A wax matrix containing the fenofibric acid is added as the temperature of the mix is lowered to about 120° F. to about 194° F., whereupon additional ingredients such as flavors, colorants, and preservatives are added. The formulation is further cooled and formed to pieces of desired dimensions.

In another embodiment, an oral dosage form comprises a non-chewable, fast dissolving dosage form of the fenofibric acid. These dosage forms are made by methods known to those of ordinary skill in the art of pharmaceutical formulations. For example, Cima Labs has produced oral dosage forms including microparticles and effervescents that rapidly disintegrate in the mouth and provide adequate taste-masking. Zydis (ZYPREXA®) is produced by Eli Lilly as in a rapidly dissolvable, freeze-dried, sugar matrix formulated as a rapidly dissolving tablet. U.S. Pat. No. 5,178,878 and U.S. Pat. No. 6,221,392 provide teachings regarding fast-dissolve dosage forms, and are incorporated by reference.

An exemplary fast dissolve dosage form includes a mixture incorporating a water and/or saliva activated effervescent disintegration agent and microparticles. The microparticles incorporate fenofibric acid together with a protective material substantially encompassing the fenofibric acid. The term "substantially encompassing" as used in this context means that the protective material substantially shields the fenofibric acid from contact with the environment outside of the microparticle. Thus, each microparticle incorporates a discrete mass of the fenofibric acid covered by a coating of the protective material, in which case the microparticle can be referred to as a "microcapsule". Alternatively or additionally, each microparticle has the fenofibric acid dispersed or dissolved in a matrix of the protective material. The mixture including the microparticles and effervescent agent is present as a tablet of a size and shape adapted for direct oral administration to a patient, such as a human patient. The tablet is substantially completely disintegrable upon exposure to water and/or saliva. The effervescent disintegration agent is present in an amount effective to aid in disintegration of the tablet, and to provide a distinct sensation of effervescence when the tablet is placed in the mouth of a patient.

The effervescent sensation is not only pleasant to the patient but also tends to stimulate saliva production, thereby providing additional water to aid in further effervescent action. Thus, once the tablet is placed in the patient's mouth, it will disintegrate rapidly and substantially completely without any voluntary action by the patient. Even if the patient does not chew the tablet, disintegration will proceed rapidly. Upon disintegration of the tablet, the microparticles are released and can be swallowed as a slurry or suspension of the microparticles. The microparticles thus may be transferred to the patient's stomach for dissolution in the digestive tract and systemic distribution of the pharmaceutical ingredient.

The term effervescent disintegration agent(s) includes compounds which evolve gas. Suitable effervescent agents evolve gas by means of chemical reactions which take place upon exposure of the effervescent disintegration agent to water and/or to saliva in the mouth. The bubble or gas generating reaction is most often the result of the reaction of a soluble acid source and an alkali metal carbonate or carbonate source. The reaction of these two general classes of compounds produces carbon dioxide gas upon contact with water included in saliva.

Such water activated materials should be kept in a generally anhydrous state with little or no absorbed moisture or in a stable hydrated form since exposure to water will prematurely disintegrate the tablet. The acid sources or acid are those which are safe for human consumption and generally include food acids, acid anhydrides and acid salts. Food acids include citric acid, tartaric acid, malic acid, fumaric acid, adipic acid, succinic acid, and combinations comprising one or more of the foregoing acids. Because these acids are directly ingested, their overall solubility in water is less important than it would be if the effervescent tablet formulations were intended to be dissolved in a glass of water. Acid anhydrides of the above described acids may also be used. Acid salts include sodium, dihydrogen phosphate, disodium dihydrogen pyrophosphate, acid citrate salts, sodium acid sulfite, and combinations comprising one or more of the foregoing acid salts.

Carbonate sources include dry solid carbonate and bicarbonate salts such as sodium bicarbonate, sodium carbonate, potassium bicarbonate and potassium carbonate, magnesium carbonate and sodium sesquicarbonate, sodium glycine carbonate, L-lysine carbonate, arginine carbonate, amorphous calcium carbonate, and combinations comprising one or more of the foregoing carbonates.

The effervescent disintegration agent is not always based upon a reaction which forms carbon dioxide. Reactants which evolve oxygen or other gasses which are pediatrically safe may also be employed. Where the effervescent agent includes two mutually reactive components, such as an acid source and a carbonate source, it is preferred that both components react substantially completely. Therefore, an equivalent ratio of components which provides for equal equivalents is preferred. For example, if the acid used is diprotic, then either twice the amount of a mono-reactive carbonate base, or an equal amount of a di-reactive base should be used for complete neutralization to be realized. However, the amount of either acid or carbonate source may exceed the amount of the other component. This may be useful to enhance taste and/or performance of a tablet containing an overage of either component. In this case, it is acceptable that the additional amount of either component may remain unreacted.

In general, the amount of effervescent disintegration agent useful for the formation of tablets is about 5 to about 50 wt. % of the final composition, specifically about 15 and about 30 wt. %, and most specifically about 20 and about 25 wt. %.

More specifically, the tablets should contain an amount of effervescent disintegration agent effective to aid in the rapid and complete disintegration of the tablet when orally administered. By "rapid", it is understood that the tablets should disintegrate in the mouth of a patient in less than about 10 minutes, and desirably between about 30 seconds and about 7 minutes, preferably tablet should dissolve in the mouth in between about 30 seconds and about 5 minutes. Disintegration time in the mouth can be measured by observing the disintegration time of the tablet in water at about 37° C. The tablet is immersed in the water without forcible agitation. The disintegration time is the time from immersion for substantially complete dispersion of the tablet as determined by visual observation. As used herein, the term "complete disintegration" of the tablet does not require dissolution or disintegration of the microcapsules or other discrete inclusions.

The fenofibric acid in the dosage form is optionally present in microparticles. Each microparticle incorporates the fenofibric acid in conjunction with a protective material. The microparticle may be provided as a microcapsule or as a matrix-type microparticle. Microcapsules may incorporate a discrete mass of the fenofibric acid surrounded by a discrete, separately observable coating of the protective material. Conversely, in a matrix-type particle, the fenofibric acid is dissolved, suspended or otherwise dispersed throughout the protective material. Certain microparticles include attributes of both microcapsules and matrix-type particle. For example, a microparticle may incorporate a core incorporating a dispersion of the fenofibric acid in a first protective material and a coating of a second protective material, which is the same as or different from the first protective material surrounding the core. Alternatively, a microparticle incorporates a core consisting essentially of the fenofibric acid and a coating incorporating the protective material, the coating itself having some of the pharmaceutical ingredient dispersed within it.

The microparticles are about 75 to 600 microns mean outside diameter, and more preferably about 150 to about 500 microns. Microparticles above about 200 microns may be employed. Thus, the microparticles are about 200 mesh to about 30 mesh U.S. standard size, and more specifically about 100 mesh to about 35 mesh.

Tablets can be manufactured by well-known tableting procedures. In common tableting processes, the material which is to be tableted is deposited into a cavity, and one or more punch members are then advanced into the cavity and brought into intimate contact with the material to be pressed, whereupon compressive force is applied. The material is thus forced into conformity with the shape of the punches and the cavity. Hundreds, and even thousands, of tablets per minute can be produced in this fashion.

Another exemplary fast-dissolve dosage form is a hard, compressed, rapidly dissolvable dosage form adapted for direct oral dosing. The dosage form includes fenofibric acid often in the form of a protected particle, and a matrix. The matrix includes a nondirect compression filler and a lubricant, although, it may include other ingredients as well. The dosage form is adapted to rapidly dissolve in the mouth of a patient, yet it has a friability of about 2% or less when tested according to the U.S.P. Generally, the dosage form will also have a hardness of at least about 15-2 Newtons (1.5-2.0 kilopond (kp)). Not only does the dosage form dissolve quickly, it does so in a way that provides a positive organoleptic sensation to the patient. In particular, the dosage form dissolves with a minimum of unpleasant grit which is tactilely inconsistent with a positive organoleptic sensation to the patient.

Suitable protective materials include polymers utilized in the formation of microparticles, matrix-type microparticles and microcapsules. Among these polymers are cellulosic materials such as naturally occurring cellulose and synthetic cellulose derivatives; acrylic polymers; and vinyl polymers. Other suitable polymers include proteinaceous materials such as gelatin, polypeptides and natural and synthetic shellacs and waxes. Protective polymers also include ethylcellulose, methylcellulose, carboxymethyl cellulose and acrylic resin material sold under the registered trademark EUDRAGIT® by Rohm Pharma GmbH of Darmstadt, Germany.

Generally, when a coating is used, the coating comprises greater than or equal to about 5 wt. % based on the weight of the resulting particles. More specifically, the coating constitutes at least about 10 wt. % by weight of the particle. The upper limit of protective coating material used is generally less critical, except that where a rapid release of the active ingredient is desired, the amount of coating material should not be so great that the coating material impedes the release profile of the fenofibric acid when ingested. Thus, it may be possible to use greater than 100 percent of the weight of the core, thereby providing a relatively thick coating.

Suitable fillers include nondirect compression fillers. Exemplary fillers include, for example, nondirect compression sugars and sugar alcohols. Such sugars and sugar alcohols include, without limitation, dextrose, mannitol, sorbitol, lactose and sucrose. Of course, dextrose, for example, can exist as either a direct compression sugar, i.e., a sugar which has been modified to increase its compressibility, or a nondirect compression sugar.

Generally, the balance of the formulation is the matrix. Thus the percentage of filler can approach 100% by weight. However, generally, the amount of nondirect compression filler is about 25 to about 95 wt. %, specifically about 50 to about 95 wt. % and more specifically about 60 to about 95 wt. % of the total weight of the dosage form.

In the fast-dissolve dosage form, a relatively high proportion of lubricant may be employed. Lubricants, and in particular, hydrophobic lubricants such as magnesium stearate, are generally used in an amount of about 0.25 to about 5 wt. %, according to the Handbook of Pharmaceutical Excipients. Specifically, the amount of lubricant used can be about 1 to about 2.5 wt. %, and more preferably about 1.5 to about 2 wt. %. Despite the use of this relatively high rate of lubricant, the formulations exhibit a superior compressibility, hardness, and rapid dissolution within the mouth.

Hydrophobic lubricants include, for example, alkaline stearates, stearic acid, mineral and vegetable oils, glyceryl behenate, sodium stearyl fumarate, and combinations comprising one or more of the foregoing lubricants. Hydrophilic lubricants can also be used.

The hard, compressed dosage forms have a hardness of at least about 15 Newtons and are designed to dissolve spontaneously and rapidly in the mouth of a patient in less than about 90 seconds to thereby liberate the particles. Preferably the dosage form will dissolve in less than about 60 seconds and even more preferably about 45 seconds. This measure of hardness is based on the use of small tablets of less than about 0.25 inches in diameter. A hardness of at least about 20 Newtons is preferred for larger tablets. Direct compression techniques are preferred for the formation of the tablets.

In one embodiment, the fenofibric acid dosage form comprises a taste-masked dosage form. The taste-masked dosage forms may be liquid dosage forms such as those disclosed in U.S. Pat. No. 6,197,348, incorporated herein by reference.

In one embodiment, a solid taste masked dosage form comprises a core element comprising the fenofibric acid and a coating surrounding the core element. The core element comprising the fenofibric acid is in the form of a capsule or is encapsulated by micro-encapsulation techniques, where a polymeric coating is applied to the formulation. The core element includes the fenofibric acid and optionally also includes carriers or excipients, fillers, flavoring agents, stabilizing agents and/or colorants.

The taste masked dosage form may include about 77 wt. % to about 100 wt. %, specifically about 80 wt. % to about 90 wt. %, based on the total weight of the composition of the core element including the fenofibric acid; and about 20 wt. % to about 70 wt. %, of a substantially continuous coating on the core element formed from a coating material including a polymer. The core element includes about 52 wt. % to about 85 wt. % of the fenofibric acid; and about 5 wt. % to about 25 wt. % of a supplementary component selected from waxes, water insoluble polymers, enteric polymers, and partially water soluble polymers, other suitable pharmaceutical excipients, and combinations comprising one or more of the foregoing components.

The core element optionally includes carriers or excipients, fillers, flavoring agents, stabilizing agents, colorants, and combinations comprising one or more of the foregoing additives. Suitable fillers include, for example, insoluble materials such as silicon dioxide, titanium dioxide, talc, alumina, starch, kaolin, polacrilin potassium, powdered cellulose, and microcrystalline cellulose, and combinations comprising one or more of the foregoing fillers. Soluble fillers include, for example, mannitol, sucrose, lactose, dextrose, sodium chloride, sorbitol, and combinations comprising one or more of the foregoing fillers. The filler may be present in amounts of up to about 75 wt. % based on the total weight of the composition. The particles of the core element may be in the range of the particle size set forth above for core particles of core elements.

The core element is optionally in the form of a powder, for example, having particle sizes of about 35 µm to about 125 µm. The small particle size facilitates a substantially non-gritty feel in the mouth. Small particle size also minimizes break-up of the particles in the mouth, e.g., by the teeth. When in the form of a powder, the taste masked dosage form may be administered directly into the mouth or mixed with a carrier such as water, or semi-liquid compositions such as syrups, yogurt, and the like. However, the taste masked fenofibric acid may be provided in any suitable unit dosage form.

The coating material of the taste-masked formulation may take a form that provides a substantially continuous coating and still provides taste masking. In some cases, the coating also provides controlled-release of the fenofibric acid. The polymer used in taste masked dosage form coating may be a water insoluble polymer such as, for example, ethyl cellulose. The coating material of the taste masked dosage form may further include a plasticizer.

A method of preparing taste-masked pharmaceutical formulations such as powdered formulations includes mixing a core element and a coating material in a diluent and spray drying the mixture to form a taste-masked formulation. Spray drying of the fenofibric acid and polymer in the solvent involves spraying a stream of air into an atomized suspension so that solvent is caused to evaporate leaving the fenofibric acid coated with the polymer coating material.

For a solvent such as methylene chloride, the solvent concentration in the drying chamber is typically maintained above about 40,000 parts, or about 40,000 to about 100,000 parts per million of organic solvent. The spray-drying process for such solvents is conducted at a process temperature of about 5° C. to about 35° C. Spray drying of the dosage forms is undertaken, for example, utilizing either rotary, pneumatic or pressure atomizers located in either a co-current, counter-current or mixed-flow spray dryer or variations thereof. The drying gas is optionally heated or cooled to control the rate of drying. A temperature below the boiling point of the solvent may be used. Inlet temperatures are about 40° C. to about 120° C. and outlet temperatures about 5° C. to about 35° C.

The coat formation may be optimized to meet the needs of the material or application. Controlling the process parameters including temperature, solvent concentration, spray dryer capacity, atomizing air pressure, droplet size, viscosity, total air pressure in the system and solvent system, allows the formation of a range of coats, ranging from dense, continuous, non-porous coats through to more porous microcapsule/polymer matrices.

An optional post-treatment step is used to remove residual solvent. The post treatment may include a post drying step including drying the final product on a tray and drying the product at a bed temperature sufficient to remove excess solvent, but not degrade the fenofibric acid. Preferably the drying temperature is about 35° C. to about 4° C. Once completed, the product may be collected by a suitable method, such as collection by sock filters or cyclone collection.

In one embodiment, liquid dosage forms of the fenofibric acid may be formulated that also provide adequate taste masking. A taste masked liquid dosage form comprises, for example, a suspension of microcapsules taste masked as a function of the pH of a suspending medium and a polymer coating. Many active agents are less soluble at higher or lower pH than at the pH value of the mouth, which is around 5.9. In these cases, the active agent is insufficiently solubilized to be tasted if the equilibrium concentration is below the taste threshold. However, problems can arise if all of the suspended particles are not swallowed because the active agent which remains in the mouth is able to dissolve at the pH of the mouth. The use of polymeric coatings on the active agent particles, which inhibit or retard the rate of dissolution and solubilization of the active agent is one means of overcoming the taste problems with delivery of active agents in suspension. The polymeric coating allows time for all of the particles to be swallowed before the taste threshold concentration is reached in the mouth.

Optimal taste masked liquid formulations are obtained when consideration is given to: (i) the pH of maximum insolubility of the active agent; (ii) the threshold concentration for taste of the active agent; (iii) the minimum buffer strength required in the medium to avoid delayed or after taste; (iv) the pH limit beyond which further increase or decrease of pH leads to unacceptable instability of the active agent; and (v) the compatibility and chemical, physical and microbial stability of the other ingredients to the pH values of the medium.

In one embodiment, a taste masked liquid dosage form comprises the fenofibric acid, a polymer with a quaternary ammonium functionality encapsulating the fenofibric acid, and a suspending medium adjusted to a pH at which the fenofibric acid remains substantially insoluble, for suspending the encapsulated fenofibric acid. The fenofibric acid is taste masked by the combination of the polymer and suspending medium.

The fenofibric acid may be in the form of its neutral or salt form and is further in the form of particles, crystals, microcapsules, granules, microgranules, powders, pellets, amorphous solids or precipitates. The particles optionally further include other functional components. The fenofibric acid may have a defined particle size distribution, specifically about 0.1 to about 500 µm, more specifically about 1 to about 250 µm, and most specifically about 10 to about 150 µm, where there is acceptable mouth feel and little chance of chewing on the residual particles and releasing the fenofibric acid to taste.

The taste masked liquid dosage form optionally includes, along with the fenofibric acid, other functional components present for the purpose of modifying the physical, chemical, or taste properties of the fenofibric acid. For example, the fenofibric acid may be in the form of ion-exchange or cyclodextrin complexes or the fenofibric acid may be included as a mixture or dispersion with various additives such as waxes, lipids, dissolution inhibitors, taste-masking or -suppressing agents, carriers or excipients, fillers, and combinations comprising one or more of the foregoing components.

In one embodiment, the polymer used to encapsulate the fenofibric acid or the pharmaceutical unit is a polymer having a quaternary ammonium functionality, i.e., a polymer having quaternary ammonium groups on the polymer backbone. These polymers are effective in preventing the taste perception of the fenofibric acid when the resulting microcapsules are formulated as suspensions and stored for long periods despite their widely recognized properties of being permeable to water and dissolved fenofibric acid. A suitable polymer is a copolymer of acrylic and methacrylic acid esters with quaternary ammonium groups. The polymer may be a copolymer of methyl methacrylate and triethylammonium methacrylate. Specific examples of suitable polymers include EUDRAGIT® RS and EUDRAGIT® RL, available from Röhm America, LLC, Piscataway, N.J., used individually or in combination to change the permeability of the coat. A polymer coat having a blend of the RS or RL polymer along with other pharmaceutically acceptable polymers may also be employed. The other polymers may be cellulose ethers such as ethyl cellulose, cellulose esters such as cellulose acetate and cellulose propionate, polymers that dissolve at acidic or alkaline pH, such as EUDRAGTT® E, cellulose acetate phthalate, hydroxypropylmethyl cellulose phthalate, and combinations comprising one or more of the foregoing polymers.

The quantity of polymer used in relation to the fenofibric acid is about 0.01-10:1, preferably about 0.02-1:1, more preferably about 0.03-0.5:1 and most preferably about 0.05-0.3:1 by weight.

The fenofibric acid particles are suspended, dispersed or emulsified in the suspending medium after encapsulation with the polymer. Suitable suspending media include water-based media, but may be a non-aqueous carrier as well, constituted at an optimum pH for the fenofibric acid or pharmaceutical unit, such that the fenofibric acid remains substantially insoluble. The pH and ionic strength of the medium are selected on the basis of stability, solubility and taste threshold to provide the optimum taste masking effect, and which is compatible with the stability of the fenofibric acid the polymer coat and the coating excipients.

Buffering agents are optionally included in the suspending medium for maintaining the desired pH. Suitable buffering agents include dihydrogen phosphate, hydrogen phosphate, amino acids, citrate, acetate, phthalate, tartrate salts of the alkali or alkaline earth metal cations such as sodium, potassium, magnesium, calcium, and combinations comprising one or more of the foregoing buffering agents. The buffering agents are used in a suitable combination for achieving the required pH and are typically of a buffer strength of about 0.01 to about 1 moles/liter of the final formulation, specifically about 0.01 to about 0.1 moles/liter, and most specifically about 0.02 to about 0.05 moles/liter.

The taste masked liquid dosage form optionally further includes other optional dissolved or suspended agents to provide stability to the suspension. These agents include suspending agents or stabilizers such as, for example, methyl cellulose, sodium alginate, xanthan gum, (poly)vinyl alcohol, microcrystalline cellulose, colloidal silicas, bentonite clay, and combinations comprising one or more of the foregoing agents. Other agents used include preservatives such as methyl, ethyl, propyl and butyl parabens, sweeteners such as saccharin sodium, aspartame, mannitol, flavorings such as grape, cherry, peppermint, menthol and vanilla flavors, and antioxidants or other stabilizers, and combinations comprising one or more of the foregoing agents.

A method of preparing a taste masked dosage form for oral delivery, comprises encapsulating the fenofibric acid with a polymer having a quaternary ammonium functionality; and adding a suspending medium adjusted to a pH at which the fenofibric acid is substantially insoluble, for suspending the encapsulated fenofibric acid; wherein the fenofibric acid is taste masked by the combination of the polymer and the medium. In the process, the polymer for encapsulation of the fenofibric acid or fenofibric acid-containing particle is dissolved in a solution or solvent chosen for its poor solubility for the fenofibric acid and good solubility for the polymer. Examples of appropriate solvents include but are not limited to methanol, ethanol, isopropanol, chloroform, methylene chloride, cyclohexane, and toluene, either used in combination or used alone. Aqueous dispersions of polymers may also be used for forming the fenofibric acid microparticles.

Encapsulation of the fenofibric acid or pharmaceutical unit by the polymer may be performed by a method such as suspending, dissolving, or dispersing the fenofibric acid in a solution or dispersion of polymer coating material and spray drying, fluid-bed coating, simple or complex coacervation, coevaporation, co-grinding, melt dispersion and emulsion-solvent evaporation techniques, and the like.

The polymer coated fenofibric acid powder can also be employed as an alternative be applied for the preparation of reconstitutable powders, i.e.; dry powder fenofibric acid products that are reconstituted as suspensions in a liquid vehicle such as water before usage. The reconstitutable powders have a long shelf life and the suspensions, once reconstituted, have adequate taste masking.

In one embodiment, the fenofibric acid dosage form is a sprinkle dosage form. Sprinkle dosage forms include particulate or pelletized forms of the fenofibric acid, optionally having functional or non-functional coatings, with which a patient or a caregiver can sprinkle the particulate/pelletized dose into drink or onto soft food. A sprinkle dosage form comprises particles of about 10 to about 100 micrometers in their major dimension. Sprinkle dosage forms are in the form of optionally coated granules or as microcapsules. Sprinkle dosage forms may be immediate or controlled-release formulations such as sustained-release formulations. See U.S. Pat. No. 5,084,278, which is hereby incorporated by reference for its teachings regarding microcapsule formulations, which may be administered as sprinkle dosage forms.

In one embodiment, a fenofibric acid dosage form is suitable for buccal or sublingual delivery. For delivery to the buccal or sublingual membranes, an oral formulation, such as a lozenge, tablet, or capsule, is employed. The method of manufacture of these formulations is known in the art, including, but not limited to, the addition of the fenofibric acid to a pre-manufactured tablet; cold compression of an inert filler, a binder, and either a pharmacological agent or a substance containing the agent (as described, for example, in U.S. Pat. No. 4,806,356, incorporated herein by reference); and encapsulation. Another oral formulation is one that can be applied with an adhesive, such as the cellulose derivative hydroxypropyl cellulose, to the oral mucosa, for example as described in U.S. Pat. No. 4,940,587, incorporated herein by reference. This buccal adhesive formulation, when applied to the buccal mucosa, allows for controlled release of the pharmacological agent into the mouth and through the buccal mucosa.

In another embodiment, a fenofibric acid dosage form comprises a zero order release dosage form. In zero order release, the amount of drug release remains constant with respect to time. Suitable methods for preparing zero order controlled release dosage forms include those operating by a rate-controlling membrane and by osmotic pumps, and wax matrix dosage forms, optionally comprising a coating.

In another embodiment, a fenofibric acid dosage form is an "osmotic pump" dosage form such as one formulated with OROS® technology (Alza Corporation, Mountain View, Calif.). Such dosage forms have a fluid-permeable (semipermeable) membrane wall, an osmotically active expandable driving member (the osmotic push layer), and a density element for delivering the fenofibric acid. In an osmotic pump dosage form, the active material is dispensed through an exit means comprising a passageway, orifice, or the like, by the action of the osmotically active driving member. The fenofibric acid of the osmotic pump dosage form is, for example, formulated as a thermo-responsive formulation in which the fenofibric acid is dispersed in a thermo-responsive composition. Alternatively, the osmotic pump dosage form contains a thermo-responsive element comprising a thermo-responsive composition at the interface of the osmotic push layer and the fenofibric acid composition.

The osmotic pump dosage form comprises a semipermeable membrane. The capsule or other dispenser of the osmotic pump dosage form can be provided with an outer wall comprising the selectively semipermeable material. A selectively permeable material is one that does not adversely affect a host or animal, is permeable to the passage of an external aqueous fluid, such as water or biological fluids, while remaining essentially impermeable to the passage of the fenofibric acid, and maintains its integrity in the presence of a thermotropic thermo-responsive composition, that is it does not melt or erode in its presence. The selectively semipermeable material forming the outer wall is substantially insoluble in body fluids, nontoxic, and non-erodible.

Representative materials for forming the selectively semipermeable wall include semipermeable homopolymers, semipermeable copolymers, and the like. Suitable materials include, for example, cellulose esters, cellulose monoesters, cellulose diesters, cellulose triesters, cellulose ethers, cellulose ester-ethers, and combinations comprising one or more of the foregoing materials. These cellulosic polymers have a degree of substitution, D.S., on their anhydroglucose unit from greater than 0 up to 3 inclusive. By degree of substitution is meant the average number of hydroxyl groups originally present on the anhydroglucose unit that are replaced by a substituting group, or converted into another group. The anhydroglucose unit can be partially or completely substituted with groups such as acyl, alkanoyl, aroyl, alkyl, alkenyl, alkoxy, halogen, carboalkyl, alkylcarbamate, alkylcarbonate, alkylsulfonate, alkylsulfamate, and like semipermeable polymer forming groups.

Other selectively semipermeable materials include, for example, cellulose acylate, cellulose diacylate, cellulose triacylate, cellulose acetate, cellulose diacetate, cellulose triacetate, mono-, di- and tri-cellulose alkanylates, mono-, di- and tri-alkenylates, mono-, di- and tri-aroylates, and the like, and combinations comprising one or more of the foregoing materials. Exemplary polymers including cellulose acetate having a D.S. of 1.8 to 2.3 and an acetyl content of about 32 to about 39.9%; cellulose diacetate having a D.S. of 1 to 2 and an acetyl content of about 21 to about 35%; cellulose triacetate having a D.S of 2 to 3 and an acetyl content of about 34 to about 44.8%, and the like. More specific cellulosic polymers include cellulose propionate having a D.S. of 1.8 and a propionyl content of about 38.5%; cellulose acetate propionate having an acetyl content of about 1.5 to about 7% and an propionyl content of about 39 to about 42%; cellulose acetate propionate having an acetyl content of about 2.5 to about 3%, an average propionyl content of about 39.2 to about 45% and a hydroxyl content of about 2.8 to about 5.4%; cellulose acetate butyrate having a D.S. of 1.8, an acetyl content of about 13 to about 15%, and a butyryl content of about 34 to about 39%; cellulose acetate butyrate having an acetyl content of about 2 to about 29.5%, a butyryl content of about 17 to about 53%, and a hydroxyl content of about 0.5 to about 4.7%; cellulose triacylates having a D.S. of 2.9 to 3 such as cellulose trivalerate, cellulose trilaurate, cellulose tripalmitate, cellulose trioctanoate, and cellulose tripropionate; cellulose diesters having a D.S. of 2.2 to 2.6 such as cellulose disuccinate, cellulose dipalmitate, cellulose dioctanoate, cellulose dicarpylate and the like; mixed cellulose esters such as cellulose acetate valerate, cellulose acetate succinate, cellulose propionate succinate, cellulose acetate octanoate, cellulose valerate palmitate, cellulose acetate heptonate, and the like, and combinations comprising one or more of the foregoing polymers.

Additional selectively semipermeable polymers include, for example, acetaldehyde dimethyl cellulose acetate, cellulose acetate ethylcarbamate, cellulose acetate methylcarbamate, cellulose dimethylaminoacetate, semi-permeable polyamides, semipermeable polyurethanes, semi-permeable polysulfanes, semipermeable sulfonated polystyrenes, cross-linked, selectively semipermeable polymers formed by the coprecipitation of a polyanion and a polycation, selectively semipermeable silicon rubbers, semipermeable polystyrene derivates, semipermeable poly(sodium styrenesulfonate), semipermeable poly(vinylbenzyltrimethyl) ammonium chloride polymers, and combinations comprising one or more of the foregoing polymers.

The osmotically expandable driving member, or osmotic push layer, of the soft capsule osmotic pump dosage form is a swellable and expandable inner layer. The materials used for forming the osmotic push layer are neat polymeric materials and/or polymeric materials blended with osmotic agents that interact with water or a biological fluid, absorb the fluid, and swell or expand to an equilibrium state. The polymer should exhibit the ability to retain a significant fraction of imbibed fluid in the polymer molecular structure. Such polymers may be, for example, gel polymers that can swell or expand to a very high degree, usually exhibiting about a 2 to 50-fold volume increase. Swellable, hydrophilic polymers, also known as osmopolymers, can be non-cross-linked or lightly cross-linked. The cross-links can be covalent or ionic bonds with the polymer possessing the ability to swell but not dissolve in the presence of fluid. The polymer can be of plant, animal or synthetic origin. Polymeric materials useful for the present purpose include poly(hydroxyalkyl methacrylate) having a molecular weight of about 5,000 to about 5,000,000, poly(vinylpyrrolidone) having a molecular weight of about 10,000 to about 360,000, anionic and cationic hydrogels, poly(electrolyte) complexes, poly(vinyl alcohol) having a low acetate residual, a swellable mixture of agar and carboxymethyl cellulose, a swellable composition comprising methyl cellulose mixed with a sparingly crosslinked agar, a water-swellable copolymer produced by a dispersion of finely divided copolymer of maleic anhydride with styrene, ethylene, propylene, or isobutylene, water swellable polymer of N-vinyl lactams, and the like, and combinations comprising one or more of the foregoing polymers. Other gelable, fluid imbibing and retaining polymers useful for forming the osmotic push layer include pectin having a molecular weight ranging of about 30,000 to about 300,000, polysaccharides such as agar, acacia, karaya, tragacanth, algins and guar, acidic carboxy polymer and its salt derivatives, polyacrylamides, water-swellable indene maleic anhydride polymers;

polyacrylic acid having a molecular weight of about 80,000 to about 200,000; POLYOX™, polyethylene oxide polymers having a molecular weight of about 100,000 to about 5,000,000, and greater, starch graft copolymers, polyanions and polycations exchange polymers, starch-polyacrylonitrile copolymers, acrylate polymers with water absorbability of about 400 times its original weight, diesters of polyglucan, a mixture of cross-linked polyvinyl alcohol and poly(N-vinyl-2-pyrrolidone), zein available as prolamine, poly(ethylene glycol) having a molecular weight of about 4,000 to about 100,000, and the like, and combinations comprising one or more of the foregoing polymers.

The osmotically expandable driving layer of the osmotic pump dosage form may further contain an osmotically effective compound (osmagent) that can be used neat or blended homogeneously or heterogeneously with the swellable polymer, to form the osmotically expandable driving layer. Such osmagents include osmotically effective solutes that are soluble in fluid imbibed into the swellable polymer, and exhibit an osmotic pressure gradient across the semipermeable wall against an exterior fluid. Suitable osmagents include, for example, solid compounds such as magnesium sulfate, magnesium chloride, sodium chloride, lithium chloride, potassium sulfate, sodium sulfate, mannitol, urea, sorbitol, inositol, and the like, and combinations comprising one or more of the foregoing osmagents. The osmotic pressure in atmospheres, atm, of the osmagents may be greater than about zero atm, and generally about zero atm to about 500 atm, or higher.

The swellable, expandable polymer of the osmotically expandable driving layer, in addition to providing a driving source for delivering the fenofibric acid from the dosage form, may also function as a supporting matrix for an osmotically effective compound. The osmotic compound can be homogeneously or heterogeneously blended with the polymer to yield the desired expandable wall or expandable pocket. The composition in a presently preferred embodiment comprises (a) at least one polymer and at least one osmotic compound, or (b) at least one solid osmotic compound. Generally, a composition comprises about 20% to about 90% by weight of polymer and about 80% to about 10% by weight of osmotic compound, specifically about 35% to about 75% by weight of polymer and about 65% to about 25% by weight of osmotic compound.

The fenofibric acid of the osmotic pump dosage form may be formulated as a thermo-responsive formulation in which the fenofibric acid is dispersed in a thermo-responsive composition. Alternatively, the osmotic pump dosage form may contain a thermo-responsive element comprising a thermo-responsive composition at the interface of the osmotic push layer and the fenofibric acid composition. Representative thermo-responsive compositions and their melting points are as follows: Cocoa butter (32° C.-34° C.), cocoa butter plus 2% beeswax (35° C.-37° C.), propylene glycol monostearate and distearate (32° C.-35° C.), hydrogenated oils such as hydrogenated vegetable oil (36° C.-37.5° C.), 80% hydrogenated vegetable oil and 20% sorbitan monopalmitate (39° C.-39.5° C.), 80% hydrogenated vegetable oil and 20% polysorbate 60, (36° C.-37° C.), 77.5% hydrogenated vegetable oil, 20% sorbitan trioleate, 2.5% beeswax and 5.0% distilled water, (37° C.-38° C.), mono-, di-, and triglycerides of acids having from 8-22 carbon atoms including saturated and unsaturated acids such as palmitic, stearic, oleic, lineolic, linolenic and archidonic; triglycerides of saturated fatty acids with mono- and diglycerides (34° C.-35.5° C.), propylene glycol mono- and distearates 3(33° C.-34° C.), partially hydrogenated cottonseed oil (35° C.-39° C.), a block polymer of polyoxyalkylene and propylene glycol; block polymers comprising 1,2-butylene oxide to which is added ethylene oxide; block copolymers of propylene oxide and ethylene oxide, hardened fatty alcohols and fats (33° C.-36° C.), hexadienol and hydrous lanolin triethanolamine glyceryl monostearate (38° C.), eutectic mixtures of mono-, di-, and triglycerides (35° C.-39° C.), WITEPSOL®#15, triglyceride of saturated vegetable fatty acid with monoglycerides (33.5° C.-35.5° C.), WITEPSOL® H32 free of hydroxyl groups (31° C.-33° C.), WITEPSOL® W25 having a saponification value of 225-240 and a melting point of (33.5° C.-35.5° C.), WITEPSOL® E75 having a saponification value of 220-230 and a melting point of (37° C.-39° C.), a polyalkylene glycol such as polyethylene glycol 1000, a linear polymer of ethylene oxide (38° C.-41° C.), polyethylene glycol 1500 (38° C.-41° C.), polyethylene glycol monostearate (39° C.-42.5° C.), 33% polyethylene glycol 1500, 47% polyethylene glycol 6000 and 20% distilled water (39° C.-41° C.), 30% polyethylene glycol 1500, 40% polyethylene glycol 4000 and 30% polyethylene glycol 400, (33° C.-38° C.), mixture of mono-, di-, and triglycerides of saturated fatty acids having 11 to 17 carbon atoms, (33° C.-35° C.), and the like. The thermo-responsive compositions, including thermo-responsive carriers are useful for storing the fenofibric acid in a solid composition at a temperature of about 20° C. to about 33° C., maintaining an immiscible boundary at the swelling composition interface, and for dispensing the agent in a flowable composition at a temperature greater than about 33° C. and preferably between about 33° C. and about 40° C.

The amount of fenofibric acid present in the osmotic pump dosage form is about 20 mg to about 150 mg or more. The osmotic dosage form may be formulated for once daily or less frequent administration.

The fenofibric acid of the osmotic pump dosage form is formulated by a number of techniques known in the art for formulating solid and liquid oral dosage forms. The fenofibric acid of the osmotic pump dosage form may be formulated by wet granulation. In an exemplary wet granulation method, the fenofibric acid and the ingredients comprising the fenofibric acid layer are blended using an organic solvent, such as isopropyl alcohol-ethylene dichloride 80:20 v:v (volume:volume) as the granulation fluid. Other granulating fluids such as denatured alcohol 100% may be used for this purpose. The ingredients forming the fenofibric acid layer are individually passed through a screen such as a 40-mesh screen and then thoroughly blended in a mixer. Next, other ingredients comprising the fenofibric acid layer are dissolved in a portion of the granulation fluid, such as the cosolvent described above. Then the latter prepared wet blend is slowly added to the fenofibric acid blend with continual mixing in the blender. The granulating fluid is added until a wet blend is produced, which wet mass then is forced through a screen such as a 20-mesh screen onto oven trays. The blend is dried for about 18 to about 24 hours at about 30° C. to about 50° C. The dry granules are sized then with a screen such as a 20-mesh screen. Next, a lubricant is passed through a screen such as an 80-mesh screen and added to the dry screen granule blend. The granulation is put into milling jars and mixed on a jar mill for about 1 to about 15 minutes. The push layer may also be made by the same wet granulation techniques. The compositions are pressed into their individual layers in a KILIAN press-layer press.

Another manufacturing process that can be used for providing the fenofibric acid layer and osmotically expandable driving layer comprises blending the powered ingredients for each layer independently in a fluid bed granulator. After the powered ingredients are dry blended in the granulator, a granulating fluid, for example, poly(vinyl-pyrrolidone) in water, or in denatured alcohol, or in 95:5 ethyl alcohol/water, or in blends of ethanol and water is sprayed onto the powders. Optionally, the ingredients are dissolved or suspended in the granulating fluid. The coated powders are then dried in a granulator. This process granulates the ingredients present therein while adding the granulating fluid. After the granules are dried, a lubricant such as stearic acid or magnesium stearate is added to the granulator. The granules for each separate layer are pressed then in the manner described above.

The fenofibric acid formulation and osmotic push layer of the osmotic dosage form may also be manufactured by mixing fenofibric acid with composition forming ingredients and pressing the composition into a solid lamina possessing dimensions that correspond to the internal dimensions of the compartment. In another manufacture, the fenofibric acid and other fenofibric acid composition-forming ingredients and a solvent are mixed into a solid, or a semisolid, by methods such as ballmilling, calendaring, stirring or rollmilling, and then pressed into a preselected layer forming shape. Next, a layer of a composition comprising an osmopolymer and an optional osmagent are placed in contact with the layer comprising the fenofibric acid. The layering of the first layer comprising the fenofibric acid and the second layer comprising the osmopolymer and optional osmagent composition can be accomplished by using a conventional layer press technique. The semipermeable wall can be applied by molding, spraying or dipping the pressed bilayer's shapes into wall forming materials. An air suspension coating procedure which includes suspending and tumbling the two layers in current of air until the wall forming composition surrounds the layers is also used to form the semi-permeable wall of the osmotic dosage forms.

The dispenser of the osmotic pump dosage form may be in the form of a capsule. The capsule may comprise an osmotic hard capsule and/or an osmotic soft capsule. The osmotic hard capsule may be composed of two parts, a cap and a body, which are fitted together after the larger body is filled with the fenofibric acid. The osmotic hard capsule may be fitted together by slipping or telescoping the cap section over the body section, thus completely surrounding and encapsulating the fenofibric acid. Hard capsules may be made by techniques known in the art.

The soft capsule of the osmotic pump dosage form may be a one-piece osmotic soft capsule. Generally, the osmotic soft capsule is of sealed construction encapsulating the fenofibric acid. The soft capsule may be made by various processes, such as the plate process, the rotary die process, the reciprocating die process, and the continuous process.

Materials useful for forming the capsule of the osmotic pump dosage form are commercially available materials including gelatin, gelatin having a viscosity of about 5 to about 30 millipoises and a bloom strength up to about 150 grams; gelatin having a bloom value of about 160 to about 250; a composition comprising gelatin, glycerine, water and titanium dioxide; a composition comprising gelatin, erythrosin, iron oxide and titanium dioxide; a composition comprising gelatin, glycerine, sorbitol, potassium sorbate and titanium dioxide; a composition comprising gelatin, acacia, glycerin, and water; and the like, and combinations comprising one or more of the foregoing materials.

The semipermeable wall forming composition can be applied to the exterior surface of the capsule in laminar arrangement by molding, forming, air spraying, dipping or brushing with a semipermeable wall forming composition. Other techniques that can be used for applying the semipermeable wall are the air suspension procedure and the pan coating procedures. The air suspension procedure includes suspending and tumbling the capsule arrangement in a current of air and a semipermeable wall forming composition until the wall surrounds and coats the capsule. The procedure can be repeated with a different semipermeable wall forming composition to form a semipermeable laminated wall.

Exemplary solvents suitable for manufacturing the semipermeable wall include inert inorganic and organic solvents that do not adversely harm the materials, the capsule wall, the fenofibric acid, the thermo-responsive composition, the expandable member, or the final dispenser. Solvents for manufacturing the semipermeable wall may be aqueous solvents, alcohols, ketones, esters, ethers, aliphatic hydrocarbons, halogenated solvents, cycloaliphatics, aromatics, heterocyclic solvents, and combinations comprising one or more of the foregoing solvents. Particular solvents include acetone, diacetone alcohol, methanol, ethanol, isopropyl alcohol, butyl alcohol, methyl acetate, ethyl acetate, isopropyl acetate, n-butyl acetate, methyl isobutyl ketone, methyl propyl ketone, n-hexane, n-heptane, ethylene glycol monoethyl ether, ethylene glycol monoethyl acetate, methylene dichloride, ethylene dichloride, propylene dichloride, carbon tetrachloride, nitroethane, nitropropane, tetrachloroethane, ethyl ether, isopropyl ether, cyclohexane, cyclooctane, benzene, toluene, naphtha, 1,4-dioxane, tetrahydrofuran, water, and mixtures thereof such as acetone and water, acetone and methanol, acetone and ethyl alcohol, methylene dichloride and methanol, and ethylene dichloride, methanol, and combinations comprising one or more of the foregoing solvents. The semipermeable wall may be applied at a temperature a few degrees less than the melting point of the thermo-responsive composition. Alternatively, the thermo-responsive composition can be loaded into the dispenser after applying the semipermeable wall.

The exit means or hole in the osmotic pump dosage form, for releasing the fenofibric acid, can be formed by mechanical or laser drilling, or by eroding an erodible element in the wall, such as a gelatin plug. The orifice can be a polymer inserted into the semipermeable wall, which polymer is a porous polymer and has at least one pore, or which polymer is a microporous polymer and has at least one micro-pore.

In another embodiment, a fenofibric acid dosage form comprises a floating or buoyant dosage form. The principle of a floating system is that the density of floating system is lower than that of gastric fluid. Floating of the dosage form allows for extended gastric residence time of the active agent and subsequent increases in bioavailability. Floating dosage forms are hydrodynamically balanced to have a bulk density (specific gravity) of less than one in contact with gastric fluid and which, therefore, will remain floating in gastric fluid. In some embodiments, a floating dosage form can also have controlled-release properties.

In one embodiment, a floating dosage form is a sustained-release formulation comprising a homogeneous mixture of fenofibric acid with one or more hydrophillic hydrocolloids which, in contact with gastric fluid at body temperature, will form a soft gelatinous mass on the surface of the tablet, thus causing it to enlarge somewhat and acquire a bulk density (specific gravity) of less than one. Hydrocolloids suitable for use in the sustained-release formulations include one or more natural, partially or totally synthetic anionic or, preferably, nonionic hydrophillic gums, modified cellulosic substances or proteinaceous substances such as, for example, acacia, gum tragacanth, locust bean gum, guar gum, karaya gum, agar, pectin, carrageen, soluble and insoluble alginates, methylcellulose, hydroxypropylmethylcellulose, hydroxypropylcellulose, hydroxyethylcellulose, sodiumcarboxymethylcellulose, carboxypolymethylene, gelatin, casein, zein, bentonie, and the like. A preferred hydrocolloid is hydroxypropylmethylcellulose.

Edible, pharmaceutically inert, fatty materials having a specific gravity of less than one can be added to the floating formulation to decrease the hydrophillic property of the formulation and also to increase buoyancy. Examples of such materials include a purified grade of beeswax; fatty acids; long chain fatty alcohols such as, for example, cetyl alcohol, myristyl alcohol, stearyl alcohol, glycerides such as glyceryl esters of fatty acids or hydrogenated aliphatic acids such as, for example, glyceryl monostearate, glyceryl distearate, glyceryl esters of hydrogenated castor oil and the like; oils such as mineral oil and the like. The floating dosage forms may also include excipients, preservatives, stabilizers, tabletting lubricants and the like.

In one embodiment, the fenofibric acid dosage form is a liquisolid dosage form. The term "liquisolid" refers to powdered forms of liquid medications formulated by converting solutions of water-insoluble solid active agents in suitable non-volatile solvent systems, into "dry" (i.e., dry-looking), nonadherent, free-flowing and readily compressible liquid/powder admixtures by blending with selected carrier and coating materials. Liquisolid systems comprising insoluble active agents may be classified into two subgroups: "powdered active agent solutions" and "powdered active agent suspensions". These systems may be produced from the conversion of active agent solutions or suspensions into liquisolid systems. When non-volatile solvents are used to prepare the active agent solution or suspension, the liquid vehicle does not evaporate and thus, the active agent is carried within the liquid system which in turn, is dispersed throughout the final product.

The term "liquisolid compacts" refers to immediate or sustained-release tablets or capsules that are prepared using the techniques for "liquisolid systems", combined with appropriate adjuvants suitable for tabletting or encapsulation, such as lubricants, and for rapid or sustained release action, such as disintegrants or binders, respectively, and combinations comprising one or more of the forgoing additives.

Liquisolid systems are free flowing and compressible liquid/powder admixtures. A solid water-insoluble active agent such as fenofibrate is initially dissolved or suspended in a suitable non-volatile solvent system to produce an active agent solution or suspension of desired concentration. Suitable solvents include, for example, inert, high boiling point, water-miscible and not highly viscous organic solvent systems such as, for example, propylene glycol, liquid polyethylene glycols, polysorbates, glycerin, N,N-dimethylacetamide, dimethylformamide, fixed oils, and combinations comprising one or more of the foregoing solvents. The non-volatile solvent may be present in the final liquisolid dosage form in an amount of about 0.1 wt. % to about 35 wt. %. In one embodiment, the solvent comprises a mixture of one or more non-volatile solvents and one or more volatile solvents. The volatile solvent may comprise, for example, methanol, ethanol, water, acetone, methylene chloride, and combinations comprising one or more of the foregoing volatile solvents.

Next, the prepared active agent solution or suspension is incorporated into a quantity of carrier material comprising a powder substrate. Suitable carrier materials include, for example, materials of a porous nature and possessing sufficient absorption properties. Materials with a porous surface and closely matted fibers in their interior, such as powder and granular grades of microcrystalline cellulose, amorphous cellulose, hydroxypropylcellulose, polyvinylpyrrolidone, a cyclodextrin, a starch, and combinations comprising one or more of the foregoing materials are suitable carriers. The resulting wet mixture is then converted into a dry-looking, nonadherent, free-flowing and readily compressible powder by the simple addition and mixing of a calculated amount of an excipient. Suitable excipients include those possessing fine and highly adsorptive particles, such as, for example, various types of amorphous silicon dioxide (silica). Before compression or encapsulation, various adjuvants such as lubricants and disintegrants (immediate-release), binders (sustained-release), and combinations comprising one or more of the foregoing additives, may be mixed with the finished liquisolid systems to produce liquisolid compacts (tablets or capsules).

The production of liquisolid systems possessing acceptable flowability and compressibility may be addressed with a formulation-mathematical model, based on the fundamental powder properties termed flowable ($\Phi$-value) and compressible ($\Psi$-number) liquid retention potentials of the constituent powders. According to the theory, the carrier and excipients can retain certain amounts of liquid while maintaining acceptable flow and compression properties. Depending on the carrier:coating ratio (R) of the powder system used, which is the ratio between the quantities of carrier (Q) and coating (q) materials present in the formulation (R=Q/q), there is a characteristic maximum liquid load on the carrier material, termed "load factor" ($L_f$) and defined as the ratio of the amount of liquid medication (W) over the quantity of carrier material (Q) in the system ($L_f$=W/Q), which should be possessed by an acceptably flowing and compressible liquisolid system. The mathematical model for liquisolid dosage forms is described in U.S. Pat. Nos. 5,800,834; 5,968,550; 6,096,337; and 6,423,339; incorporated herein by reference.

Fenofibric acid dosage forms include liquid formulations. Liquid formulations include suspensions, solutions, syrups and elixirs. Such formulations may be employed as fillers in soft or hard capsules and typically comprise a carrier, for example, water, ethanol, polyethylene glycol, propylene glycol, methylcellulose, or a suitable oil, and one or more emulsifying agents and/or suspending agents. Liquid formulations may also be prepared by the reconstitution of a solid, for example, from a sachet.

In one embodiment, the fenofibric acid dosage form is suitable for parenteral administration. Parenteral administration is generally characterized by injection, either subcutaneously, intramuscularly, or intravenously. Thus, compositions for intravenous administration comprise a solution of fenofibric acid dissolved or suspended in an acceptable carrier. Injectables can be prepared as liquid solutions or suspensions, solid forms suitable for solution or suspension in liquid prior to injection, or as emulsions. Suitable excipients include, for example, water, buffered water, saline, dextrose, glycerol, ethanol, and the like. These compositions will be sterilized by conventional sterilization techniques, such as sterile filtration. The resulting solutions are packaged for use as is or lyophilized, the lyophilized preparation being combined with a sterile solution prior to administration. In addition, if desired, the pharmaceutical compositions to be administered may also contain minor amounts of non-toxic auxiliary substances, such as wetting or emulsifying agents, pH buffering agents and the like, such as for example, sodium acetate, sorbitan monolaurate, triethanolamine oleate, and combinations comprising one or more of the foregoing agents.

In one embodiment, the fenofibric acid is in particulate form. The fenofibric acid in particulate form comprises nanaparticulate fenofibrate, micronized fenofibric acid, or larger particles.

In one embodiment, the fenofibric acid is in micronized form. The expression "in micronized form" means a substance having "an effective average particle size of less than about 20 μm", meaning that at least 50% of the active agent particles, (e.g., fenofibric acid particles) have a particle size of less than the average, by weight. Advantageously, the effective average particle size is less than 10 μm.

The fenofibric acid is optionally micronized in the presence of a surfactant. Suitable surfactants include, for example, amphoteric, non-ionic, cationic or anionic surfactants. Examples of such surfactants are: sodium lauryl sulfate, monooleate, monolaurate, monopalmitate, monostearate or another ester of polyoxyethylene sorbitane, sodium dioctylsulfosuccinate (DOSS), lecithin, stearylic alcohol, cetostearylic alcohol, cholesterol, polyoxyethylene ricin oil, polyoxyethylene fatty acid glycerides, Poloxamer®, and combinations comprising one or more of the foregoing surfactants.

The micronized fenofibric acid optionally further comprises a hydrophilic polymer. "Hydrophilic polymer" means a high molecular weight substance (greater, for example, than 300 Da) having sufficient affinity towards water to dissolve therein and form a gel. Examples of such polymers are polyvinylpyrrolidone, poly(vinyl alcohol), hydroxypropylcellulose, hydroxymethylcellulose, hydroxypropylmethylcellulose, gelatin, and combinations comprising one or more of the foregoing polymers. The fenofibric acid can be micronized in the presence of a hydrophilic polymer, or optionally micronized and then mixed with a hydrophilic polymer.

The micronized fenofibric acid is optionally disposed on an inert hydrosoluble carrier. "Inert hydrosoluble carrier" means an excipient, generally hydrophilic, pharmaceutically inert, crystalline or amorphous, in a particulate form, not leading to a chemical reaction under the operating conditions employed, and which is soluble in an aqueous medium, notably in a gastric acid medium. Examples of such excipients are derivatives of sugars, such as lactose, saccharose, hydrolyzed starch (malto-dextrin), and combinations comprising one or more of the foregoing carriers. Mixtures are also suitable. The individual particle size of the inert hydrosoluble carrier can be, for example, between 50 and 500 microns.

In one embodiment, a micronized fenofibric acid composition is formed by spraying a suspension of fenofibric acid micronized with a hydrophilic polymer onto an inert carrier. Following granulation, the granulate formed comprises crystals of, for example, lactose, which are isolated (or possibly agglomerated together by the spray solution) and particles of active ingredient and PVP adhering to the crystal surface. The granule could similarly be constituted of coated crystals which are agglomerated, or even of such an agglomerate having received a coating.

The micronized fenofibric acid compositions can also be prepared by other methods, for example, by spraying a solution of the micronized active ingredient onto the hydrosoluble inert carrier.

The granulates thus obtained can, if desired, be provided with an outer coating or compressed into tablets, or form agglomerates.

In one embodiment, a nanoparticulate fenofibric acid composition has an average particle size of less than about 2000 nm (i.e., 2 microns), less than about 1900 nm, less than about 1800 nm, less than about 1700 nm, less than about 1600 nm, less than about 1500 nm, less than about 1400 nm, less than about 1300 nm, less than about 1200 nm, less than about 1100 nm, less than about 1000 nm, less than about 900 nm, less than about 800 nm, less than about 700 nm, less than about 600 nm, less than about 500 nm, or less than about 400 nm, as measured by light-scattering methods, microscopy, or other appropriate methods. By "an effective average particle size of less than about 2000 nm" it is meant that at least 50% of the active agent particles, (e.g., fenofibric acid particles) have a particle size of less than the average, by weight, i.e., less than about 2000 nm, 1900 nm, 1800 nm, etc., when measured by the above-noted techniques. Preferably, at least about 70%, about 90%, or about 95% of the particles have a particle size of less than the effective average, i.e., less than about 2000 nm, 1900 nm, 1800 nm, 1700 nm, etc. As is understood in the art, the value for $D_{50}$ of a nanoparticulate active agent is the particle size below which 50% of the particles fall, by weight. Similarly, $D_{90}$ is the particle size below which 90% of the fibrate particles fall, by weight.

In one embodiment, a nanoparticulate fenofibric acid dosage form comprises fenofibric acid particles and at least one surface stabilizer. Useful surface stabilizers which can be employed include, but are not limited to, nonionic, anionic, cationic, ionic, and zwitterionic surfactants. Suitable surfactants include those listed below for use in amorphous formulations.

The concentration of the fenofibric acid in the fenofibric acid nanoparticles can be about 99.5% to about 0.001%, about 95% to about 0.1%, or about 90% to about 0.5%, by weight, based on the total combined weight of the fenofibric acid and at least one surface stabilizer, not including other excipients. The concentration of the at least one surface stabilizer can be about 0.5% to about 99.999%, about 5.0% to about 99.9%, or about 10% to about 99.5%, by weight, based on the total combined dry weight of the fenofibric acid and at least one surface stabilizer, not including other excipients.

The particulate fenofibric acid compositions can be made using, for example, milling, homogenization, or precipitation techniques.

Milling fenofibric acid to obtain a nanoparticulate dispersion comprises dispersing the fenofibric acid particles in a liquid dispersion medium in which the fenofibric acid is poorly soluble, followed by applying mechanical means in the presence of grinding media to reduce the particle size of the fenofibric acid to the desired effective average particle size. The dispersion medium can be, for example, water, safflower oil, ethanol, t-butanol, glycerin, polyethylene glycol (PEG), hexane, glycol, or a combination comprising one or more of the foregoing media. In one embodiment, the dispersion medium is water.

The fenofibric acid particles can be reduced in size in the presence of at least one surface stabilizer. Alternatively, the fenofibric acid particles can be contacted with one or more surface stabilizers after attrition. Other compounds, such as a diluent, can be added to the fenofibric acid/surface stabilizer composition during the size reduction process. Dispersions can be manufactured continuously or in a batch mode.

In one embodiment, a mixture of fenofibric acid and one or more surface stabilizers is heated during the milling process. If a polymeric surface stabilizer is utilized, the temperature is raised to above the cloud point of the polymeric surface stabilizer but below the actual or depressed melting point of the fenofibric acid. The utilization of heat may be important for scale up of the milling process, as it can aid in the solubilization of the one or more active agents.

Another method of forming the desired particulate fenofibric acid composition is by microprecipitation. This is a method of preparing stable dispersions of poorly soluble active agents in the presence of one or more surface stabilizers and one or more colloid stability enhancing surface active agents free of trace toxic solvents or solubilized heavy metal impurities. Such a method comprises, for example: (1) dissolving fenofibric acid in a suitable solvent; (2) adding the formulation from step (1) to a solution comprising at least one surface stabilizer; and (3) precipitating the formulation from step (2) using an appropriate non-solvent. The method can be followed by removal of any formed salt, if present, by dialysis or diafiltration and concentration of the dispersion by conventional means.

Homogenization methods include dispersing particles of fenofibric acid, in a liquid dispersion medium, followed by subjecting the dispersion to homogenization to reduce the particle size of the fenofibric acid to the desired effective average particle size. The fenofibric acid can be reduced in size in the presence of at least one surface stabilizer. Alternatively, the fenofibric acid particles can be contacted with one or more surface stabilizers either before or after attrition. Other compounds, such as a diluent, can be added to the fenofibric acid/surface stabilizer composition either before, during, or after the size reduction process. Dispersions can be manufactured continuously or in a batch mode.

In another embodiment, the fenofibrate dosage form comprises amorphous fenofibric acid. Amorphous solids are disordered arrangements of molecules that do not possess a distinguishable crystal lattice. In one embodiment, amorphous fenofibric acid is formed by dissolving fenofibric acid in a solvent in the presence of a polymer and optionally a surfactant, and evaporating the solvent to produce amorphous fenofibrate. In one embodiment, amorphous fenofibric acid comprises fenofibric acid, a polymer and a surfactant.

In another embodiment, a spray-drying process is used to form amorphous fenofibric acid. In this embodiment, the fenofibric acid, polymer and optional surfactant are dissolved in a solvent and then sprayed in a spray-drying apparatus where the solvent is rapidly evaporated, forming solid particles of amorphous fenofibric acid. The term "spray-drying" broadly refers to processes involving breaking up liquid mixtures into small droplets (atomization) and rapidly removing solvent from the mixture in a spray-drying apparatus where there is a strong driving force for evaporation of solvent from the droplets. The strong driving force for solvent evaporation is generally provided by maintaining the partial pressure of solvent in the spray-drying apparatus well below the vapor pressure of the solvent at the temperature of the drying droplets. This is accomplished by (1) maintaining the pressure in the spray-drying apparatus at a partial vacuum (e.g., 0.01 to 0.50 atmospheres (atm); or (2) mixing the liquid droplets with a warm drying gas; or (3) both (1) and (2). In addition, at least a portion of the heat required for evaporation of solvent may be provided by heating the spray solution.

Solvents suitable for spray-drying are those in which the active agent and polymer are mutually soluble. Suitable solvents include, for example, alcohols such as methanol, ethanol, n-propanol, iso-propanol, and butanol; ketones such as acetone, methyl ethyl ketone and methyl iso-butyl ketone; esters such as ethyl acetate and propylacetate; and various other solvents such as acetonitrile, methylene chloride, toluene, THF, cyclic ethers, and 1,1,1-trichloroethane. Lower volatility solvents such as dimethyl acetamide or dimethylsulfoxide can also be used.

Suitable pharmaceutically acceptable polymers include, for example, hydroxypropyl cellulose, methyl cellulose, hydroxypropylmethyl cellulose, carboxymethyl cellulose, sodium carboxymethyl cellulose, cellulose acetate phthalate, cellulose acetate butyrate, hydroxyethyl cellulose, ethyl cellulose, polyvinyl alcohol, polypropylene, dextrans, dextrins, hydroxypropyl-beta-cyclodextrin, chitosan, co(lactic/glycolid) copolymers, poly(orthoester), poly(anhydrate), polyvinyl chloride, polyvinyl acetate, ethylene vinyl acetate, lectins, carbopols, silicon elastomers, polyacrylic polymers, maltodextrins, polyvinylpyrrolidone (PVP), polyethylene glycol (PEG), and alpha-, beta-, and gamma-cyclodextrins, and combinations comprising one or more of the foregoing polymers.

Suitable nonionic surfactants include, for example, polyoxyethylene fatty alcohol ethers (Macrogol and Brij), polyoxyethylene sorbitan fatty acid esters (Polysorbates), polyoxyethylene fatty acid esters (Myrj), sorbitan esters (Span), glycerol monostearate, polyethylene glycols, polypropylene glycols, cetyl alcohol, cetostearyl alcohol, stearyl alcohol, aryl alkyl polyether alcohols, polyoxyethylene-polyoxypropylene copolymers (poloxamers), poloxamines, methylcellulose, hydroxymethylcellulose, hydroxypropylcellulose, hydroxypropylmethylcellulose, noncrystalline cellulose, polysaccharides including starch and starch derivatives such as hydroxyethylstarch (HES), polyvinyl alcohol, polyvinylpyrrolidone, and combinations comprising one or more of the foregoing surfactants. In one embodiment, the nonionic surfactant is a polyoxyethylene and polyoxypropylene copolymer such as a block copolymer of propylene glycol and ethylene glycol.

Suitable anionic surfactants include but are not limited to alkyl sulfonates, alkyl phosphates, alkyl phosphonates, potassium laurate, triethanolamine stearate, sodium lauryl sulfate, sodium dodecylsulfate, alkyl polyoxyethylene sulfates, sodium alginate, dioctyl sodium sulfosuccinate, phosphatidyl choline, phosphatidyl glycerol, phosphatidyl inosine, phosphatidylserine, phosphatidic acid and their salts, glyceryl esters, sodium carboxymethylcellulose, cholic acid and other bile acids (e.g., cholic acid, deoxycholic acid, glycocholic acid, taurocholic acid, glycodeoxycholic acid), salts thereof (e.g., sodium deoxycholate, etc.), and combinations comprising one or more of the foregoing surfactants.

Suitable cationic surfactants include but are not limited to quaternary ammonium compounds, such as benzalkonium chloride, cetyltrimethylammonium bromide, chitosans, lauryldimethylbenzylammonium chloride, acyl camitine hydrochlorides, alkyl pyridinium halides, and combinations comprising one or more of the foregoing surfactants.

The fenofibric acid solution feed can be spray-dried under a wide variety of conditions to yield amorphous fenofibric acid. For example, various types of nozzles can be used to atomize the spray solution, thereby introducing the spray solution into the spray-dry chamber as a collection of small droplets. A suitable type of nozzle may be used to spray the solution as long as the droplets that are formed are sufficiently small that they dry sufficiently (due to evaporation of solvent) and preferably do not stick to or coat the spray-drying chamber wall.

The solution can be delivered to the spray nozzle or nozzles at a wide range of temperatures and flow rates. Generally, the solution temperature is just above the solvent's freezing point to about 20° C. above its ambient pressure boiling point (by pressurizing the solution) and in some cases even higher. Solution flow rates to the spray nozzle can vary over a wide range depending on the type of nozzle, spray-dryer size and spray-dry conditions such as the inlet temperature and flow rate of the drying gas. Generally, the energy for evaporation of solvent from the solution in a spray-drying process comes primarily from the drying gas.

The drying gas is a suitable gas, but for safety reasons, an inert gas such as nitrogen, nitrogen-enriched air or argon is preferably utilized. The drying gas is typically introduced into the drying chamber at a temperature between about 60° C. and about 300° C. and preferably between about 80° C. and about 240° C.

The large surface-to-volume ratio of the droplets and the large driving force for evaporation of solvent leads to rapid solidification times for the droplets. Solidification times should be less than about 20 seconds, less than about 10 seconds, or less than 1 second.

Following formation, the amorphous fenofibric acid can be dried to remove residual solvent using a suitable drying process, such as tray drying, fluid bed drying, microwave drying, belt drying, rotary drying, and other drying processes known in the art. The final residual solvent level may be, for example, less than 1 wt. %, preferably less than 0.1 wt. %.

Once the amorphous fenofibric acid has been formed, several processing operations can be used to facilitate incorporation of the amorphous fenofibric acid into a dosage form. These processing operations include drying, granulation, and milling.

In another embodiment, a fenofibric acid composition comprises a fenofibric acid granulate comprising fenofibric acid, a liquid surfactant and a solid, particulate filler.

A method of making a fenofibric acid granulate comprises forming a fenofibric acid solution by dissolving a quantity of fenofibric acid in a surfactant heated to a temperature sufficient to melt the fenofibric acid and form a fenofibric acid solution; dispersing the fenofibric acid solution onto solid, particulate filler, optionally in the presence of a binder to form a fenofibric acid dispersion; cooling the fenofibric acid dispersion at a temperature of less than about 15° C. to form a cooled fenofibric acid dispersion; and granulating the cooled fenofibric acid dispersion to form the fenofibric acid granulate. As used herein, a liquid surfactant is a surfactant that is liquid at ambient temperatures and a solid surfactant is a surfactant that is a solid at ambient temperatures. The surfactant can be a liquid or a solid surfactant.

In one embodiment, the ratio of fenofibric acid:surfactant is 1:1 to 10:1 on a per weight basis. A suitable liquid surfactant comprises, for example Tween 20, 40 and/or 80 (also called, polysorbate 80, or (polyoxyethylene 20 sorbitan monooleate)). Another example of the liquid surfactant is Triton X-100.

The surfactant is heated to a temperature sufficient to melt the fenofibric acid and then the fenofibric acid is added to the heated surfactant to produce a solution. Fenofibric acid has a melting temperature of about 176-180° C. Thus the surfactant and the fenofibrate are heated to a temperature of greater than 150° C.

The molten fenofibric acid and surfactant are then dispersed onto a solid, particulate binder to form dispersed fenofibric acid. Dispersion can be performed, for example, by mixing in a suitable apparatus such as a granulation apparatus, although granulation is not performed in this step. Exemplary particulate fillers include, for example, microcrystalline cellulose.

The fenofibric acid can be dispersed on the filler optionally in the presence of a binder. Suitable binders include, for example, polyvinyl pyrrolidone, hydroxypropyl cellulose, hydroxypropyl methylcellulose, methylcellulose and hydroxyethyl cellulose, sugars, starch, and combinations comprising one or more of the foregoing binders.

After the dispersed fenofibric acid is formed, the dispersed fenofibric acid is cooled at a temperature of less than or equal to about 15° C. immediately.

The cooled, dispersed fenofibric acid is then granulated to produce the fenofibric acid granulate. Suitable granulation techniques include, for example, wet granulation.

After granulation, the fenofibric acid granulate is optionally mixed with a disintegrant, a lubricant, or other excipients, and compressed into tablets. Suitable disintegrants include, for example, low-substituted hydroxypropyl cellulose, cross-linked polyvinyl pyrrolidone (PVP-XL), sodium carboxymethylcellulose, e.g., Ac-di-sol®, sodium starch glycolate, sodium carboxymethyl starch, ion-exchange resins, starch, pregelatinized starch, and combinations comprising one or more of the foregoing disintegrants. Suitable lubricants include, for example, magnesium stearate.

In another embodiment, a fenofibric acid dosage form comprises a liquid dosage form. Liquid pharmaceutically administrable compositions can, for example, be prepared by dissolving, dispersing, etc, fenofibric acid and optional pharmaceutical adjuvants in an excipient, such as, for example, water, saline, aqueous dextrose, glycerol, ethanol, olive oil, and other lipophilic solvents, and the like, to form a solution or suspension. If desired, the pharmaceutical composition to be administered may also contain minor amounts of nontoxic auxiliary substances, such as wetting or emulsifying agents, pH buffering agents, and the like, for example, sodium acetate, sorbitan monolaurate, triethanolamine sodium acetate, triethanolamine oleate, etc. Actual methods of preparing such dosage forms are known and will be apparent to those skilled in this art. The composition or formulation to be administered will contain an effective amount of an active compound of the invention.

In one embodiment, a fenofibric acid dosage form comprises an emulsion or a microemulsion. Emulsions can be as a liquid administered directly into the patient's mouth from a measuring device, or within a soft, or a hard, gelatin capsule. Alternatively, emulsions can be adsorbed onto a carrier particle such as silicon dioxide and administered as a solid, oral dosage form, such as a tablet, granules, pellets or other multiparticulates, capsules that can contain the drug in the form of minitablets, beads, or a powder.

Emulsions and microemulsions comprise an oil phase, an aqueous phase, a surfactant and optionally a co-surfactant. Microemulsions differ from (macro or coarse) emulsions in that the dispersed phase consists of globules less than 100 nanometers (nm) (0.1 micrometers) and more particularly about 30 to about 60 nm in diameter. The differences between coarse emulsions and microemulsions, however, is not only one of size of the dispersed phase. Microemulsions do not separate on standing, whereas emulsions will separate, even though this may only occur after several years.

Active agent containing water-in-oil emulsions are, for example, made by dissolving a drug in a hydrophilic phase, and then mixing the solution with an oil, and eventually with an aqueous phase. Suitable oils include, for example, mono-, di- and triglycerides, fatty acids and their esters and esters of propylene glycol or other polyols. The fatty acids and esters used as such or where they form part of a glyceride may be short chain, medium chain or long chain. The ingredients may be of vegetable or animal origin, synthetic or semisynthetic. The oils include, but are not limited to natural oils, such as cottonseed oil, soybean oil, sunflower oil; canola oil; Captex® (various grades); Miglyol®; and Myvacet®.

Suitable surfactants, include, but are not limited to, various grades of the following commercial products: Arlacel®; Tween®; Capmul®; Centrophase®; Cremophor®; Labrafac®; Labrafil®; Labrasol®; Myverol®; and Tagat®. It is often unnecessary to include a co-surfactant in the microemulsion, when the microemulsion is formulated with the appropriate choice of low-HLB and high-HLB surfactants. However, where a co-surfactant is employed, the co-surfactant is preferably selected from non-toxic short and medium chain alcohols, but is not limited to these.

In another embodiment, a fenofibric acid formulation comprises a formulation for transdermal administration. One can use topical administration to deliver fenofibric acid by percutaneous passage of the drug into the systemic circulation of the patient. The skin sites include anatomic regions for transdermally administering the drug, such as the forearm, abdomen, chest, back, buttock, and mastoidal area. The fenofibric acid is administered to the skin by placing on the skin either a topical formulation comprising the fenofibric acid or a transdermal drug delivery device that administers the fenofibric acid. In either embodiment, the delivery vehicle is designed, shaped, sized, and adapted for easy placement and comfortable retention on the skin.

A variety of transdermal drug delivery devices can be employed. For example, a simple adhesive patch comprising a backing material and an acrylate adhesive can be prepared. The fenofibric acid and any penetration enhancer can be formulated into the adhesive casting solution. The adhesive casting solution can be cast directly onto the backing material or can be applied to the skin to form an adherent coating. See, e.g., U.S. Pat. Nos. 4,310,509; 4,560,555; and 4,542,012, incorporated herein by reference.

In other embodiments, the fenofibric acid is delivered using a liquid reservoir system drug delivery device. These systems typically comprise a backing material, a membrane, an acrylate based adhesive, and a release liner. The membrane is sealed to the backing to form a reservoir. The drug or compound and any vehicles, enhancers, stabilizers, gelling agents, and the like are then incorporated into the reservoir. See, e.g., U.S. Pat. Nos. 4,597,961; 4,485,097; 4,608,249; 4,505,891; 3,843,480; 3,948,254; 3,948,262; 3,053,255; and 3,993,073; incorporated herein by reference.

Matrix patches comprising a backing, a drug/penetration enhancer matrix, a membrane, and an adhesive can also be employed to deliver fenofibric acid transdermally. The matrix material typically comprises a polyurethane foam. The active agent, any enhancers, vehicles, stabilizers, and the like are combined with the foam precursors. The foam is allowed to cure to produce a tacky, elastomeric matrix which can be directly affixed to the backing material.

Also included are preparations for topical application to the skin comprising fenofibric acid, typically in concentrations of about 0.001% to 10%, together with a non-toxic, pharmaceutically acceptable topical carrier. These topical preparations can be prepared by combining an active agent with conventional pharmaceutical diluents and carriers commonly used in topical dry, liquid, and cream formulations. Ointments and creams may, for example, be formulated with an aqueous or oily base with the addition of suitable thickening and/or gelling agents. Such bases include water and/or an oil, such as liquid paraffin or a vegetable oil, such as peanut oil or castor oil. Thickening agents include soft paraffin, aluminum stearate, cetostearyl alcohol, propylene glycol, polyethylene glycols, woolfat, hydrogenated lanolin, beeswax, and the like.

Lotions may be formulated with an aqueous or oily base and will, in general, also include one or more of the following: stabilizing agents, emulsifying agents, dispersing agents, suspending agents, thickening agents, coloring agents, perfumes, and the like. Powders may be formed with the aid of a suitable powder base, e.g., talc, lactose, starch, and the like. Drops may be formulated with an aqueous base or non-aqueous base also comprising one or more dispersing agents, suspending agents, solubilizing agents, and the like. The topical pharmaceutical compositions may also include one or more preservatives or bacteriostatic agents, e.g., methyl hydroxybenzoate, propyl hydroxybenzoate, chlorocreosol, benzalkonium chlorides, and the like.

Solid dosage forms for oral administration include, but are not limited to, capsules, tablets, pills, powders, and granules. In such solid dosage forms, the active agent may be admixed with one or more of the following: (a) one or more inert excipients (or carriers), such as sodium citrate or dicalcium phosphate; (b) fillers or extenders, such as starches, lactose, sucrose, glucose, mannitol, and silicic acid; (c) binders, such as carboxymethylcellulose, alignates, gelatin, polyvinylpyrrolidone, sucrose, and acacia; (d) humectants, such as glycerol; (e) disintegrating agents, such as agar-agar, calcium carbonate, potato or tapioca starch, alginic acid, certain complex silicates, sodium starch glycolate, and sodium carbonate; (f) solution retarders, such as paraffin; (g) absorption accelerators, such as quaternary ammonium compounds; (h) wetting agents, such as cetyl alcohol and glycerol monostearate; (i) adsorbents, such as kaolin and bentonite; and (j) lubricants, such as talc, calcium stearate, magnesium stearate, solid polyethylene glycols, sodium lauryl sulfate, and combinations comprising one or more of the foregoing additives. For capsules, tablets, and pills, the dosage forms may also comprise buffering agents.

The fenofibric acid compositions are useful in treating conditions such as hypercholesterolemia, hypertriglyceridemia, cardiovascular disorders, coronary heart disease, and peripheral vascular disease (including symptomatic carotid artery disease). The fenofibric acid compositions can be used as adjunctive therapy to diet for the reduction of LDL-C, total-C, triglycerides, and Apo B in adult patients with primary hypercholesterolemia or mixed dyslipidemia (Fredrickson Types IIa and IIb). The fenofibric acid compositions can also be used as adjunctive therapy to diet for treatment of adult patients with hypertriglyceridemia (Fredrickson Types IV and V hyperlipidemia). Markedly elevated levels of serum tryglycerides (e.g., >2000 mg/dL) may increase the risk of developing pancreatitis. The fenofibric acid compositions can also be used for other indications where lipid regulating agents are typically used.

In one embodiment, a fenofibric acid dosage form comprises about 10 mg to about 200 mg of fenofibric acid. In another embodiment, a fenofibric acid dosage form comprises about 67.5 to about 103.5 mg of fenofibric acid. In some embodiments, the size of the dose of fenofibric acid compared to fenofibrate can be reduced (on a mg/mg basis) yet still achieve bioequivalence to marketed fenofibrate containing products.

In one embodiment, a fenofibric acid dosage form comprises fenofibric acid, wherein the dosage form provides increased bioavailability in a mammal in comparison to the dosage form comprising the molecular equivalent amount of fenofibrate as the active principle. By molecular equivalent, it is meant that the number of moles of fenofibric acid is equivalent to the number of moles of fenofibrate.

In another embodiment, a fenofibric acid dosage form comprises fenofibric acid, wherein the dosage form is bioequivalent to a reference drug according to NDA #021656, wherein the dosage form contains less amount of fenofibric acid than the fenofibric acid in the dosage form according to NDA #021656 when calculated based on molecular equivalence.

The fenofibric acid content ordinarily constitutes 5 to 60 wt. %, specifically 7 to 40 wt. % and, and more specifically, 10 to 30 wt. % of the formulation. Data in % by weight are based, unless indicated otherwise, on the total weight of the formulation.

In one embodiment, fenofibric acid is combined with a second active agent. In particular, those agents with an action like that of fenofibric acid, e.g., other lipid regulating agents, such as further fibrates, e.g., bezafibrate, ciprofibrate and gemfibrocil, or statins, e.g., lovastatin, mevinolin, pravastatin, fluvastatin, atorvastatin, itavastatin, mevastatin, rosuvastatin, velostatin, synvinolin, simvastatin, cerivastatin and numerous others mentioned in, for instance, WO 02/067901 may be employed.

In another embodiment, fenofibric acid is combined with an agent suitable for the treatment of high blood pressure such as, for example, diuretics (chlorthalidone, furosemide, hydrochlorothiazide, indapamide, metolazone, amiloride hydrochloride, spironolactone, and triamterene), beta-blockers (acebutolol, atenolol, betaxolol, bisoprolol fumarate, carteolol hydrochloride, metoprolol tartrate, metoprolol succinate, nadolol, penbutolol sulfate, pindolol, propranolol hydrochloride, and timolol maleate), sympathetic nerve inhibitors (guanadrel, guanethidine monosulfate, and reserpine), vasodilators (hydralazine hydrochloride and minoxidil), angiotensin-converting enzyme (ACE) inhibitors (benazepril hydrochloride, captopril, enalapril maleate, fosinopril sodium, lisinopril, moexipril, quinapril hydrochloride, ramipril and trandolapril), angiotensin II receptor blockers (candesartan, irbesarten, losartin potassium, and valsartan) and the calcium antagonists (calcium channel blockers, e.g, amlodipine besylate, diltiazem hydrochloride, felodipine, isradipine, nicardipine, nifedipine, nisoldipine, and verapamil hydrochloride).

In another embodiment, fenofibric acid is combined with aspirin or other blood thinning agents such as Coumadin® (warfarin), Dicumarol® (dicumarol), and Miradon® (anisinidione).

In yet another embodiment, fenofibric acid is combined with a calcium supplement, such as, for example, calcium citrate. A method of improving the absorption of fenofibric acid comprises coadministering with a calcium supplement, i.e., calcium citrate.

In one embodiment, a combination fenofibric acid dosage form comprises a multilayer tablet wherein each layer comprises a different active agent.

Unless defined otherwise, technical and scientific terms used herein have the same meaning as is commonly understood by one of skill in the art to which this invention belongs.

Without being held to theory, the higher $C_{max}$ of fenofibric acid under fasted compared to non-fasted conditions may be due to the physical properties of the dosage form such as the tablet hardness and/or disintegration speed contribute to this difference in $C_{max}$.

In one embodiment, the physical properties of the dosage form such as the tablet hardness contribute to the observed difference in $C_{max}$ for certain immediate-release fenofibric acid dosage forms administered under fasted compared to non-fasted conditions. The hardness of one immediate-release fenofibric acid tablet tested herein was about 27 to about 37 kp, produced with a compression force set point of 13.4 kN. Thus, one strategy for obtaining a fenofibric acid dosage form that is bioequivalent under fasted and non-fasted conditions is to adjust the hardness of the immediate-release tablet. In this embodiment, an immediate-release fenofibric acid tablet produced with a hardness of 36 to 44 kp is bioequivalent when dosed under fasted compared to non-fasted conditions. Alternatively, adjusting the process conditions to affect the physical properties of the fenofibric acid dosage form, so that the disintegration rate of the tablet is slowed will result in a dosage form that is bioequivalent under fasted and non-fasted conditions. In one embodiment, a fenofibric acid tablet has a disintegration time of greater than 5 minutes when measured in accordance with a USP method in 0.1 N HCl.

Embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Example 1

Exemplary Fenofibric Acid Dosage Forms

TABLE 1

Fenofibric acid tablets

| Ingredient | mg/tablet | mg/tablet | mg/tablet | mg/tablet |
|---|---|---|---|---|
| Fenofibric acid | 50.0 | 75 | 90 | 130.0 |
| Avicel PH102 | 313.3 | 470 | 564 | 814.7 |
| Povidone S630 | 20.0 | 30 | 36 | 52.0 |
| Povidone XL10 | 13.3 | 20 | 24 | 34.7 |
| Mg Stearate | 3.3 | 5 | 6 | 8.7 |
| Total | 400.0 | 600 | 720 | 1040 |

TABLE 2

Fenofibric acid batches

| Ingredient (mg/tablet) | 30 mg batch | 32 mg batch | 35 mg batch | 50 mg batch | 75 mg batch | 90 mg batch | 130 mg batch | % |
|---|---|---|---|---|---|---|---|---|
| Fenofibric acid | 30.0 | 32.0 | 35.0 | 50.0 | 75.0 | 90.0 | 130.0 | 12.50 |
| Avicel PH102 | 188.0 | 200.5 | 219.3 | 313.3 | 470.0 | 564.0 | 814.7 | 78.33 |
| Povidone S630 | 12.0 | 12.8 | 14.0 | 20.0 | 30.0 | 36.0 | 52.0 | 5.00 |
| Povidone XL10 | 8.0 | 8.5 | 9.3 | 13.3 | 20.0 | 24.0 | 34.7 | 3.33 |
| Mg Stearate | 2.0 | 2.1 | 2.3 | 3.3 | 5.0 | 6.0 | 8.7 | 0.83 |
| Total | 240 | 256 | 280 | 400 | 600 | 720 | 1040 | 100.00 |

Dissolution of an exemplary 30 mg tablet formed under 3 press conditions was measured as follows: 900 ml volume, 50 rpm, paddles, regular vessels, 0.05M potassium phosphate buffer, pH6.8. UV detection at 300 nm was performed. The dissolution is given in Table 3 and in FIG. 1.

TABLE 3

Dissolution profile of exemplary 30 mg fenofibric acid tablet

| Time (min) | 4 kp | 9 kp | 15 kp |
|---|---|---|---|
| 0 | 0 | 0 | 0 |
| 5 | 80 | 80 | 48 |
| 15 | 86 | 89 | 88 |
| 30 | 89 | 92 | 95 |
| 45 | 91 | 94 | 96 |
| 60 | 93 | 96 | 97 |

Example 2

Pharmacokinetic Parameters for an Exemplary Fenofibric Acid Dosage Form Dosed Under Fasted Conditions The study was designed as a randomized, single-dose four-way crossover to compare the pharmacokinetic parameters of a 50, 90 or 130 mg fenofibric acid dosage form to Tricor® 145 mg as a reference. Administration was performed under fasted conditions. Twenty healthy adults participated in this comparison study and all of the subjects completed the study. 50 mg test product (A), 90 mg test product (B), 130 mg test product (C) of Fenofibric Acid Tablets or 145 mg reference product (D) of Fenofibrate Tablets (TRICOR® by Abbott Laboratories) were dosed with 240 mL of room temperature water after an overnight fast. Dosing days were separated by a washout period of at least seven days. Blood samples were drawn prior to dosing (pre-dose) and at 0.33, 0.67, 1, 1.33, 1.67, 2, 2.5, 3, 3.5, 4, 5, 6, 8, 10, 12, 16, 24, 36, 48, and 72 hours post-dose. The samples were then analyzed for fenofibric acid.

The following pharmacokinetic parameters may be determined from the plasma concentration data:

The area under the plasma concentration versus time curve $[AUC_t]$ may be calculated using the linear trapezoidal rule from the zero time point to the last measured concentration.

The area under the plasma concentration versus time curve from zero to infinity $[AUC_{0-INF}]$ may be calculated by adding $C_t/K_{elm}$ to AUC where $C_t$ is the last measured concentration and $K_{elm}$ is the elimination rate constant.

The maximum observed plasma concentration $[C_{max}]$ may be obtained by inspection. The $C_{max}$ may also be designated as CMAX.

The time to maximum plasma concentration $[T_{max}]$ may be obtained by inspection. If the same maximum plasma concentration occurs at more than one time point, the first may be chosen as $T_{max}$.

The terminal elimination rate constant $[K_{elm}]$ may be obtained from the slope of the line, fitted by linear least squares regression, through the terminal points of the ln(base e) of the concentration versus time plot for these points.

The half-life $[T_{1/2}]$ may be calculated by the equation $T_{1/2} = 0.693/K_{elm}$.

The data is shown in Tables 4-9.

TABLE 4

Ln-transformed pharmacokinetic parameters, fasted conditions

| | Reference | 50 mg fenofibric acid | % Ratio | 90% Confidence Interval (Lower limit, upper limit) |
|---|---|---|---|---|
| $C_{max}$ (ng/ml) | 10629.71 | 5653.17 | 53.18 | (49.41, 57.24) |
| $AUC_{0-t}$ (hr * ng/ml) | 156937.44 | 73219.02 | 46.65 | (44.42, 49.01) |
| $AUC_{0-INF}$ (hr * ng/ml) | 172570.31 | 83990.21 | 48.67 | (46.4, 51.05) |

TABLE 5

Non-transformed pharmacokinetic parameters, fasted conditions

| | Reference, Least Sq. Mean | 50 mg fenofibric acid, Least Sq. Mean | % Ratio |
|---|---|---|---|
| $T_{max}$ (hr) | 2.484 | 2.361 | 95.04 |
| $k_{elm}$ | 0.038475 | 0.039245 | 102.00 |
| $T_{1/2}$ (hr) | 18.961 | 18.5365 | 97.761 |

TABLE 6

Ln-transformed pharmacokinetic parameters, fasted conditions

| | Reference | 90 mg fenofibric acid | % Ratio | 90% Confidence Interval (Lower limit, upper limit) |
|---|---|---|---|---|
| $C_{max}$ (ng/ml) | 10629.719 | 10311.87 | 97.009 | (90.13, 104.41) |
| $AUC_{0-t}$ (hr * ng/ml) | 156937.44 | 126454.67 | 80.576 | (76.71, 84.64) |
| $AUC_{0-INF}$ (hr * ng/ml) | 172570.31 | 137975.72 | 79.95 | (76.22, 83.87) |

TABLE 7

Non-transformed pharmacokinetic parameters, fasted conditions

| | Reference, Least Sq. Mean | 90 mg fenofibric acid, Least Sq. Mean | % Ratio |
|---|---|---|---|
| $T_{max}$ (hr) | 2.484 | 2.335 | 94.021 |
| $k_{elm}$ | 0.03847 | 0.041365 | 107.51 |
| $T_{1/2}$ (hr) | 18.961 | 17.8395 | 94.085 |

TABLE 8

Ln-transformed pharmacokinetic parameters, fasted conditions

| | Reference | 130 mg fenofibric acid | % Ratio | 90% Confidence Interval (Lower limit, upper limit) |
|---|---|---|---|---|
| $C_{max}$ (ng/ml) | 10629.71 | 14951.18 | 140.65 | (130.68, 151.39) |
| $AUC_{0-t}$ (hr*ng/ml) | 156937.44 | 182583.65 | 116.34 | (110.76, 122.2) |
| $AUC_{0-INF}$ (hr*ng/ml) | 172570.316 | 195265.22 | 113.15 | (107.87, 118.69) |

TABLE 9

Non-transformed pharmacokinetic parameters, fasted conditions

|  | Reference, Least Sq. Mean | 130 mg fenofibric acid, Least Sq. Mean | % Ratio |
|---|---|---|---|
| $T_{max}$ (hr) | 2.484 | 2.4775 | 99.738 |
| $k_{elm}$ | 0.038475 | 0.040155 | 104.36 |
| $T_{1/2}$ (hr) | 18.961 | 18.159 | 95.7702 |

Example 3

Pharmacokinetic Parameters for an Exemplary Fenofibric Acid Dosage Form Dosed Under Non-Fasted Conditions: High Fat Meal The study was designed as a randomized, single-dose three-way crossover to compare the pharmacokinetic parameters of a 90 or 130 mg fenofibric acid dosage form to Tricor® 145 mg as a reference. Administration was performed under non-fasted conditions. Nine healthy adults participated in this comparison study and all of the subjects completed the study. 90 mg test product (A) and 130 mg test product (B) of Fenofibric Acid Tablets or 145 mg reference product (C) of Fenofibrate Tablets (TRICOR® by Abbott Laboratories) were dosed with 240 mL of room temperature water 30 minutes after initiation of a high-fat and high-calorie breakfast preceded by an overnight fast. Dosing days were separated by a washout period of at least seven days. Blood samples were drawn prior to dosing (pre-dose) and at 0.33, 0.67, 1, 1.33, 1.67, 2, 2.5, 3, 3.5, 4, 5, 6, 8, 10, 12, 16, 24, 36, 48, and 72 hours post-dose. The samples were then analyzed for fenofibric acid.

TABLE 10

Ln-transformed pharmacokinetic parameters, non-fasted conditions

|  | Reference | 90 mg fenofibric acid | % Ratio | 90% Confidence Interval (Lower limit, upper limit) |
|---|---|---|---|---|
| $C_{max}$ (ng/ml) | 10563.18 | 6910.78 | 65.4 | (60.57, 70.66) |
| $AUC_{0-t}$ (hr*ng/ml) | 139882.05 | 106017.82 | 75.79 | (68.51, 83.85) |
| $AUC_{0-INF}$ (hr*ng/ml) | 116947.03 | 151990.96 | 76.94 | (69.81, 84.81) |

TABLE 11

Non-transformed pharmacokinetic parameters, non-fasted conditions

|  | Reference, Least Sq. Mean | 90 mg fenofibric acid, Least Sq. Mean | % Ratio |
|---|---|---|---|
| $T_{max}$ (hr) | 2.87 | 3.07 | 107.08 |
| $k_{elm}$ | 0.043 | 0.044 | 101.50 |
| $T_{1/2}$ (hr) | 16.91 | 17.07 | 100.97 |

TABLE 12

Ln-transformed pharmacokinetic parameters, non-fasted conditions

|  | Reference | 130 mg fenofibric acid | % Ratio | 90% Confidence Interval (Lower limit, upper limit) |
|---|---|---|---|---|
| $C_{max}$ (ng/ml) | 10563.18 | 10691.76 | 101.21 | (93.71, 109.33) |
| $AUC_{0-t}$ (hr*ng/ml) | 139882.05 | 154006.83 | 110.097 | (99.52, 121.8) |
| $AUC_{0-INF}$ (hr*ng/ml) | 151990.96 | 167922.51 | 110.481 | (100.24, 121.78) |

TABLE 13

Non-transformed pharmacokinetic parameters, non-fasted conditions

|  | Reference, Least Sq. Mean | 130 mg fenofibric acid, Least Sq. Mean | % Ratio |
|---|---|---|---|
| $T_{max}$ (hr) | 2.87 | 3.185 | 110.994 |
| $k_{elm}$ | 0.04357 | 0.0432 | 99.158 |
| $T_{1/2}$ (hr) | 16.91 | 16.57 | 98.00 |

Example 4

Pharmacokinetic Parameters for an Exemplary Fenofibric Acid Dosage Form Dosed Under Non-Fasted Conditions: Standard and Low Fat Meal The study is designed as a randomized, single-dose three-way crossover to compare the pharmacokinetic parameters of a 90 mg fenofibric acid dosage form to Tricor® 145 mg as a reference under different non-fasting conditions. Eighteen healthy adults will participate in this comparison study. 90 mg test product (A) of Fenofibric Acid Tablets or 145 mg reference product (B) of Fenofibrate Tablets (TRICOR® by Abbott Laboratories) are dosed with 240 mL of room temperature water 30 minutes after initiation of a standard breakfast or a low fat breakfast preceded by an overnight fast. Dosing days are separated by a washout period of at least seven days. Blood samples are drawn prior to dosing (pre-dose) and at 0.33, 0.67, 1, 1.33, 1.67, 2, 2.5, 3, 3.5, 4, 5, 6, 8, 10, 12, 16, 24, 36, 48, and 72 hours post-dose. The samples are then analyzed for fenofibric acid.

Example 5

Exemplary Quality Control of Drug Substance, which is Substantially Free of Fenofibrate Fenofibric acid is screened using a titrimetric method, in which purity was well within the acceptance criteria of greater than 98% pure. Other quality control measurements were also performed and are listed in Table 1, however this should not be interpreted as narrowing the scope of definition of purity of the drug substance as recognized by a person skill in the art.

TABLE 14

| Test Type | Test Method | Acceptance Criteria |
|---|---|---|
| Melting point |  | 179-185° C. |
| Water content | K. Fischer | Not more than 2.5% |

TABLE 14-continued

| Test Type | Test Method | Acceptance Criteria |
|---|---|---|
| Loss on drying | | Not more than 2.5% |
| Content of 4-chloro-4'-hydroxybenzophenone | HPLC or other chromatographic method | Not more than 1% |
| Purity for fenofibric acid | Titrimetric or HPLC or other chromatographic method | 97.5-103% |
| Content of fenofibrate | HPLC or other chromatographic method | Not more than 2% |
| Content of Ethyl acetate | Gas chromatograph or other suitable chromatographic method | Not more than 2000 ppm |
| Content of methanol | Gas chromatograph or other suitable chromatographic method | Not more than 1000 ppm |
| Tapped density | | Not less than 1.3 g/mL |
| Bulk density | | Not less than 0.7 g/mL |
| Particle size | Light scattering (e.g., Malvern) | D(0, 9) not more than 130 u<br>D(5, 5) not more than 70 u |

The crystal form of fenofibric acid in samples of fenofibric acid and in formulations according to the present invention were tested using standard methodologies of Raman spectroscopy and powder x-ray diffraction (PXRD). The characteristic Raman and PXRD peaks for fenofibric acid are given in Table 14. The formulations employed in Examples 1-3 above were Form A fenofibric acid, and no significant change in crystal form was observed during processing.

TABLE 15

| | Form A | Form B |
|---|---|---|
| Raman Unique bands (cm$^{-1}$) | 1647, 1239, 1211, 1115, 859, 845, 770, 657, 510, 473 | 1632, 1325, 1259, 1158, 835, 827, 642, 567 |
| XRPD Unique peaks (2θ) | 15.4, 28.9 | 7.7, 7.9, 24.5, 28.8, 17.4 |

Example 6

Exemplary Formulation for Composition with 130 mg Fenofibric Acid

A composition comprising 130 mg fenofibric acid is described in Table 16:

TABLE 16

| Ingredient | Mg/tab | % |
|---|---|---|
| Fenofibric acid | 130 | 26 |
| Magnesium carbonate | 150 | 30 |
| Avicel PH 102 | 150 | 30 |
| Povidone S630 | 35 | 7 |
| Povidone XL 10 | 30 | 6 |
| Magnesium Stearate | 5 | 1 |
| Total Weight | 500 | 100 |

Fenofibric acid, magnesium carbonate, Avicel and povidone are placed in a 10 liter high shear gral and mixed. While mixing, alcohol is added to form a first mixture. The first mixture is then discharged and dried in an oven under 50° C. until LOD (loss on drying) exhibited less than 2% using the conventional test method to form a dried first mixture. The dried first mixture is then milled and then transferred into a mixer. Povidone and magnesium stearate are added into the mixer and mixed with the dried first mixture to form a blend. The blend can be further processed into tablets using conventional compression technology or encapsulated into capsules, or any suitable dosage form.

Example 7

Exemplary Formulation for Composition with 130 mg Fenofibric Acid

A composition comprising 130 mg fenofibric acid is described in Table 17:

TABLE 17

| Ingredient | Mg/tab | % |
|---|---|---|
| Fenofibric acid | 130 | 12.5 |
| Avicel PH 102 | 814.7 | 78.3 |
| Povidone S630 | 52.0 | 5.0 |
| Povidone XL 10 | 34.7 | 3.3 |
| Magnesium Stearate | 8.7 | 0.8 |
| Total Weight | 1040 | 100 |

Fenofibric acid, Avicel and the Povidones are screened through a 20 mesh screen into a 2 cu. ft. Gemco Blender and blended for 5 minutes without an intensifier bar. Magnesium stearate is screened through a 25 mesh screen into the same blender and mixed for 1 to 2 minutes to form a blend. The blend is discharged. The blend can be further processed into tablets using conventional compression technology or encapsulated into capsules, or any suitable dosage form.

Example 8

Exemplary Formulation for Composition with 10-20 mg Fenofibric Acid

A composition comprising 10-20 mg fenofibric acid is described in Table 18:

TABLE 18

| Ingredient | Amount (mg/tablet) |
|---|---|
| Fenofibric acid | 10-20 |
| Sprayed mixture of Mannitol, Sorbitol, Crospovidone and Silicon dioxide | 165 |
| Mannitol, USP | 100 |
| Entrapped Peppermint Flavor | 5 |
| Stearic Acid, NF | 10 |

The composition is formed by mixing, granulating and/or blending the ingredients using a conventional wet or dry granulation process. The mixture can be further processed into tablets using conventional compression technology or encapsulated into capsules, or any suitable dosage form.

Example 9

Exemplary Formulation for Composition with 10 mg Fenofibric Acid

A composition with 10 mg fenofibric acid is described in Table 19:

TABLE 19

| Ingredient | Amount (mg/tablet) |
|---|---|
| Fenofibric acid | 10 |
| HPMC K4MCR | 280 |
| Avicel pH 101 | 54 |
| Colloidal silicon dioxide | 2 |
| Magnesium stearate | 4 |

The composition is formed by mixing, granulating and/or blending the ingredients using conventional wet or dry granulation process. The mixture can be further processed into tablets using conventional compression technology or encapsulated into capsules, or any suitable dosage form.

Example 10

Exemplary Formulation for Composition with 130 mg Fenofibric Acid

Fenofibric acid is made into a core composition. The core is then coated with a delayed release functional coat. Optionally, the coated core is coated with an additional cosmetic or functional coating. An exemplary core composition is described in Table 3 and coating in Table 20.

TABLE 20

| Ingredient | Amount (mg/tablet) |
|---|---|
| EUDRAGIT® L30D55 | 12-20 |
| Triethyl citrate | 4-8 |
| Talc | 8 |

Example 11

105 mg Fenofibric Acid Dosage Forms

A capsule was filled with a composition according to Table 21.

TABLE 21

| Component | Mg in capsule |
|---|---|
| Fenofibric acid | 105 |
| Lactose monohydrate | 229 |
| Sodium lauryl sulfate | 15 |
| Magnesium stearate | 1 |

A tablet was made by forming a blend as given in Table 22 and compressing 840 mg of the blend into a tablet to produce a 105 mg fenofibric acid tablet.

TABLE 22

| Component | Mg/g blend |
|---|---|
| Fenofibric acid | 125 |
| Microcrystalline cellulose | 783.4 |
| Crospovidone, Plasdone S-630 | 50 |
| Crospovidone NF, Polyplasdone XL 10 | 33.3 |
| Magnesium stearate | 8.3 |

Fenofibric acid, Microcrystalline Cellulose, NF, Copovidone, NF, and Crospovidone, NF are de-lumped by passing the material through a 20-Mesh Screen. The screened material is blended in a 75 cu. Ft. Gemco Double Cone Blender for ten (10) minutes. The pre-screened Magnesium Stearate, NF is de-lumped by it passing the material through a 20-Mesh. The Screened Magnesium Stearate, NF is added into the Gemco Double Cone Blender and the blending is continued for another three (3) minutes. The final blend is discharged from the Gemco Double Cone Blender. This final blend is divided into four (4) parts, which is equivalent to approximately 200,000 units for the fenofibric acid tablets. The final blends are compressed into tablets on a Synthesis 300 Tablet Press. The tablets are packaged into HDPE bottles for storage.

Example 12

Pharmacokinetic Parameters for an Exemplary Fenofibric Acid Dosage Form Dosed Under Fasted and Non-Fasted Conditions The study was designed as an open-label, single-dose, randomized, two-period, two-treatment crossover study to compare the pharmacokinetic parameters of a 105 mg fenofibric acid dosage form to Tricor® 145 mg as a reference under fasting and non-fasting conditions. The study enrolled 54 non-obese, non-smoking, generally healthy adult volunteers. Each subject received a single dose of each product in a randomly assigned sequence, separated by a 7-day washout period. 105 mg test product (A) of Fenofibric Acid tablets or 145 mg reference product (B) of Fenofibrate Tablets (TRICOR® by Abbott Laboratories) were dosed with 240 mL of room temperature water 30 minutes after initiation of a standard breakfast (575 calories of which 36% are contributed by fat) preceded by an overnight fast (minimum 10 hours) for non-fasting conditions. 105 mg test product (A) of Fenofibric Acid Tablets or 145 mg reference product (B) of Fenofibrate Tablets (TRICOR® by Abbott Laboratories) were dosed with 240 mL of room temperature water 30 minutes after initiation of a standard breakfast preceded by an overnight fast followed by continued fast for 2 hours after administration of the dosage form for fasting conditions. Dosing days are separated by a washout period of at least seven days. Blood samples are drawn prior to dosing (pre-dose) and at 0.5, 1.0, 1.5, 2, 2.5, 3, 3.5, 4, 5, 6, 8, 10, 12, 16, 24, 36, 48, and 72 hours post-dose. The samples are then analyzed for fenofibric acid.

TABLE 23

Ln-transformed pharmacokinetic parameters, fasted conditions

| | Reference | 105 mg fenofibric acid | % Ratio | 90% Confidence Interval (Lower limit, upper limit) |
|---|---|---|---|---|
| $C_{max}$ (ng/ml) | 10650. | 12001. | 112.6 | (107.99, 117.59) |
| $AUC_{0-t}$ (hr*ng/ml) | 158700 | 148593 | 93.63 | (91.28, 96.05) |
| $AUC_{0-INF}$ (hr*ng/ml) | 173933 | 162956 | 93.68 | (91.67, 95.75) |

TABLE 24

Non-transformed pharmacokinetic parameters, fasted conditions

|  | Reference, Least Sq. Mean | 105 mg fenofibric acid, Least Sq. Mean | % Ratio |
|---|---|---|---|
| $T_{max}$ (hr) | N/A | N/A | N/A |
| $k_{elm}$ | 0.0377 | 0.0402 | 106.69 |
| $T_{1/2}$ (hr) | 18.94 | 19.69 | 96.16 |

TABLE 25

Ln-transformed pharmacokinetic parameters, non-fasted conditions

|  | Reference | 105 mg fenofibric acid | % Ratio | 90% Confidence Interval (Lower limit, upper limit) |
|---|---|---|---|---|
| $C_{max}$ (ng/ml) | 9300 | 8369 | 89.98 | (86.78, 93.31) |
| $AUC_{0-t}$ (hr*ng/ml) | 123915 | 113625 | 91.69 | (89.73, 93.7) |
| $AUC_{0-INF}$ (hr*ng/ml) | 137016 | 124885 | 91.14 | (89.08, 93.26) |

TABLE 26

Non-transformed pharmacokinetic parameters, non-fasted conditions

|  | Reference, Least Sq. Mean | 105 mg fenofibric acid, Least Sq. Mean | % Ratio |
|---|---|---|---|
| $T_{max}$ (hr) | N/A | N/A | N/A |
| $k_{elm}$ | 0.0417 | 0.045 | 108.2 |
| $T_{1/2}$ (hr) | 18.48 | 17.16 | 92.86 |

Individual Tmax's for the fasted patients treated with the fenofibric acid dosage form are 2, 4, 1.5, 1.5, 1, 5, 2.5, 1.5, 2, 1.5, 2.5, 4, 5, 1.5, 3, 4, 1, 1, 3.5, 2.5, 1, 1.5, 3, 4, 5, 2.5, 3.5, 4, 4, 2.5, 1, 2.5, 1.53, 4, 2, 2.5, 1, 1.5, 2, 2.5, 2, 5, 4, 2, 1.5, 2.5, 3.5, 1, 1.5. The mean is 2.63±1.27 with a minimum of 1 and a maximum of 5.

Individual Tmax's for the non-fasted patients treated with the fenofibric acid dosage form are 3, 3.5, 4, 5, 3.5, 4, 5, 1.5, 3, 5, 5, 5, 3.5, 5, 2, 5, 5, 5, 5, 4, 3.5, 4, 4, 5, 3, 4, 3.05, 6, 8, 3.5, 3.5, 3.5, 3, 2.5, 4, 1.5, 5, 3.5, 5, 5.08, 4, 3.5, 5, 6, 3.5, 5, 3.5, 3, 3. The mean is 4.06±1.21 with a minimum of 1.5 and a maximum of 8.

AUC data was calculated in two ways. 1) Using the trapezoid rule from the fasting and non-fasting studies. 2) Fitting the data to a two-compartment model function, which was used to calculate AUC's. The results were compared for all AUC's from 0 to 24 hours and were nearly identical after three hours (within 1% in all cases). For times up to 3 hours, a few AUC's were as much as 8% different. AUC's for 0-1, 0-2, 0-3 and 3-6 hours were calculated using the biodata (Method 1). Since there was no 9 hour data point, the 3-9 hour AUC was calculated from the fitted function (Method 2)

TABLE 27

| Interval | Fenofibric Acid; fasting 105 mg AUC ng-h/mL | Tricor ®; fasting 145 mg AUC ng-h/mL | Fenofibric acid; non-fasting 105 mg AUC ng-h/mL | Tricor ®; non-fasting 145 mg AUC ng-h/mL |
|---|---|---|---|---|
| 0-1 hr | 2979 | 2554 | 736 | 150 |
| 0-2 hr | 10403 | 10425 | 3881 | 2500 |
| 0-3 hr | 19700 | 20000 | 9230 | 8553 |
| 3-6 hr | 26287 | 26446 | 21228 | 23750 |
| 3-9 hr | 46287 | 46697 | 38516 | 42380 |

Example 13

Pharmacokinetic Parameters for an Exemplary Fenofibric Acid Dosage Form Dosed Under Fasted and Low Fat, Standard and High-Fat Non-Fasted Conditions The study was designed as an open-label, single-dose, randomized, four period crossover study to compare the pharmacokinetic parameters of a 105 mg fenofibric acid dosage form under fasting and non-fasting conditions. The study enrolled 18 non-obese, non-smoking, generally healthy adult volunteers. Each subject received a single dose of each product in a randomly assigned sequence, separated by a 7-day washout period.

105 mg test product of Fenofibric Acid tablets was dosed under fasted conditions (treatment D), a low-fat meal (treatment A), a standard meal (treatment B) or a high-fat meal (treatment C). Fasting conditions were dosing with 240 mL of room temperature water followed by continued fast for 2 hours after administration of the dosage form. Non-fasting conditions were dosing with 240 mL of room temperature water 30 minutes after initiation of a low-fat, standard or high-fat breakfast preceded by an overnight fast. Dosing days are separated by a washout period of at least seven days. Blood samples are drawn prior to dosing (pre-dose) and at 0.33, 0.67, 1.0, 1.33, 1.67, 2, 2.5, 3, 3.5, 4, 5, 6, 7, 8, 9, 10, 12, 16, 24, 36, 48, and 72 hours post-dose. The samples are then analyzed for fenofibric acid.

TABLE 28

Ln-transformed pharmacokinetic parameters for fasted conditions compared to a low-fat meal

|  | A, low-fat meal | D, fasted | % Ratio | 90% Confidence Interval (Lower limit, upper limit) |
|---|---|---|---|---|
| $C_{max}$ (ng/ml) | 9564.9 | 11840.9 | 80.78 | (76.7, 85.08) |
| $AUC_{0-t}$ (hr*ng/ml) | 124223 | 132066 | 94.06 | (91.06, 97.16) |
| $AUC_{0-INF}$ (hr*ng/ml) | 135769 | 143544 | 94.58 | (91.55, 97.72) |

TABLE 29

Non-transformed pharmacokinetic parameters for fasted conditions compared to a low-fat meal

|  | A, low-fat meal | D, fasted | % Ratio |
|---|---|---|---|
| $C_{max}$ (ng/ml) | 9781 | 12044 | 81.21 |
| $AUC_{0-t}$ (hr*ng/ml) | 132677 | 140160 | 94.66 |

TABLE 29-continued

Non-transformed pharmacokinetic parameters for fasted
conditions compared to a low-fat meal

|  | A, low-fat meal | D, fasted | % Ratio |
|---|---|---|---|
| $AUC_{0\text{-}INF}$ (hr*ng/ml) | 145996 | 152812 | 95.54 |
| $T_{max}$ (hr) | 3.55 | 1.97 | 180.41 |
| $k_{elm}$ | 0.0449 | 0.0453 | 99.17 |
| $T_{1/2}$ (hr) | 17.38 | 16.83 | 103.25 |

TABLE 30

Ln-transformed pharmacokinetic parameters for fasted
conditions compared to a standard meal

|  | B, standard meal | D, fasted | % Ratio | 90% Confidence Interval (Lower limit, upper limit) |
|---|---|---|---|---|
| $C_{max}$ (ng/ml) | 9691.13 | 11840.9 | 81.85 | (77.71, 86.2) |
| $AUC_{0\text{-}t}$ (hr*ng/ml) | 125951 | 132066 | 95.37 | (92.32, 98.52) |
| $AUC_{0\text{-}INF}$ (hr*ng/ml) | 137286 | 143544 | 95.64 | (92.57, 98.81) |

TABLE 31

Non-transformed pharmacokinetic parameters for fasted
conditions compared to a standard meal

|  | B, standard meal | D, fasted | % Ratio |
|---|---|---|---|
| $C_{max}$ (ng/ml) | 9864 | 12044 | 0.8190 |
| $AUC_{0\text{-}t}$ (hr*ng/ml) | 134714 | 140160 | 0.9611 |
| $AUC_{0\text{-}INF}$ (hr*ng/ml) | 148059 | 152812 | 0.9689 |
| $T_{max}$ (hr) | 3.65 | 1.97 | 185.38 |
| $k_{elm}$ | 0.0444 | 0.0453 | 98.18 |
| $T_{1/2}$ (hr) | 17.24 | 16.83 | 102.43 |

TABLE 32

Ln-transformed pharmacokinetic parameters for fasted
conditions compared to a high-fat meal

|  | C, high-fat meal | D, fasted | % Ratio | 90% Confidence Interval (Lower limit, upper limit) |
|---|---|---|---|---|
| $C_{max}$ (ng/ml) | 7745 | 11840.9 | 65.42 | (62.11, 68.9) |
| $AUC_{0\text{-}t}$ (hr*ng/ml) | 127262 | 132066 | 96.36 | (93.29, 99.54) |
| $AUC_{0\text{-}INF}$ (hr*ng/ml) | 139065 | 143544 | 96.88 | (93.77, 100.09) |

TABLE 33

Non-transformed pharmacokinetic parameters for fasted
conditions compared to a high-fat meal

|  | C, high-fat meal | D, fasted | % Ratio |
|---|---|---|---|
| $C_{max}$ (ng/ml) | 7983 | 12044 | 0.6626 |
| $AUC_{0\text{-}t}$ (hr*ng/ml) | 134802 | 140160 | 0.9618 |
| $AUC_{0\text{-}INF}$ (hr*ng/ml) | 148435 | 152812 | 0.9714 |
| $T_{max}$ (hr) | 4.01 | 1.97 | 203.49 |
| $k_{elm}$ | 0.0447 | 0.0453 | 98.62 |
| $T_{1/2}$ (hr) | 17.37 | 16.83 | 103.21 |

Example 14

Pharmacokinetic Parameters for an Exemplary Fenofibric Acid Capsule Form Compared to Tricor® 145 Under Fasted Conditions The study was designed as an open-label, single-dose, randomized, three-way crossover study to compare the pharmacokinetic parameters of a 105 mg fenofibric acid capsule to Tricor® 145 mg as a reference under fasted conditions. The study enrolled 18 non-obese, non-smoking, generally healthy adult volunteers. Each subject received a single dose of each product in a randomly assigned sequence, separated by a 7-day washout period. 105 mg test product (A) of Fenofibric Acid capsules or 145 mg reference product (B) of Fenofibrate Tablets (TRICOR® by Abbott Laboratories) were dosed with 240 mL of room temperature water preceded by an overnight fast followed by continued fast for 2 hours after administration of the dosage form for fasting conditions. Dosing days are separated by a washout period of at least seven days. Blood samples are drawn prior to dosing (pre-dose) and at 0.33, 0.67, 1.0, 1.33, 1.67, 2, 2.5, 3, 3.5, 4, 5, 6, 7, 8, 9, 10, 12, 16, 24, 36, 48, and 72 hours post-dose. The samples are then analyzed for fenofibric acid.

TABLE 34

Ln-transformed pharmacokinetic parameters for
fasted conditions

|  | 105 mg fenofibric acid tablet | Reference | % Ratio | 90% Confidence Interval (Lower limit, upper limit) |
|---|---|---|---|---|
| $C_{max}$ (ng/ml) | 10826 | 9631 | 112.41 | (99.15, 127.45) |
| $AUC_{0\text{-}t}$ (hr*ng/ml) | 136404 | 144195 | 94.6 | (88.85, 100.73) |
| $AUC_{0\text{-}INF}$ (hr*ng/ml) | 148659 | 157813 | 94.2 | (88.58, 100.18) |

TABLE 35

Non-transformed pharmacokinetic parameters for
fasted conditions

|  | 105 mg fenofibric acid tablet | Reference | % Ratio |
|---|---|---|---|
| $T_{max}$ (hr) | 2.56 | 2.62 | 97.52 |
| $k_{elm}$ | 0.0425 | 0.0390 | 109.09 |
| $T_{1/2}$ (hr) | 18.1 | 19.06 | 94.95 |

Example 15

Pharmacokinetic Parameters for an Exemplary Fenofibric Acid Capsule Form Under Fasted Conditions Compared to a High Fat Meal The study was designed as an open-label, single-dose, randomized, three-way crossover study to compare the pharmacokinetic parameters of a 105 mg fenofibric acid capsule to Tricor® 145 mg as a reference under fasting conditions. The study enrolled 18 non-obese, non-smoking, generally healthy adult volunteers. Each subject received a single dose of each product in a randomly assigned sequence, separated by a 7-day washout period. 105 mg test product (A) of Fenofibric Acid capsules or 145 mg reference product (B) of Fenofibrate Tablets (TRICOR® by Abbott Laboratories)

were dosed with 240 mL of room temperature water 30 minutes after initiation of a standardized breakfast preceded by an overnight fast followed by continued fast for 2 hours after administration of the dosage form for fasting conditions. Dosing days are separated by a washout period of at least seven days. Blood samples are drawn prior to dosing (pre-dose) and at 0.33, 0.67, 1.0, 1.33, 1.67, 2, 2.5, 3, 3.5, 4, 5, 6, 7, 8, 9, 10, 12, 16, 24, 36, 48, and 72 hours post-dose. The samples are then analyzed for fenofibric acid.

TABLE 36

Ln-transformed pharmacokinetic parameters for high-fat meal conditions compared to fasting

| | High fat meal | Fasting | % Ratio | 90% Confidence Interval (Lower limit, upper limit) |
|---|---|---|---|---|
| $C_{max}$ (ng/ml) | 7815 | 10826 | 72.19 | (63.67, 81.85) |
| $AUC_{0-t}$ (hr*ng/ml) | 127852 | 136404 | 93.73 | (88.03, 99.8) |
| $AUC_{0-INF}$ (hr*ng/ml) | 139614 | 148659 | 93.92 | (88.31, 99.88) |

TABLE 37

Non-transformed pharmacokinetic parameters for high-fat meal conditions compared to fasting

| | High fat meal | Fasting | % Ratio |
|---|---|---|---|
| $T_{max}$ (hr) | 5.11 | 2.56 | 200 |
| $k_{elm}$ | 0.0430 | 0.0425 | 101 |
| $T_{1/2}$ (hr) | 17.67 | 18.1 | 97.6 |

The use of the terms "a" and "an" and "the" and similar referents (especially in the context of the following claims) are to be construed to cover both the singular and the plural, unless otherwise indicated herein or clearly contradicted by context. The terms "comprising", "having", "including", and "containing" are to be construed as open-ended terms (i.e., meaning "including, but not limited to") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in a suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention as used herein, the terms wt %, weight percent, percent by weight, etc. are equivalent and interchangeable.

The invention claimed is:

1. A method of treating a patient in need of treatment for an indication involving increased cholesterol and/or lipid levels, comprising
administering to the patient an immediate-release 105 mg fenofibric acid dosage form without regard to meals, wherein immediate release is release of 90% or greater of the fenofibric acid in the dosage form at 2 hours measured in a single pH buffer.

2. A method of treating a patient in need of treatment for mixed dyslipidemia, comprising
administering to the patient an immediate-release 105 mg fenofibric acid dosage form without regard to meals, wherein immediate release is release of 90% or greater of the fenofibric acid in the dosage form at 2 hours measured in a single pH buffer.

* * * * *